US010466786B2

(12) United States Patent
Kim et al.

(10) Patent No.: US 10,466,786 B2
(45) Date of Patent: Nov. 5, 2019

(54) METHOD AND DEVICE FOR PROVIDING CONTENT

(71) Applicant: SAMSUNG ELECTRONICS CO., LTD., Suwon-si (KR)

(72) Inventors: Hye-soo Kim, Suwon-si (KR);
Hyun-kwon Chung, Seoul (KR);
Jong-youb Ryu, Suwon-si (KR);
Kyoung-jin Moon, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/573,533

(22) PCT Filed: May 12, 2016

(86) PCT No.: PCT/KR2016/005017
§ 371 (c)(1),
(2) Date: Nov. 13, 2017

(87) PCT Pub. No.: WO2016/182368
PCT Pub. Date: Nov. 17, 2016

(65) Prior Publication Data
US 2018/0113509 A1 Apr. 26, 2018

(30) Foreign Application Priority Data
May 12, 2015 (KR) .................. 10-2015-0066248

(51) Int. Cl.
*H04N 21/4415* (2011.01)
*G06F 3/01* (2006.01)
(Continued)

(52) U.S. Cl.
CPC ............ *G06F 3/015* (2013.01); *G06F 16/436* (2019.01); *G06Q 50/20* (2013.01); *H04W 4/38* (2018.02); *H04N 21/4415* (2013.01)

(58) Field of Classification Search
CPC .................................................. H04N 21/4415
See application file for complete search history.

(56) References Cited

U.S. PATENT DOCUMENTS

| 2014/0139551 A1* | 5/2014 | McCulloch ............ G09G 5/377 345/633 |
| 2016/0063883 A1* | 3/2016 | Jeyanandarajan ....... G09B 7/08 434/201 |

(Continued)

FOREIGN PATENT DOCUMENTS

| JP | 2004-191628 A | 7/2004 |
| JP | 2013-77013 A | 4/2013 |

(Continued)

OTHER PUBLICATIONS

International Search Report and Written Opinion (PCT/ISA/210 & PCT/ISA/237) dated Aug. 8, 2016, issued by the International Searching Authority in counterpart International Application No. PCT/KR2016/005017.

(Continued)

*Primary Examiner* — Michael H Hong
(74) *Attorney, Agent, or Firm* — Sughrue Mion, PLLC

(57) ABSTRACT

The present disclosure is related to technology for a sensor network, machine to machine (M2M) communication, machine type communication (MTC), and Internet of Things (IoT). Provided is a method of providing content, performed by a device, the method including: outputting content from the device; determining a learning state of the user with respect to the content, based on biometric information of a user received from a sensing device; changing the content, based on the determined learning state of the user; and outputting changed content. The present disclosure is applicable to intelligent services based on various technology (e.g., smart home, smart building, smart city, smart car or (Continued)

connected car, health care, digital education, retail business, security, and safety-related service).

13 Claims, 42 Drawing Sheets

(51) Int. Cl.
*G06F 16/435* (2019.01)
*G06Q 50/20* (2012.01)
*H04W 4/38* (2018.01)

(56) References Cited

U.S. PATENT DOCUMENTS

| | | | |
|---|---|---|---|
| 2016/0085432 A1 | 3/2016 | Kim et al. | |
| 2016/0210407 A1 | 7/2016 | Hwang et al. | |
| 2016/0292159 A1* | 10/2016 | Patel | G06F 17/3053 |
| 2017/0315610 A1 | 11/2017 | Sako et al. | |

FOREIGN PATENT DOCUMENTS

| | | |
|---|---|---|
| KR | 10-2006-0007334 A | 1/2006 |
| KR | 10-2012-0035571 A | 4/2012 |
| KR | 10-2012-0065111 A | 6/2012 |
| KR | 10-2013-0082839 A | 7/2013 |
| KR | 10-2014-0021208 A | 2/2014 |
| KR | 10-2014-0063362 A | 5/2014 |
| KR | 10-2016-0036161 A | 4/2016 |
| WO | 2015/047032 A1 | 4/2015 |

OTHER PUBLICATIONS

Jang, et al., "EEG Analysis of Learning Attitude Change of Female College Student on e-Learning" Apr. 2011, Journal of the Korea Contents Association, 11(4), p. 42-50, 10 pages total.

Clark, et al., "E-learning and the science of instruction: Proven guidelines for consumers and designers of multimedia learning" 2011, Pfeiffer, Second edition, 497 pages total.

Schar, et al., "Investigating Means to Reduce Cognitive Load from Animations: Applying Differentiated Measures of Knowledge Representation" 2007, vol. 40, No. 1, pp. 64-78.

Communication dated Jan. 24, 2018, issued by the European Patent Office in counterpart European application No. 16793014.8.

Anonymous, "Sensorimotor rhythm", Dec. 23, 2014, pp. 1-3, XP055488105, Retrieved from the Internet at URL: <https://en.wikipedia.org/w/index.php?title=Sensorimotor_rhythm&oldid=639330429>, retrieved on Jun. 26, 2018.

Communication dated Jul. 3, 2018, issued by the European Patent Office in counterpart European application No. 16793014.8.

Communication dated Apr. 16, 2019, issued by the European Patent Office in counterpart European application No. 16793014.8.

* cited by examiner

FIG. 19

TEXT

| PRIORITY: CONCENTRATION AMOUNT | EDITING METHOD | CONCENTRATION AMOUNT | UNDERSTANDING AMOUNT | STRES AMOUNT | MEMORIZATION AMOUNT |
|---|---|---|---|---|---|
| 1 | SELECT SUB-CONTENT | 30 | 50 | 20 | 10 |
| 2 | EMPHASIZE OBJECT | 50 | 40 | 10 | 30 |
| 3 | CHANGE LOCATION OF OBJECT | 60 | 50 | 10 | 40 |
| 4 | PUBLICIZE OBJECT | 70 | 60 | 10 | 10 |
| 5 | REPLACE OBJECT | 80 | 10 | 20 | 20 |

(a)

| PRIORITY: UNDERSTANDING AMOUNT | EDITING METHOD | CONCENTRATION AMOUNT | UNDERSTANDING AMOUNT | STRES AMOUNT | MEMORIZATION AMOUNT |
|---|---|---|---|---|---|
| 1 | SELECT SUB-CONTENT | 10 | 50 | 30 | 10 |
| 2 | INSERT OBJECT | 30 | 60 | 20 | 20 |
| 3 | CHANGE REPRODUCTION SPEED | 40 | 65 | 20 | 30 |
| 4 | CHANGE REPRODUCTION FREQUENCY | 50 | 70 | 10 | 50 |

(b)

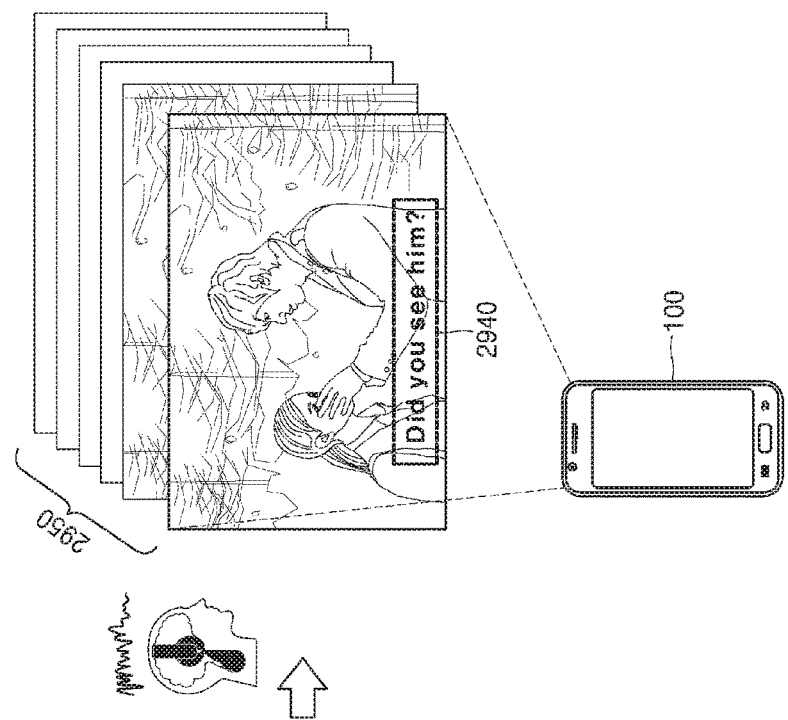
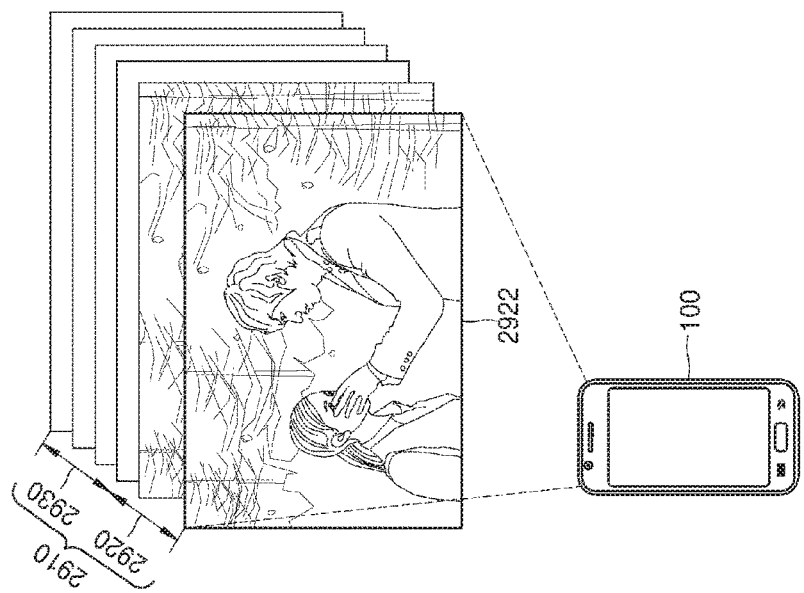
FIG. 29

METHOD AND DEVICE FOR PROVIDING CONTENT

TECHNICAL FIELD

The present invention relates to a method and a device for providing content, and a computer-readable recording medium having recorded thereon a program for executing the method.

BACKGROUND ART

The Internet is being developed from a human-centered network via which people generate and consume information to an Internet of Things (IoT) network via which distributed components, such as things, transmit or receive information to or from each other and process the information. Internet of Everything (IoE) technology, in which big data processing technology is combined with IoT technology via connection with cloud servers or the like, is emerging. To implement IoT, technical elements, such as sensing technology, a wired/wireless communication and network infrastructure, service interface technology, and security technology, are required, and thus a sensor network, machine to machine (M2M) communication, machine type communication (MTC), and the like for connection between things have recently been studied.

In IoT environments, an intelligent Internet Technology (IT) service for collecting and analyzing data generated by connected things and creating a new value in people's lives may be provided. IoT is applicable to various fields, such as smart home, smart building, smart city, smart car or connected car, smart grid, health care, smart home appliances, and advanced medical care, via fusion and combination of existing information technology (IT) with various industries.

DETAILED DESCRIPTION OF THE INVENTION

Technical Problem

A device according to an embodiment of the present invention may effectively provide content according to a state of a user, by providing content based on biometric information of the user.

Technical Solution

According to an aspect of the present invention, there is provided a method of providing content, performed by a device, the method including outputting content from the device; receiving biometric information of a user from a sensing device; determining a learning state of the user with respect to the content, based on the received biometric information; changing the content, based on the determined learning state of the user; and outputting changed content.

DESCRIPTION OF THE DRAWINGS

FIG. 19 illustrates tables for explaining information about content changing methods previously stored in the device, according to an embodiment of the present invention.

FIG. 29 is a schematic diagram for explaining a method in which the device according to an embodiment of the present invention changes some pieces of objects included in sub-content of selected video content, based on received brainwave information of a user.

BEST MODE

Figure 1:
FIG. 1 is a conceptual diagram for describing a method in which a device according to an embodiment of the present invention provides content.

A method of providing content, performed by a device, includes outputting content from the device; receiving biometric information of a user from a sensing device; determining a learning state of the user with respect to the content, based on the received biometric information; changing the content, based on the determined learning state of the user; and outputting changed content.

The determining of the learning state of the user includes determining at least one of a concentration amount, an understanding amount, a stress amount, and a memorization amount of the user with respect to the content, by using brainwave information included in the received biometric information.

The method further includes comparing at least one of the concentration amount, the understanding amount, the stress amount, and the memorization amount of the user with a preset threshold; and determining whether to change the content, based on a result of the comparing.

The changing of the content includes adding second sub-content, which is at least one piece of sub-content included in other content, to first sub-content, which is at least one piece of sub-content included in the content.

The adding includes selecting the first sub-content and the second sub-content; changing the selected first sub-content and the selected second sub-content; and arranging changed first sub-content and changed second sub-content.

The changing of the content includes changing at least one of shapes, colors, sizes, and locations of objects included in at least one piece of sub-content of the content.

The changing of the content includes determining at least one of an output time point, an output frequency, and an output speed of at least one piece of sub-content included in the content.

The changing of the content includes changing some of objects included in at least one piece of sub-content of the content to an object of other sub-content.

The changing of the content includes, based on a learning state of the user while at least one piece of sub-content included in the content is being output, determining at least one of a repetitive output time point and a repetitive output frequency of the output least one piece of sub-content.

A method of providing content, performed by a server includes receiving, by the server, biometric information of a user from a device; determining a learning state of the user with respect to content output by the device, based on the received biometric information; changing the content, based on the determined learning state of the user; and transmitting changed content to the device.

A device includes an output interface configured to output content; a communicator configured to receive biometric information of a user from a sensing device; and a controller configured to determine a learning state of the user with respect to the content, based on the received biometric information, and change the content, based on the determined learning state, wherein the output interface outputs the changed content.

The controller determines at least one of a concentration amount, an understanding amount, a stress amount, and a memorization amount of the user with respect to the content, by using brainwave information included in the received biometric information.

The controller includes at least one of the concentration amount, the understanding amount, the stress amount, and the memorization amount of the user with a preset threshold and determines whether to change the content, based on a result of the comparing.

The controller adds second sub-content, which is at least one piece of sub-content included in other content, to first sub-content, which is at least one piece of sub-content included in the content.

The controller selects the first sub-content and the second sub-content, changes the selected first sub-content and the selected second sub-content; and arranges changed first sub-content and changed second sub-content.

The controller changes at least one of shapes, colors, sizes, and locations of objects included in at least one piece of sub-content of the content.

The controller determines at least one of an output time point, an output frequency, and an output speed of at least one piece of sub-content included in the content.

The controller changes some of objects included in at least one piece of sub-content of the content to an object of other sub-content.

Based on a learning state of the user while at least one piece of sub-content included in the content is being output, the controller determines at least one of a repetitive output time point and a repetitive output frequency of the output least one piece of sub-content.

A server includes a communicator configured to receive biometric information of a user from a device; and a controller configured to determine a learning state of the user with respect to content output by the device, based on the received biometric information, and change the content, based on the determined learning state, wherein the communicator transmits changed content to the device.

MODE OF THE INVENTION

Hereinafter, the terms used in the specification will be briefly described, and then the present invention will be described in detail.

Although general terms widely used at present were selected for describing the present invention in consideration of the functions thereof, these general terms may vary according to intentions of one of ordinary skill in the art, case precedents, the advent of new technologies, and the like. Terms arbitrarily selected by the applicant of the present invention may also be used in a specific case. In this case, their meanings need to be given in the detailed description of the invention. Hence, the terms must be defined based on their meanings and the contents of the entire specification, not by simply stating the terms.

The terms "comprises" and/or "comprising" or "includes" and/or "including" when used in this specification, specify the presence of stated elements, but do not preclude the presence or addition of one or more other elements. The terms " . . . unit" and " . . . module" when used in this specification refers to a unit in which at least one function or In operation is performed, and may be implemented as hardware, software, or a combination of hardware and software.

The term "content" refers to digital information provided via a wired/wireless communication network. Examples of content according to an embodiment of the present invention may include, but are not limited to, video content, such as a TV program, a video on demand (VOD), a personal video (for example, user-created content (UCC)), image content, such as a picture and a drawing, text content, such as an electronic book (poem or novel), a letter, a business file, and a web page, audio content, such as an mp3 sound source and a radio broadcast, and an application, such as a widget and a game.

"content" may include at least one piece of sub-content comprised of a plurality of objects. Herein, an object may be one of a frame, image data, text data, and audio data.

Herein, sub-content may be produced by splitting content according to time, the size of data, and the contents of data, but this is merely an embodiment. The sub-content is not limited thereto.

The video content may include at least one piece of video sub-content comprised of a plurality of frames. For example, in English lecture video content comprised of lectures of first through tenth units, video sub-content may be a video lecture of each unit. The image content may include at least one piece of image sub-content comprised of image data. For example, in 4-frame cartoon image content, image sub-content may be each image frame.

The text content may include at least one piece of text sub-content comprised of text data. For example, in a science digital textbook of 30 pages, text sub-content may be each page. The audio content may include at least one piece of audio sub-content comprised of audio data. For example, in an English recording file about a conversation in a situation of issuing an airline ticket, audio sub-content may be a conversion in each situation, such as arrival at airport, path finding, or ticketing, included in the situation of issuing an airline ticket.

The above description of the sub-content is merely an embodiment of the present invention, and the sub-content may be defined according to what is set in metadata of the content.

The present invention will now be described more fully with reference to the accompanying drawings, in which exemplary embodiments of the invention are shown.

FIG. 1 is a conceptual diagram for describing a method in which a device 100 according to an embodiment of the present invention provides content.

The device 100 according to an embodiment of the present invention may output content. The device 100 may select one of a plurality of pieces of content that may be output by the device 100, based on an input of a user. For example, the device 100 may select content corresponding to a touch input of the user from among respective icons of a plurality of pieces of content that are output on a screen of the device 100.

The device 100 according to an embodiment of the present invention may obtain biometric information of the user.

For example, the device 100 may receive the biometric information of the user from a sensing device 10. As another example, the device 100 may obtain the biometric information of the user from a sensor included in the device 100.

The device 100 according to an embodiment of the present invention may determine a learning state of the user, based on the obtained biometric information of the user. The learning state of the user may be determined based on at least one of a concentration amount of the user, an understanding amount of the user, a stress amount of the user, and a memorization amount of the user. The biometric information may include a biometric signal sensed from the user, such as a brainwave, a heart rate, and a movement of a pupil. A content providing method according to an embodiment of the present invention will now be described by illustrating a brainwave as the biometric information.

The device 100 according to an embodiment of the present invention may change content, based on the learning state of the user. The device 100 may change the content and efficiently provide information included in the content to the user. Based on a learning state of the user while at least one piece of sub-content included in the content is being output, the device 100 may determine at least one of a learning state regarding the output sub-content and a learning state regarding sub-content that is to be output in the future.

The device 100 according to an embodiment of the present invention may determine whether to change the content, by comparing the learning state of the user with a preset threshold for the content. The preset threshold may represent at least one of a concentration amount, an understanding amount, a stress amount, and a memorization amount required by the user to learn the content. When the learning state of the user does not correspond to the preset threshold, the device 100 may change the content.

When the learning state of the user does not satisfy the threshold required to learn the content, the device 100 according to an embodiment of the present invention may change the content to correspond to the learning state of the user. For example, the device 100 may change sub-content or an object included in the content to other sub-content or another object. As another example, the device 100 may change the content by selecting some of the at least one piece of sub-content included in the content. As another example, the device 100 may change a layout of the at least one piece of sub-content included in the content. However, this is only an embodiment of the present invention, and the method in which the user 100 changes the content is not limited thereto.

The device 100 according to an embodiment of the present invention may be realized in various types. For example, the device 100 may be, but is not limited to, a smartphone, a laptop computer, a tablet personal computer (PC), an e-book terminal, a digital broadcasting terminal, a personal digital assistant (PDA), a portable multimedia player (PMP), a navigation, a smart TV, a consumer electronics (CE) apparatus (e.g., a refrigerator and an air-conditioner each including a display panel), a head mounted display (HMD), or the like.

The sensing device 10 according to an embodiment of the present invention may be connected to the device 100 via short-range wireless communication. At this time, the sensing device 10 may receive a control command (for example, a biometric information request command) from the device 100 via the short-range wireless communication. In addition, the sensing device 10 may transmit input/output data (for example, biometric information) to the device 100 via the short-range wireless communication.

The sensing device 10 according to an embodiment of the present invention may include a Bluetooth Low Energy (BLE) module and/or a Near Field Communications (NFC) module. The sensing device 10 may receive a connection request from the device 100 via BLE and/or NFC and may activate a WiFi module or a Bluetooth module.

The sensing device 10 may be realized in various types. The sensing device 10 according to an embodiment of the present invention may include an input device, an output device, a control device, and the like. Examples of the sensing device 10 may include, are not limited to, a smart watch, smart glasses, a Bluetooth headphone, and a HMD. Examples of the sensing device 10 may further include, but are not limited to, biosensors, such as an electroencephalogram (EEG) sensor, a pulse wave sensor, and an electrocardiogram (ECG) sensor.

Figure 2:
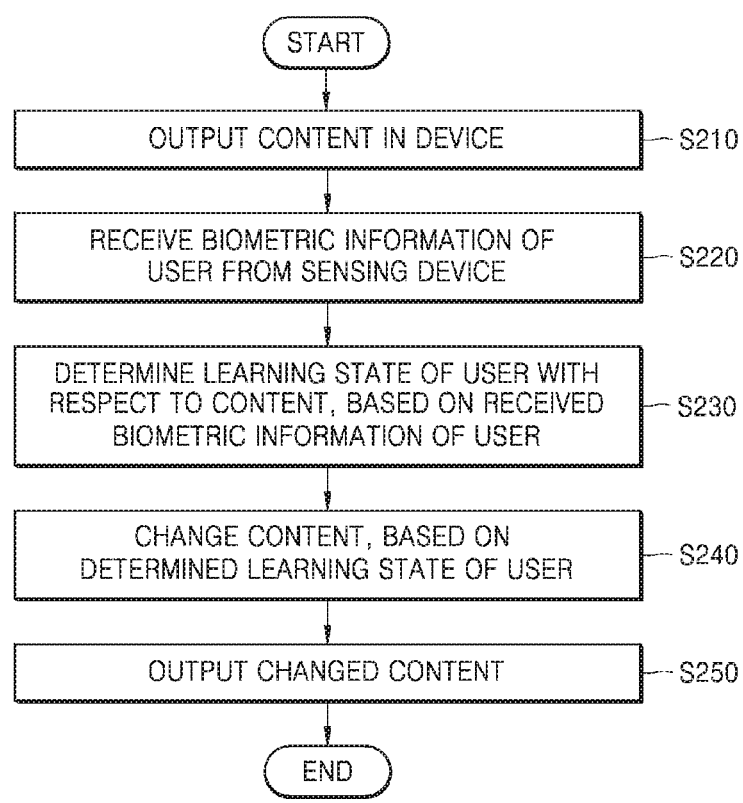
FIG. 2 is a flowchart of a method in which the device provides content, according to an embodiment of the present invention.

FIG. 2 is a flowchart of a method in which the device 100 provides content, according to an embodiment of the present invention.

In operation S210, the device 100 outputs the content.

The device 100 according to an embodiment of the present invention may store at least one piece of content. The device 100 may select one of the stored at least one piece of content, based on an input of a user. The device 100 may output the selected content.

As another example, the device 100 may receive at least one piece of content from an external device, by streaming. The device 100 may receive and output the content selected based on the input of the user, by streaming.

In operation S220, the device 100 receives biometric information of the user from the sensing device 10.

The device 100 according to an embodiment of the present invention may be connected to the sensing device 10 via wired and/or wireless communication. In particular, the device 100 according to an embodiment of the present invention may be connected to the sensing device 10 via short-range wireless communication. Examples of the short-range wireless communication may include, but are not limited to, Wi-Fi, NFC, Bluetooth, BLE, ZigBee, Wi-Fi Direct (WFD), and ultra wideband (UWB).

The device 100 may request the sensing device 10 for the biometric information of the user. When content is selected, the device 100 may request the sensing device 10 for brainwave information of the user. When output of some of pieces of sub-content included in the selected content is completed, the device 100 may request the sensing device 10 for biometric information of the user sensed while the some pieces of sub-content are being output. The device 100 may receive the biometric information of the user from the sensing device 10 in response to the request.

As another example, the device 100 may receive the biometric information of the user from the sensing device 10 at preset regular intervals. For example, the device 100 may receive the biometric information of the user from the sensing device 10 at intervals of 5 minutes.

However, this is merely an embodiment of the present invention. As another example, the device 100 may obtain the biometric information of the user from the sensor included in the device 100.

In operation S230, the device 100 determines a learning state of the user, based on the received biometric information of the user.

The device 100 according to an embodiment of the present invention may determine at least one of a concentration amount, an understanding amount, a stress amount, and a memorization amount of the user, based on the received biometric information of the user. For example, based on brainwave information of the user obtained while the some pieces of sub-content of the selected content are being output, the device 100 may determine a concentration degree, an understanding degree, and a stress degree of the user with respect to the output some pieces of sub-content. The device 100 may determine the concentration amount, the understanding amount, the stress amount, and the memorization amount by using at least one of the determined concentration degree, the determined understanding degree, and the determined stress degree.

The device 100 according to an embodiment of the present invention may determine a learning state of the user with respect to other sub-content of content that is to be used in the future, based on the brainwave information of the user obtained while the some pieces of sub-content of the selected content are being output. As another example, the device 100 may determine a learning state of the user with respect to some pieces of sub-content of already-used content.

In operation S240, the device 100 changes the content, based on the determined learning state of the user.

The device 100 may previously store information about a threshold representing a learning state of the user required to learn content. The threshold is a condition necessary for the user to learn the information included in the content, and may be at least one of a preset concentration amount, a preset understanding amount, a preset stress amount, and a preset memorization amount. Throughout the specification, the value of the threshold will be described in the unit of a point. The point may a result of normalizing data about at least one of a size, a waveform, and a pattern of the brainwave information of the user and representing the normalized data as an integer. For example, a concentration amount threshold for an English video lecture may be 50 points.

The device 100 may compare the learning state of the user with a threshold for the selected content. When the learning state of the user does not correspond to the threshold, the device 100 according to an embodiment of the present invention may change at least one piece of sub-content included in the selected content.

For example, when the learning state of the user does not correspond to the threshold, the device 100 may change the selected content by selecting some of the pieces of sub-content included in the selected content. As another example, the device 100 may change the selected content by adding sub-content included in other content to sub-content included in the selected content. However, this is only an embodiment, and the method of changing the content is not limited thereto.

In operation S250, the device 100 may output changed content. The device 100 according to an embodiment of the present invention may output metadata about at least one piece of sub-content included in the changed content, together with the changed content. For example, when the device 100 changes the selected English video lecture by selecting the lectures of 5 units from among the lectures of 10 units included in the selected English video lecture, the device 100 may output the titles of the selected lectures of the 5 units together with the changed content. As another example, the device 100 may output information about a time period taken until output of the changed content is completed, together with the changed content.

The aforementioned example is merely an embodiment of the present invention, and the device 100 may output only the changed content.

Figure 3:
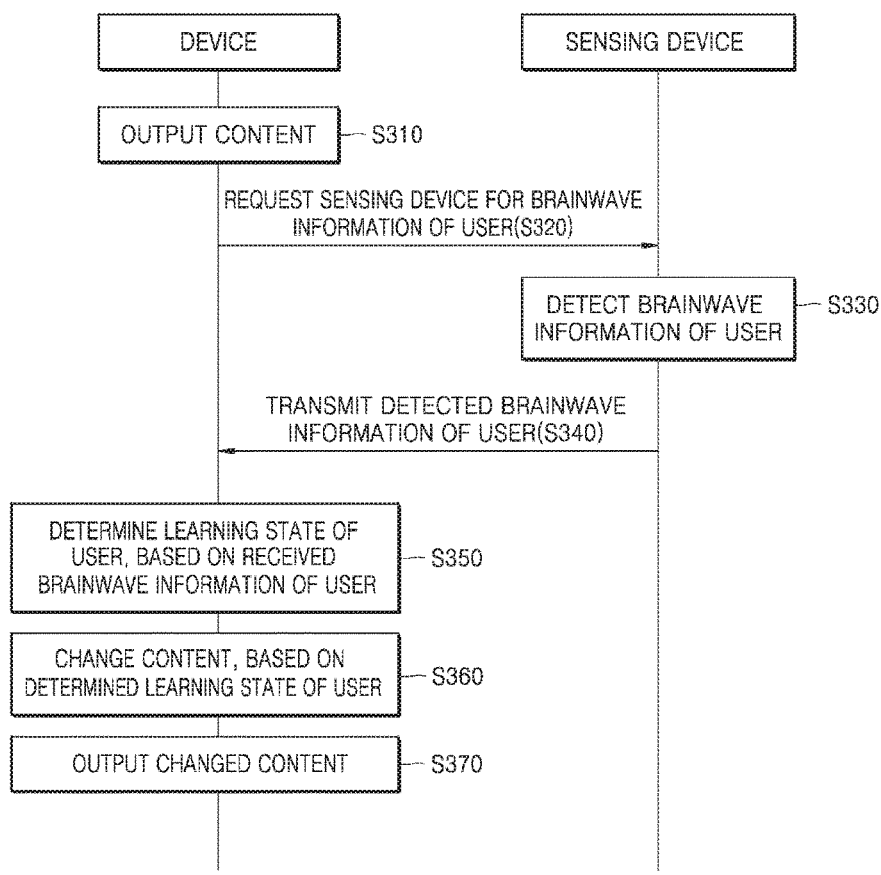
FIG. 3 is a diagram for explaining a method in which the device receives brainwave information of a user from a sensing device, according to an embodiment of the present invention.

FIG. 3 is a diagram for describing a method in which the device 100 receives brainwave information of a user from the sensing device 10, according to an embodiment of the present invention.

In operation S310, the device 100 may output content. Operation S310 may correspond to operation S210 described above with reference to FIG. 2.

In operation S320, as content is selected, the device 100 may request the sensing device 10 for the brainwave information of the user.

The device 100 according to an embodiment of the present invention may transmit a signal requesting the sensing device 10 connected to the device 100 for the brainwave information of the user. The signal that requests the brainwave information may include, for example, authentication information representing that the device 100 is a device of the user.

In operation S330, the sensing device 10 may detect the brainwave information of the user.

The sensing device 10 according to an embodiment of the present invention may detect the brainwave information of the user as the sensing device 10 receives the signal for requesting the brainwave information from the device 100. For example, the sensing device 10 may detect the brainwave information of the user from an EEG sensor included therein.

As another example, when the sensing device 10 has previously detected the brainwave information of the user, the sensing device 10 may select a portion of the pre-detected brainwave information. For example, the sensing device 10 may detect brainwave information previously detected within a certain time period range from the moment when the sensing device 10 receives the signal for requesting the brainwave information.

In operation S340, the sensing device 10 may transmit the detected brainwave information of the user to the device 100. For example, the sensing device 10 may transmit the brainwave information of the user to the device 100 via short-range wireless communication, such as WiFi or Bluetooth. However, this is only an embodiment, and the method of communication between the device 100 and the sensing device 10 is not limited thereto.

In operation S350, the device 100 may determine a learning state of the user, based on the received brainwave information of the user. The device 100 according to an embodiment of the present invention may determine at least one of a concentration amount, an understanding amount, a stress amount, and a memorization amount of the user, based on the received brainwave information of the user.

Operation S350 may correspond to operation S230 described above with reference to FIG. 2.

In operation S360, the device 100 may change sub-content included in the content, based on the determined learning state of the user. The device 100 according to an embodiment of the present invention may change at least one piece of sub-content included in the content. As another example, the device 100 may add at least one piece of sub-content included in other content to the at least one piece of sub-content included in the content.

Operation S360 may correspond to operation S240 described above with reference to FIG. 2.

In operation S370, the device 100 may output changed content. Operation S370 may correspond to operation S250 described above with reference to FIG. 2.

Figure 4:
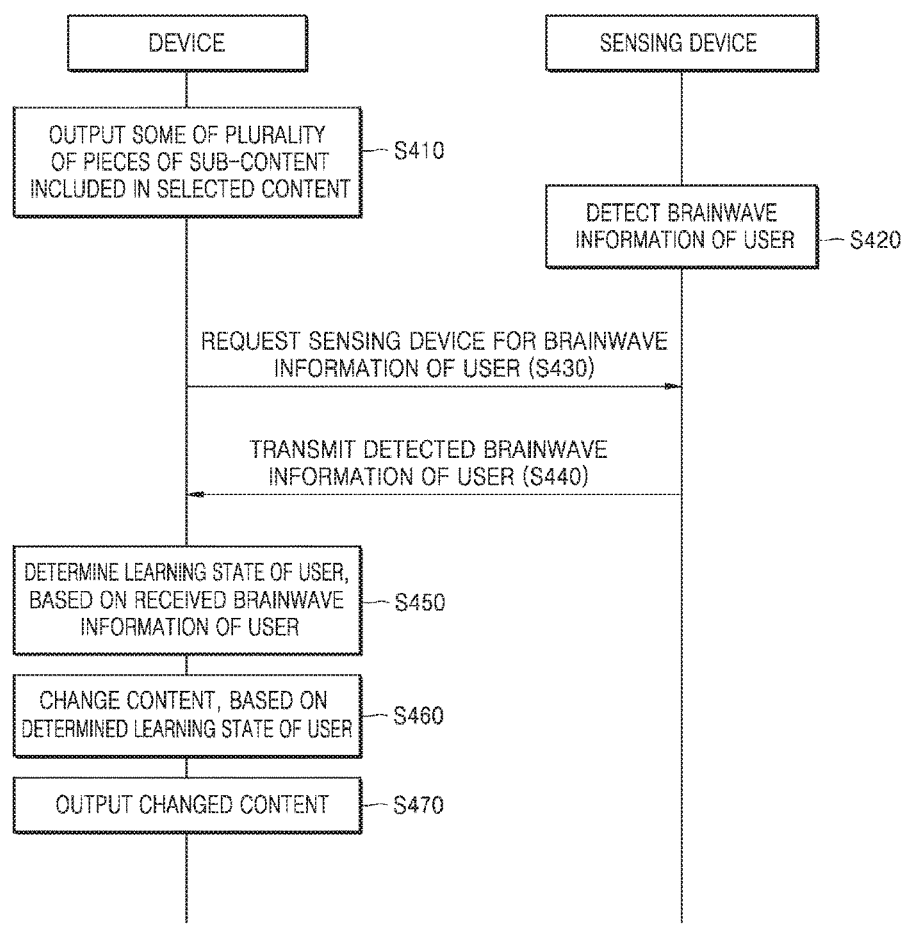
FIG. 4 is a diagram for explaining a method in which the device receives brainwave information of a user from a sensing device, according to another embodiment of the present invention.

FIG. 4 is a diagram for describing a method in which the device 100 receives brainwave information of a user from the sensing device 10, according to another embodiment of the present invention.

In operation S410, the device 100 may output some of a plurality of pieces of sub-content included in selected content. For example, the device 100 may output a lecture of a first unit in video content including respective English lectures of 5 units. As another example, the device 100 may output a first page from text content of 30 pages on which mathematical problems are displayed.

In operation S420, the sensing device 10 may detect brainwave information of the user while the device 100 is outputting the some pieces of sub-content. As the some pieces of sub-content are output, the device 100 according to an embodiment of the present invention may transmit a signal for representing output of the some pieces of sub-content to the sensing device 10. In response to the signal for representing output of the some pieces of sub-content, the sensing device 10 may detect the brainwave information of the user.

According to an embodiment of the present invention, the device 100 may more accurately determine a learning state of the user with respect to the content, by requesting the sensing device 10 to detect the brainwave information of the user while the some pieces of sub-content are being output.

In operation S430, the device 100 may request the sensing device 10 for the brainwave information of the user with respect to the output some pieces of sub-content.

According to an embodiment, the device 100 may request the sensing device 10 for brainwave information of the user with respect to output-completed sub-content every time output of each piece of sub-content is completed. According to another embodiment, the device 100 may request brainwave information of the user with respect to sub-content output during a preset unit time.

In operation S440, the sensing device 10 may transmit the detected brainwave information of the user to the device 100. For example, the sensing device 10 may transmit the brainwave information of the user to the device 100 via short-range wireless communication, such as WiFi or Bluetooth. However, this is only an embodiment, and the method of communication between the device 100 and the sensing device 10 is not limited thereto.

In operation S450, the device 100 may determine a learning state of the user, based on the received brainwave information of the user. The device 100 according to an embodiment of the present invention may determine at least one of a concentration amount, an understanding amount, a stress amount, and a memorization amount of the user, based on the received brainwave information of the user.

Operation S450 may correspond to operation S210 described above with reference to FIG. 2.

In operation S460, the device 100 may change the selected content according to the determined learning state of the user. The device 100 according to an embodiment of the present invention may change at least one piece of sub-content included in the selected content. As another example, the device 100 may change the selected content by combining at least one piece of sub-content included in the selected content with at least one piece of sub-content included in other content.

Operation S460 may correspond to operation S220 described above with reference to FIG. 2.

In operation S470, the device 100 may output changed content. Operation S470 may correspond to operation S230 described above with reference to FIG. 2.

Figure 5:
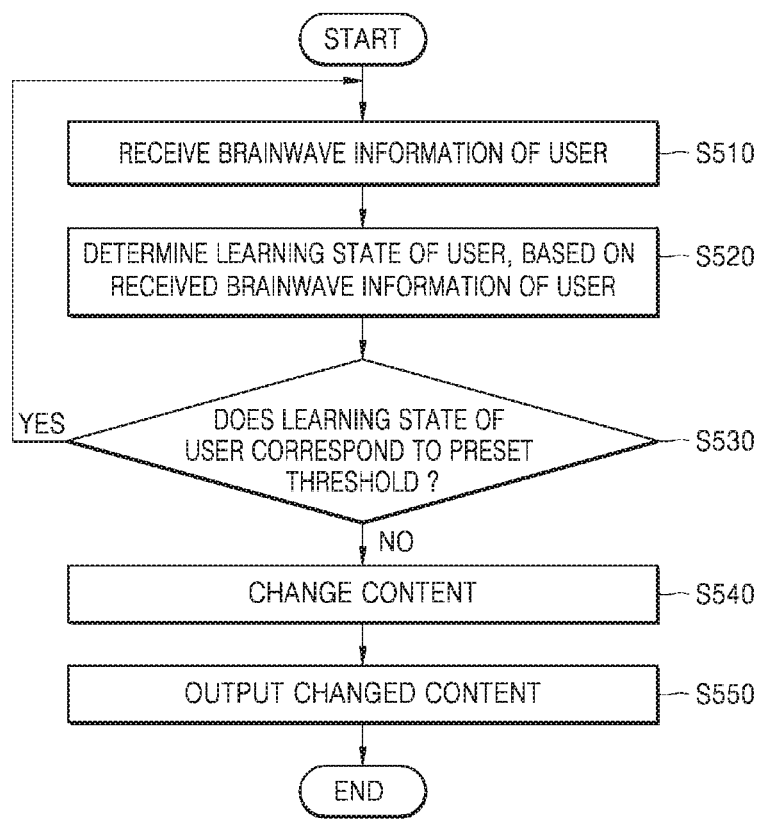
FIG. 5 is a flowchart of a method in which the device according to an embodiment of the present invention determines a learning state of a user, based on received brainwave information.

FIG. 5 is a flowchart of a method in which the device 100 according to an embodiment of the present invention determines a learning state of a user, based on received brainwave information.

In operation S510, the device 100 may receive brainwave information of the user. According to an embodiment of the present invention, the device 100 may receive the brainwave information of the user from the sensing device 10 connected to the device 100. However, the sensing device 10 is merely an embodiment of the present invention, and the device 100 may receive the brainwave information from another device including an EEG sensor capable of detecting the brainwave of the user.

In operation S520, the device 100 may determine a learning state of the user, based on the received brainwave information of the user. The brainwave information may include information about at least one of a plurality of types of brainwaves, such as an alpha wave, a gamma wave, a beta wave, and a sensor/motor rhythm (SMR) wave. However, this is merely an embodiment of the present invention, and the present invention is not limited thereto.

The device 100 according to an embodiment of the present invention may determine at least one of a concentration amount, an understanding amount, a stress amount, and a memorization amount of the user, based on the received brainwave information of the user.

The device 100 may allow the received brainwave information to pass through a filter and thus may detect brainwaves in a specific band capable of determining at least one of a concentration degree, an understanding degree, and a stress degree. For example, the device 100 may detect an SMR wave from the received brainwave information of the user.

The device 100 may determine the concentration degree, the understanding degree, and the stress degree, based on the waveform and size of the detected brainwave. For example, based on brainwave information detected while some pieces of sub-content included in selected content are being output, the device 100 may determine a concentration degree of the user while the some pieces of sub-content are being output. The device 100 according to an embodiment of the present invention may determine the concentration amount of the user by integrating the determined concentration degree of the user according to time. Herein, the device 100 may determine a concentration amount with respect to other sub-content of content that is to be used in the future. The device 100 may also determine a concentration amount with respect to some pieces of sub-content of already-used content.

As another example, based on the brainwave information detected while the some pieces of sub-content included in the selected content are being output, the device 100 may determine an understanding degree of the user while the some pieces of sub-content are being output. The device 100 according to an embodiment of the present invention may determine the understanding amount of the user by integrating the determined understanding degree of the user according to time. Herein, the device 100 may determine an understanding amount with respect to the other sub-content of the content that is to be used in the future. The device 100 may determine an understanding amount with respect to the some pieces of sub-content of the already-used content.

As another example, based on the brainwave information detected while the some pieces of sub-content included in the selected content are being output, the device 100 may determine a stress degree of the user while the some pieces of sub-content are being output. The device 100 according to an embodiment of the present invention may determine the stress amount of the user by integrating, according to time, a stress degree of a section that exceeds a preset limit stress degree. Herein, the device 100 may determine a stress amount with respect to the other sub-content of the content that is to be used in the future. The device 100 may also determine a stress amount with respect to the some pieces of sub-content of the already-used content.

As another example, the device 100 may determine a memorization amount, based on at least one of the concentration degree and the understanding degree of the user determined based on the brainwave information detected while the some pieces of sub-content are being output. Herein, the device 100 may determine a memorization amount with respect to the other sub-content of the content that is to be used in the future. The device 100 may also determine a memorization amount with respect to the some pieces of sub-content of the already-used content.

According to another embodiment of the present invention, the device 100 may determine the learning state of the user by comparing at least one of the size and the waveform of the brainwaves of the user with a pre-stored brainwave pattern. For example, the device 100 may detect a first brainwave pattern corresponding to the size and the waveform of the received brainwave, and may determine a concentration amount representing the detected first brainwave pattern as the concentration amount of the user.

In operation S530, the device 100 may determine whether the determined learning state of the user corresponds to a threshold.

The device 100 according to an embodiment of the present invention may compare the learning state of the user with a threshold required to use the selected content. Information about the threshold of the content may be pre-stored in memory of the device 100.

When the learning state of the user deviates from a threshold rang pre-set from the threshold, the device 100 may determine that the learning state of the user does not correspond to the threshold. For example, when the threshold is an understanding amount of 50 points and the threshold range is 3, the device 100 may determine that a learning state of the user of which an understanding amount does not correspond to one of 47 to 53 points does not correspond to the threshold.

As another example, when the learning state of the user corresponds to the threshold, the device 100 may output sub-content of the selected content. While the sub-content is being output, the device 100 may receive the brainwave information of the user from the sensing device 10.

The method in which the device 100 according to an embodiment of the present invention determines whether each of the concentration amount, the understanding amount, the stress amount, and the memorization amount of the user corresponds to the threshold for the selected content will be described in more detail later with reference to FIGS. 6-11.

In operation S540, when the determined learning state of the user does not correspond to the threshold, the device 100 may change the content.

The device 100 according to an embodiment of the present invention may change content by selecting some of a plurality of pieces of sub-content included in the content, based on the determined learning state of the user. The device 100 may also change the layout order of the plurality of pieces of sub-content included in the content. As another example, the device 100 may change at least one of the shapes, colors, and locations of objects included in each of the plurality of pieces of sub-content included in the content. As another example, the device 100 may change some of the plurality of pieces of sub-content included in the content to sub-content included in other content. The device 100 may add sub-content included in other content to the sub-content included in the selected content.

In operation S550, the device 100 may output changed content.

Operation S550 may correspond to operation S250 described above with reference to FIG. 2.

Figure 6:
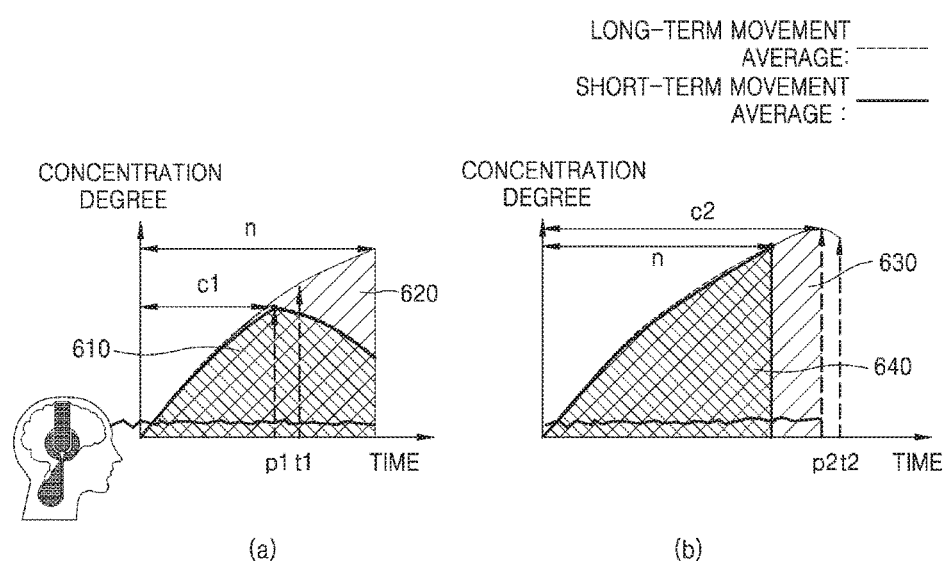
FIG. 6 illustrates graphs for describing a method in which the device according to an embodiment of the present invention determines a concentration amount of a user by using brainwave information of the user.

FIG. 6 illustrates graphs for describing a method in which the device 100 according to an embodiment of the present invention determines the concentration amount of the user by using the brainwave information of the user.

Referring to FIG. 6, the device 100 may determine the concentration amount of the user by using the brainwave information of the user. The concentration amount of the user may include at least one of a concentration amount with respect to already-output sub-content and a concentration amount with respect to sub-content that is to be output in the future, from among at least one piece of sub-content included in content.

The device 100 according to an embodiment of the present invention may detect a change, over time, in the waveform and the size of the SMR wave included in the brainwave information of the user. The SMR wave is an example of brainwaves used to determine the learning state of the user, and the present invention is not limited thereto. The device 100 may determine the learning state of the user by combining brainwaves in a specific band extracted from the brainwave information.

The device 100 may determine a short-term movement average value and a long-term movement average value for the concentration degree from the received SMR wave. The short-term movement average value and the long-term movement average value may be distinguished from each other according to a length of a section in which data (for example, the concentration degree) is sampled. For example, the device 100 may determine an average of 5 concentration degree values sampled from the SMR wave, as the short-term movement average value. The device 100 may also determine an average of 20 concentration degree values sampled from the SMR wave, as the long-term movement average value. The device 100 may determine sections c1 and c2 from a detection start point of the SMR wave to points p1 and p2 where the short-term movement average value and the long-term movement average value intersect, as optimal concentration periods. Referring to (a) of FIG. 6, the device 100 may determine a section from the detection point to the point p1 where the short-term movement average value and the long-term movement average value intersect, as the optimal concentration period c1.

In (a) of FIG. 6, a maximum concentration period necessary for the user to use the content output by the device 100 may be assumed to be n. The device 100 may integrate the concentration degree according to time and obtain a concentration amount threshold, during the maximum concentration period n for the content. In (a) of FIG. 6, a concentration amount threshold 620 will be described as na.

The device 100 according to an embodiment of the present invention may determine that a concentration amount 610 of the user does not correspond to the concentration amount threshold 620, because, at a time point t1 when the brainwave information is received, the optimal concentration period c1 of the user is less than the optimal concentration period n necessary for learning the content.

Referring to (b) of FIG. 6, the device 100 may determine a section from the detection point to the point p2 where the short-term movement average value and the long-term movement average value intersect, as the optimal concentration period c2.

In (b) of FIG. 6, a maximum concentration period necessary for the user to use the content output by the device 100 may be assumed to be n. In (b) of FIG. 6, a concentration amount threshold 640 for the content will be described as na, as in the case of (a) of FIG. 6.

The device 100 according to an embodiment of the present invention may determine that a concentration amount 630 of the user corresponds to the concentration amount threshold 640, because, at a time point t2 when the brainwave information is received, the optimal concentration period c2 of the user is equal to or greater than the optimal concentration period n necessary for learning the content.

Figure 7:
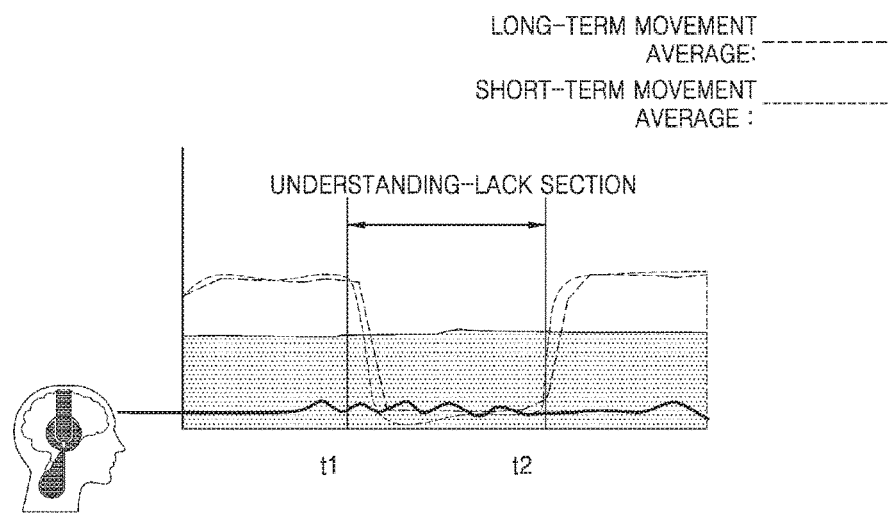
FIG. 7 illustrates graphs for describing a method in which the device according to an embodiment of the present invention determines an understanding amount of a user by using brainwave information of the user.

FIG. 7 is a graph for describing a method in which the device 100 according to an embodiment of the present invention determines the understanding amount of the user by using the brainwave information of the user.

Referring to FIG. 7, the device 100 may determine the understanding amount of the user by using the brainwave information of the user. The understanding amount of the user may include at least one of an understanding amount with respect to sub-content output from content and an understanding amount with respect to sub-content that is to be output from the content in the future.

The device 100 according to an embodiment of the present invention may detect a change, over time, in the waveform and the size of a mid-beta wave included in the brainwave information of the user. The device 100 according to an embodiment of the present invention may determine a short-term movement average value and a long-term movement average value for the understanding degree from the received mid-beta wave. For example, the device 100 may determine an average of 3 understanding degree values sampled from the mid-beta wave, as the short-term movement average value. The device 100 may also determine an average of 10 understanding degree values sampled from the mid-beta wave, as the long-term movement average value.

Referring to FIG. 7, the device 100 may determine that, as the understanding degree decreases, an understanding-lack section starts from a first point t1 where the short-term movement average value and the long-term movement average value intersect.

The device 100 may also determine a section from the first point t1 to a second point t2 where the short-term movement average value and the long-term movement average value intersect again, as an understanding-lack period.

Referring to FIG. 7, the device 100 may determine that an understanding amount of the user for the output sub-content of the content is lack during the understanding-lack period from the first point t1 to the second point t2.

Figure 8:
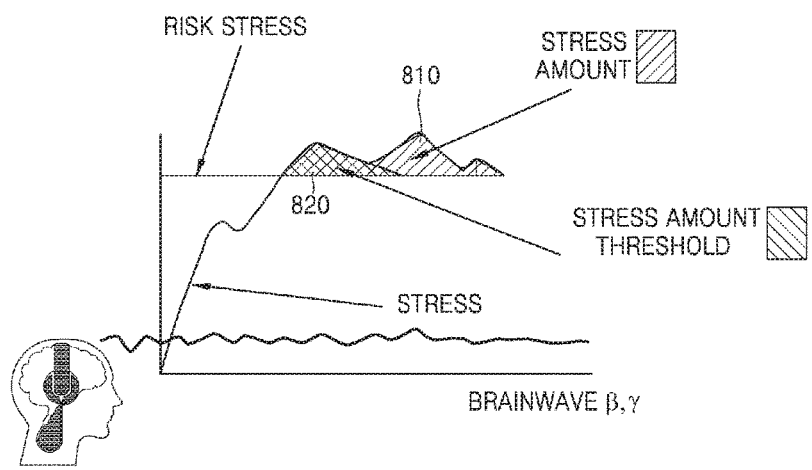
FIG. 8 illustrates graphs for describing a method in which the device according to an embodiment of the present invention determines a stress amount of a user by using brainwave information of the user.

FIG. 8 is a graph for describing a method in which the device 100 according to an embodiment of the present invention determines the stress amount of the user by using the brainwave information of the user.

Referring to FIG. 8, the device 100 may determine the stress amount of the user by using the brainwave information of the user. The stress amount of the user may include at least one of a stress amount with respect to sub-content already output from content and a stress amount with respect to sub-content that is to be output from the content in the future.

The device 100 according to an embodiment of the present invention may detect a change, over time, in the waveforms and the sizes of a beta wave and a gamma wave included in the brainwave information of the user.

The device 100 according to an embodiment of the present invention may determine whether a stress degree determined from a received beta wave and a received gamma wave exceeds a preset risk stress threshold. The risk stress threshold may be set differently according to users.

The device 100 may determine the stress amount by integrating a stress degree in a section that exceeds the risk stress threshold. The device 100 may determine whether a determined stress amount 810 exceeds a stress amount threshold 820 allowed for the user to obtain information of the content. The stress amount threshold 820 may be set differently according to users. In FIG. 8, the device 100 may determine that the determined stress amount 810 of the user exceeds the stress amount threshold 820.

Figure 9:
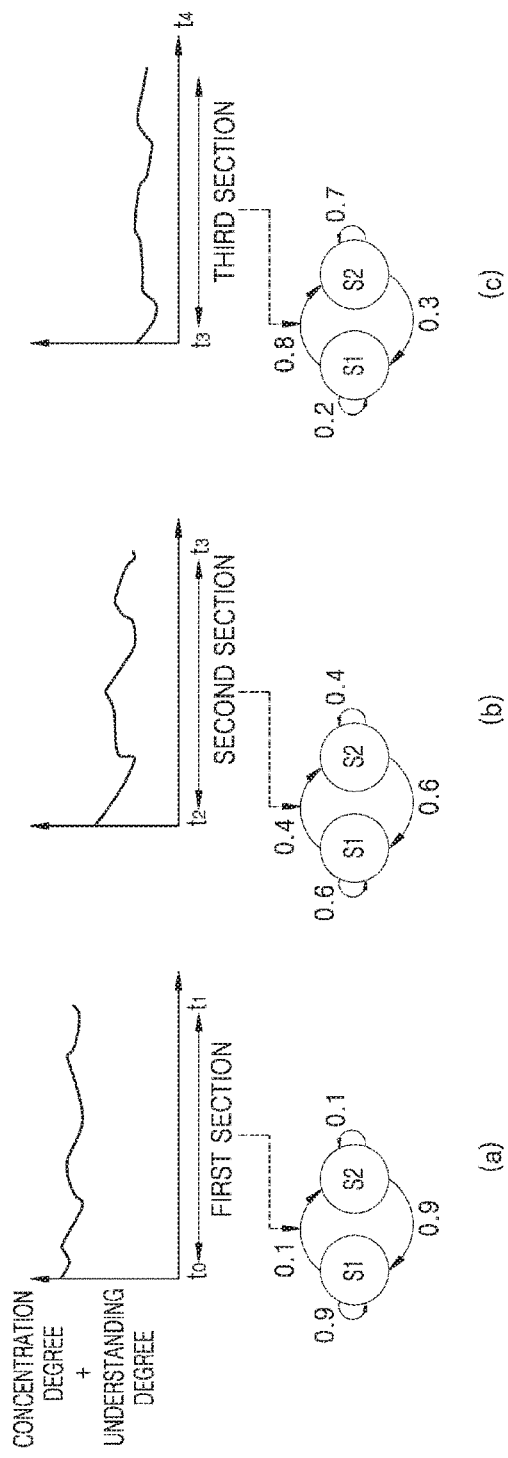
FIG. 9 illustrates graphs for describing a method in which the device determines a memorization amount of a user, based on brainwave information of the user, according to an embodiment of the present invention.

FIG. 9 illustrates graphs for describing a method in which the device 100 determines the memorization amount of the user, based on the brainwave information of the user, according to an embodiment of the present invention.

FIG. 9 illustrates a plurality of state diagrams determined based on a change, over time, in the concentration degree and the understanding degree of the user. The probability that the learning state of the user is determined as each of states S1 and S2 included in the state diagrams may vary according to changes, over time, in the concentration degree or the understanding degree of the user.

In FIG. 9, the state S1 represents a case where the memorization amount of the user corresponds to a memorization amount threshold for content. The state S2 represents a case where the memorization amount of the user does not correspond to the memorization amount threshold for the content.

For example, in (a) of FIG. 9, based on a change in the concentration degree and the understanding degree of the user, the device 100 may determine that the probability that the state of the user is maintained as the state S1 is 0.9, the probability that the state of the user changes from the state S1 to the state S2 is 0.1, the probability that the state of the user changes from the state S2 to the state S2 is 0.9, and the probability that the state of the user is maintained as the state S2 is 0.1. On the other hand, in (b) of FIG. 9, based on a change in the concentration degree and the understanding degree of the user, the device 100 may determine that the probability that the state of the user is maintained as the state S1 is 0.6, the probability that the state of the user changes from the state S1 to the state S2 is 0.4, the probability that the state of the user changes from the state S2 to the state S2 is 0.6, and the probability that the state of the user is maintained as the state S2 is 0.4. On the other hand, in (c) of FIG. 9, based on a change in the concentration degree and the understanding degree of the user, the device 100 may determine that the probability that the state of the user is maintained as the state S1 is 0.2, the probability that the state of the user changes from the state S1 to the state S2 is 0.8, the probability that the state of the user changes from the state S2 to the state S2 is 0.3, and the probability that the state of the user is maintained as the state S2 is 0.7.

The device 100 may more accurately determine whether the memorization amount of the user with respect to the content corresponds to the memorization amount threshold, by resetting the state diagrams according to the concentration degree and the understanding degree determined based on the received brainwave information of the user.

Figure 10:
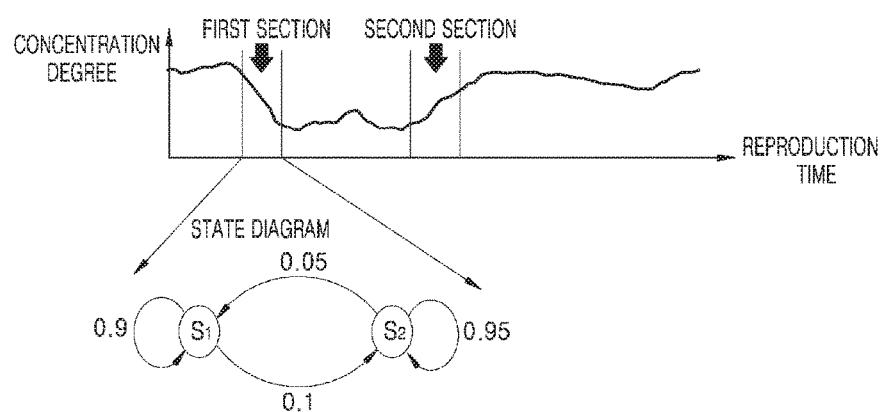
FIG. 10 illustrates graphs for describing a method in which the device determines a memorization amount of a user, based on brainwave information of the user, according to another embodiment of the present invention.

FIG. 10 is a graph for describing a method in which the device 100 determines the memorization amount of the user, based on the brainwave information of the user, according to another embodiment of the present invention.

Referring to FIG. 10, the device 100 may determine a state diagram for determining the memorization amount of the user based on the concentration degree of the user.

The device 100 according to an embodiment of the present invention may extract an SMR wave representing the concentration degree, from the received brainwave information. The device 100 may determine a change in the concentration degree over time from the extracted SMR wave. Based on a change in the concentration degree of the user in a first section, the device 100 may determine the probability that the state of the user is maintained as the state S1, the probability that the state of the user changes from the state S1 to the state S2, the probability that the state of the user changes from the state S2 to the state S2, and the probability that the state of the user is maintained as the state S2. As described above with reference to FIG. 9, the states S1 and S2 respectively represent a case where the memorization amount of the user corresponds to the memorization amount threshold for the content and a case where the memorization amount of the user does not correspond to the memorization amount threshold for the content.

The state diagram of the user may change according to the concentration degree of the user. For example, in a second section, as the concentration degree of the user changes differently from the first section, a state diagram having a different value from the state diagram for the first section may be determined. The device 100 according to an embodiment of the present invention may determine a maximum memorization degree of the user, based on the determined state diagram of the user. This will now be described in greater detail with reference to FIG. 11.

Figure 11:
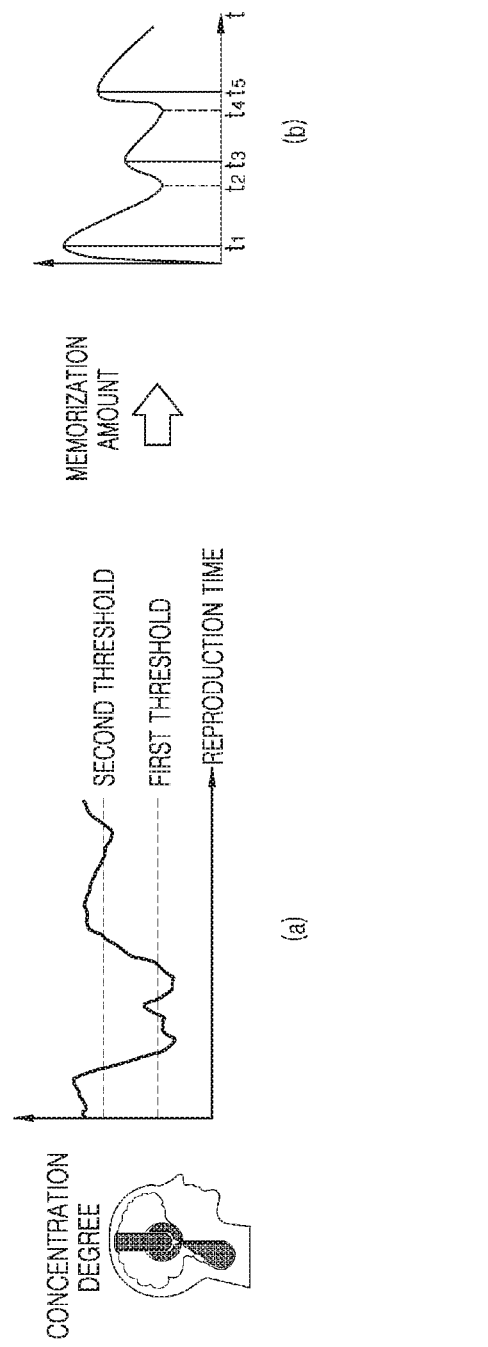
FIG. 11 illustrates graphs for describing a method in which the device determines a memorization amount of a user, based on brainwave information of the user, according to another embodiment of the present invention.

FIG. 11 illustrates graphs for describing a method in which the device 100 according to an embodiment of the present invention determines the maximum memorization amount of the user, based on the brainwave information of the user.

Referring to FIG. 11, the device 100 may determine a memorization amount of the user over time, based on the brainwave information of the user.

The device 100 according to an embodiment of the present invention may extract a concentration degree of the user from a received SMR wave and a received mid-beta wave. The device 100 may also determine a forgetting curve representing the memorization amount of the user, from the determined concentration degree. The device 100 may predict a point where the memorization amount drops to a preset memorization amount threshold or less, from the determined forgetting curve.

The device 100 according to an embodiment of the present invention may determine the maximum memorization amount of the user from the forgetting curve, based on the brainwave information of the user. The maximum memorization amount may be determined according to the state diagrams of the user described above with reference to FIGS. 9 and 10. For example, as a value of the concentration degree determined based on the brainwave information of the user increases, the maximum memorization amount of the user may increase. Referring to FIG. 10, in the forgetting curve, memorization amounts at time points t1, t3, and t5 may represent maximum memorization amounts of the user.

The device 100 may predict the point where the memorization amount drops to the preset memorization amount threshold or less, based on the maximum memorization amounts. For example, referring to FIG. 9, the device 100 may predict that memorization amounts at time points t2 and t4 drop to the preset memorization amount threshold or less.

According to another embodiment, the device 100 may predict a point where a memorization amount for sub-content drops to the preset memorization amount threshold or less, by taking into account the levels of difficulty and importance of the sub-content and the forgetting curve of the user.

Figure 12:
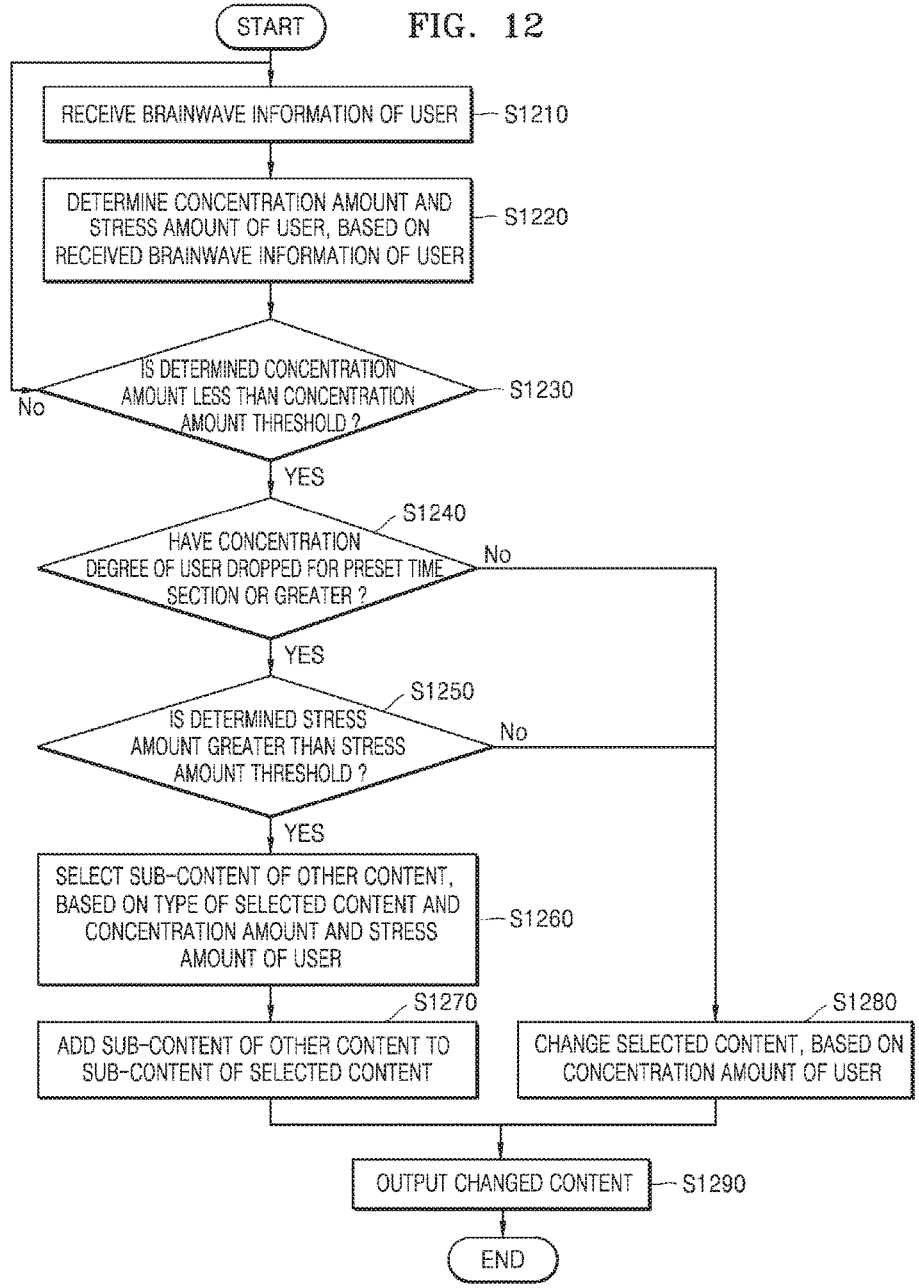
FIG. 12 is a flowchart of a method in which the device according to an embodiment of the present invention changes content according to a concentration amount and a stress amount of a user.

FIG. 12 is a flowchart of a method in which the device 100 according to an embodiment of the present invention changes content according to the concentration amount and the stress amount of the user.

In operation S1210, the device 100 may receive the brainwave information of the user. When one of a plurality of pieces of content is selected, the device 100 according to an embodiment of the present invention may receive the brainwave information of the user from the sensing device 10. As another example, when some pieces of sub-content included in content selected from a plurality of pieces of content are output, the device 100 may receive the brainwave information of the user from the sensing device 10.

In operation S1220, the device 100 may determine the concentration amount and the stress amount of the user, based on the received brainwave information of the user.

The method in which the device 100 determines the concentration amount of the user from the received brainwave information may correspond to the method described above with reference to FIG. 6. The method in which the device 100 determines the stress amount of the user from the received brainwave information may correspond to the method described above with reference to FIG. 8.

In operation S1230, the device 100 may compare the determined concentration amount with a preset concentration amount threshold for the selected content. For example, the device 100 may compare a concentration amount threshold of 100 points necessary for using video content including respective English lectures of 10 units with a concentration amount of the user with respect to the video content. As another example, when English lectures for three units are output from the video content including the English lectures of 10 units, the device 100 may compare a concentration amount threshold of 70 points necessary for using respective English lectures of the remaining 7 units with the concentration amount of the user with respect to the video content.

When the concentration amount of the user is equal to or greater than the concentration amount threshold, the device 100 may output sub-content of the selected content. While the sub-content is being output, the device 100 may receive the brainwave information of the user from the sensing device 10.

In operation S1240, the device 100 may determine whether the concentration degree of the user has dropped for a preset section or greater. When the concentration amount of the user is less than the concentration amount threshold, the device 100 according to an embodiment of the present invention may determine whether the concentration degree of the user has dropped for the preset section or greater.

In operation S1250, the device 100 may compare the determined stress amount with a stress amount threshold.

When the concentration degree of the user has dropped for the preset section or greater, the device 100 according to an embodiment of the present invention may compare the determined stress amount with the stress amount threshold.

For example, the device 100 may compare a stress amount threshold of 70 points for the video content including the respective English lectures of 10 units, with a stress amount of the user with respect to the video content. As another example, when English lectures for three units are output from the video content including the respective English lectures of 10 units, the device 100 may compare a stress amount threshold of 40 points necessary for using respective English lectures of the remaining 7 units with the stress amount of the user with respect to the video content.

In operation S1260, when the stress amount of the user exceeds the stress amount threshold, the device 100 may select other content capable of reducing the stress amount of the user, based on the type of selected content and the concentration amount and the stress amount of the user. For example, the device 100 may select a music playback application or a game application.

Alternatively, the device 100 may select content suitable for the type of selected content from among a plurality of pieces of other content. Information about the other content suitable for the selected content may be pre-stored in the memory of the device 100. For example, when the selected content is a digital book including mathematical problems, the device 100 may select a music playback application according to the information pre-stored in the memory.

The device 100 may select one of a plurality of pieces of content, based on the concentration amount and the stress amount of the user. For example, when the stress amount of the user is higher than the stress amount threshold by no less than a certain range, the device 100 may select other content that greatly decreases the stress amount, even when the concentration amount decreases.

In operation S1270, the device 1000 may change the selected content by adding sub-content of the other content to the sub-content of the selected content.

The device 100 according to an embodiment of the present invention may determine a time point and a time length when the sub-content of the other content is output, based on the concentration amount and the stress amount of the user. As another example, the device 100 may add sub-content of the other content to all of the pieces of sub-contents of the selected content. For example, the device 100 may add sub-content of the other content to between first sub-content and second sub-content of the selected content.

In operation S1280, the device 100 may change the selected content, based on the concentration amount of the user. When the concentration degree of the user does not drop for the preset section or greater and the stress amount is less than or equal to the stress amount threshold, the device 100 may change at least one of a plurality of pieces of sub-content included in the selected content. When the concentration degree of the user does not drop for the preset section or greater and the stress amount is less than or equal to the stress amount threshold, the device 100 may determine that a lack of the concentration amount of the user results in the user failing to learn all of the plurality of pieces of sub-content included in the selected content. Accordingly, the device 100 may select some of the plurality of pieces of sub-content included in the content. However, this is only an embodiment of the present invention, and the method of changing the content when the concentration amount of the user is less than the concentration amount threshold is not limited thereto.

As another example, the device 100 may change the selected content by changing the layout order of the plurality of pieces of sub-content included in the selected content. As another example, the device 100 may change at least one of the shapes, colors, and locations of objects included in the plurality of pieces of sub-content of the selected content.

In operation S1290, the device 100 may output changed content.

Operation S1290 may correspond to operation S250 described above with reference to FIG. 2.

The method described above with reference to FIG. 12 in which the device 100 changes the content based on the concentration amount and the stress amount is merely an embodiment of the present invention, and the device 100 may change content based on at least one of the concentration amount, the stress amount, the understanding amount, and the memorization amount.

Figure 13:
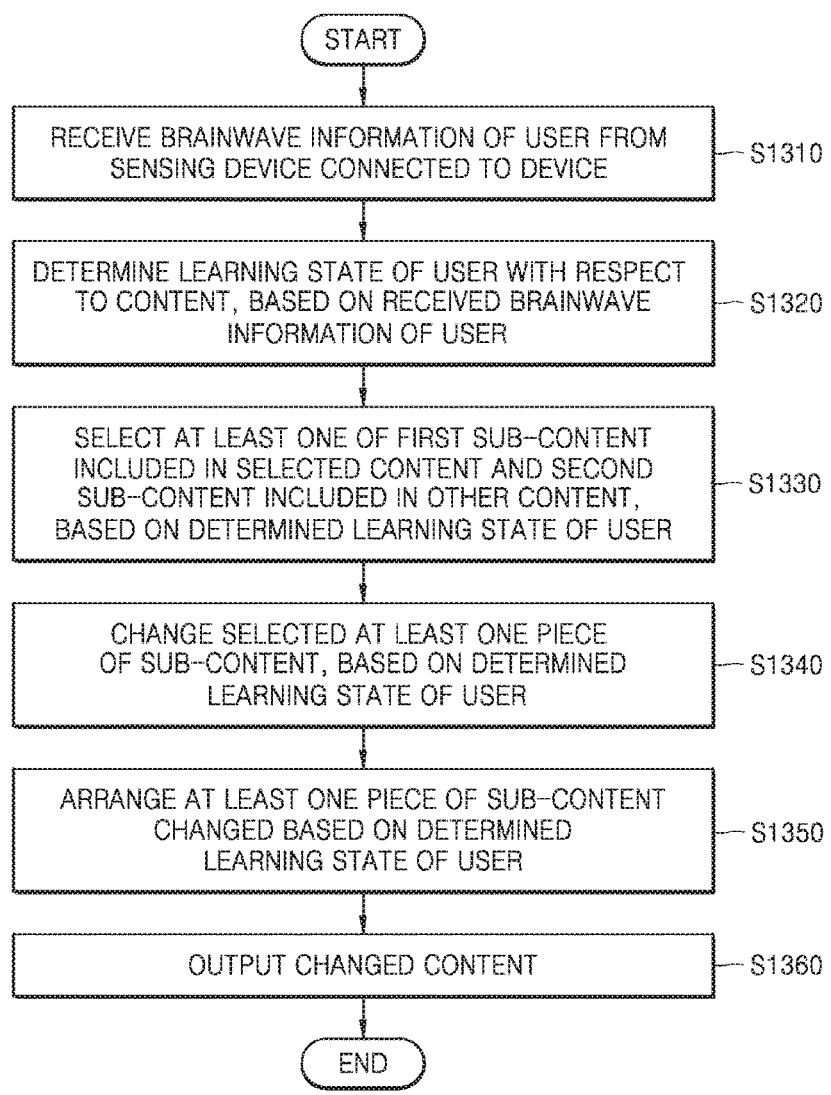
FIG. 13 is a flowchart of a method in which the device changes selected content, based on brainwave information of a user, according to an embodiment of the present invention.

FIG. 13 is a flowchart of a method in which the device 100 changes selected content, based on the brainwave information of the user, according to an embodiment of the present invention.

In operation S1310, the device 100 may receive the brainwave information of the user from the sensing device 10 connected to the device 100.

According to an embodiment of the present invention, the device 100 may receive brainwave information of the user obtained by using some pieces of sub-content of content selected according to an input of the user. For example, the device 100 may receive brainwave information of the user who took a lecture of a first unit in an English video lecture.

According to another embodiment, when content is selected according to an input of the user, the device 100 may receive the brainwave information of the user from the sensing device 10 before the content is output. For example, when an English video lecture is selected according to an input of the user, the device 100 may request the sensing device 10 for brainwave information of the user. Before the English video lecture is output, the device 100 may receive brainwave information of the user detected by the sensing device 10 from the sensing device 10.

In operation S1320, the device 100 may determine a learning state of the user with respect to the selected content, based on the received brainwave information of the user.

When the device 100 according to an embodiment of the present invention has output some pieces of sub-content included in the content, the device 100 may determine a learning state of the user with respect to not-output pieces of sub-content. For example, when the user has taken the lecture of the first unit from the English video lecture, the device 100 may determine at least one of a concentration amount, an understanding amount, a stress amount, and a memorization amount of the user with respect to second and third units that are not output.

According to another embodiment, the device 100 may determine the learning state of the user with respect to the output some pieces of sub-content. For example, when the user has taken the lecture of the first unit from the English video lecture, the device 100 may determine at least one of a concentration amount, an understanding amount, a stress amount, and a memorization amount of the user with respect to the output first unit.

When the user does not use the selected content, the device 100 may determine a learning state of the user with respect to all of the pieces of sub-content included in the selected content. For example, the device 100 may determine at least one of a concentration amount, an understanding amount, a stress amount, and a memorization amount of the user with respect to the first, second, and third units included in the selected English video lecture.

In operation S1330, based on the determined learning state of the user, the device 100 may select at least one of first sub-content included in the selected content and second sub-content included in other content.

When the determined learning state of the user does not correspond to a threshold necessary for learning the selected content, the device 100 according to an embodiment of the present invention may select a portion of the first sub-content included in the selected content. For example, when the device 100 determines that the determined concentration amount of the user is less than a concentration amount threshold necessary for learning the lectures of the second and third units included in the English video lecture, the device 100 may select only the lecture of the second unit.

According to another embodiment, when the determined learning state of the user does not correspond to the threshold necessary for learning the selected content, the device 100 may select the first sub-content included in the selected content and the second sub-content included in the other content. For example, when the concentration amount of the user is less than a concentration amount threshold necessary for learning the English video lecture and the stress amount of the user is greater than a stress amount threshold, the device 100 may select the lecture of the second unit included in the English video lecture and a first mp3 sound source included in a music application.

In operation S1340, the device 100 may change the selected at least one piece of sub-content, based on the determined learning state of the user. For example, the device 100 may change at least one of the shapes, colors, and locations of objects included in the selected at least one piece of sub-content. The objects may include at least one of a frame, image data, text data, and audio data.

According to an embodiment of the present invention, the device 100 may change at least one of a frame, image data, text data, and audio data included in the selected first sub-content. For example, the device 100 may change a location of a frame included in the lecture of the second unit included in the English video lecture. As another example, the device 100 may change at least one of a shape, a color, and a location of text data included in a page of a digital textbook. As another example, the device 100 may change an output location of audio data included in an English recording file.

The device 100 may set a bookmark for the objects included in the selected first sub-content. The device 100 may change an output method, such as an output speed, an output frequency, and an output size, of the objects for which a bookmark was set, according to a preset method. For example, the display 100 may decrease or increase an output speed of specific frames. The device 100 may increase or decrease the sound of specific audio data and output a result.

According to another embodiment of the present invention, the device 100 may change at least one of a frame, image data, text data, and audio data included in both the selected first sub-content and the selected second sub-content. For example, when a scenery picture is selected as the second sub-content, the device 100 may change at least one a size, a color, and a shape of the scenery picture.

Operation S1340 may not be performed according to a learning state of the user. For example, the device 100 may determine that changing sub-content is not necessary, based on a threshold necessary for using the selected first sub-content of the selected content or the selected second sub-content of the other content and the learning state of the user. In this case, the device 100 may skip operation S1340 and may perform operation S1350.

In operation S1350, the device 100 may change the selected content by arranging the at least one piece of sub-content changed based on the determined learning state of the user.

The device 100 according to an embodiment of the present invention may change an output sequence of the selected first sub-content or the selected and changed first sub-content differently from a preset output sequence. For example, when the lectures of the second and third units are selected from the English video lecture, the device 100 may change an output sequence of the selected lectures. According to the determined understanding amount of the user, the device 100 may change an output sequence of the lectures such that the user may take the lecture of the third lecture earlier than the lecture of the second unit because the lecture of the third lecture is relatively easier than the lecture of the second unit.

According to another embodiment, the device 100 may arrange selected or selected and then changed at least one piece of first sub-content and selected or selected and then changed at least one piece of second sub-content. For example, the device 100 may arrange a meditation video between the lectures of the second and third units selected from the English video lecture. The device 100 may increase the concentration amount of the user by arranging another video between the lectures of the second and third units, which drop the concentration amount of the user.

In operation S1360, the device 100 may output changed content.

Operation S1360 may correspond to operation S250 described above with reference to FIG. 2.

Figure 14:
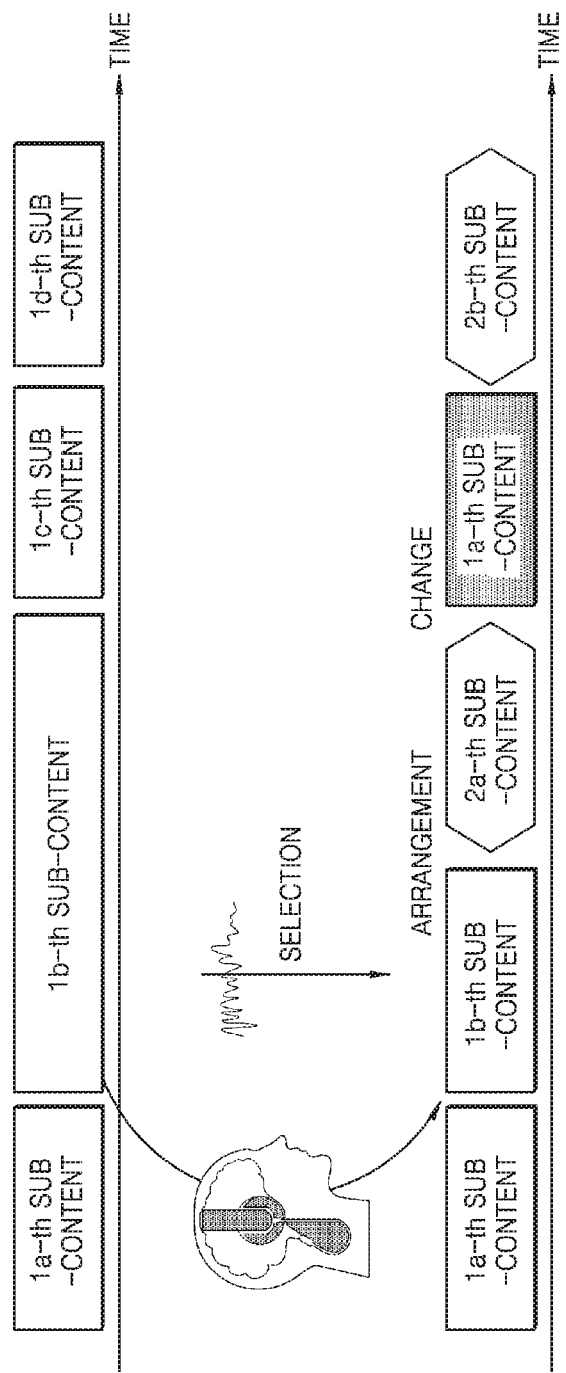
FIG. 14 is a schematic diagram for explaining a method in which the device receives brainwave information of a user who learned some pieces of sub-content of selected content, and changes the selected content, according to an embodiment of the present invention.

FIG. 14 is a schematic diagram for explaining a method in which the device 100 receives brainwave information of a user who learned some pieces of sub-content of selected content, and changes the selected content, according to an embodiment of the present invention.

Referring to FIG. 14, the content selected by the device 100 may include 1a-th sub-content, 1b-th sub-content, 1c-th sub-content, and 1d-th sub-content. When output of the 1a-th sub-content included in the selected content is completed, the device 100 according to an embodiment of the present invention may request the sensing device 10 for brainwave information of the user detected while the 1a-th sub-content is being output.

The device 100 may determine a learning state of the user with respect to the 1a-th sub-content output by the sensing device 10, based on the received brainwave information. As another example, the device 100 may determine learning states of the user with respect to the 1b-th sub-content, the 1c-th sub-content, and the 1d-th sub-content that are to be output in the future, based on the brainwave information received from the sensing device 10.

When the learning state of the user with respect to the 1a-th sub-content does not satisfy a preset threshold for the 1a-th sub-content, the device 100 may change the selected content. Also, when the learning states of the user determined for the 1b-th sub-content, the 1c-th sub-content, and the 1d-th sub-content do not satisfy respective preset thresholds for the 1b-th sub-content, the 1c-th sub-content, and the 1d-th sub-content, the device 100 may change the selected content.

In FIG. 14, the device 100 may select only the 1b-th sub-content from among the 1b-th sub-content, the 1c-th sub-content, and the 1d-th sub-content which are not yet output. The device 100 may select some pieces of sub-content according to a request by the user or the order of importance between pieces of sub-content included in metadata of the selected content. However, this is merely an embodiment, and the present invention is not limited thereto.

The device 100 may select only some objects from the objects that constitute the selected 1b-th sub-content, thereby reducing an output time period of the 1b-th sub-content. The device 100 may select 2a-th sub-content and 2b-th sub-content from content other than the 1b-th sub-content.

When the learning state of the user with respect to the previously-output 1a-th sub-content does not correspond to the preset threshold, the device 100 may repeatedly output the 1a-th sub-content.

Referring to FIG. 14, the device 100 may change the selected content by combining the changed 1b-th sub-content, the 2a-th sub-content and the 2b-th sub-content selected from the other content, and the previously-output 1a-th sub-content with each other according to the learning state of the user.

The device 100 may output changed content.

Figure 15:
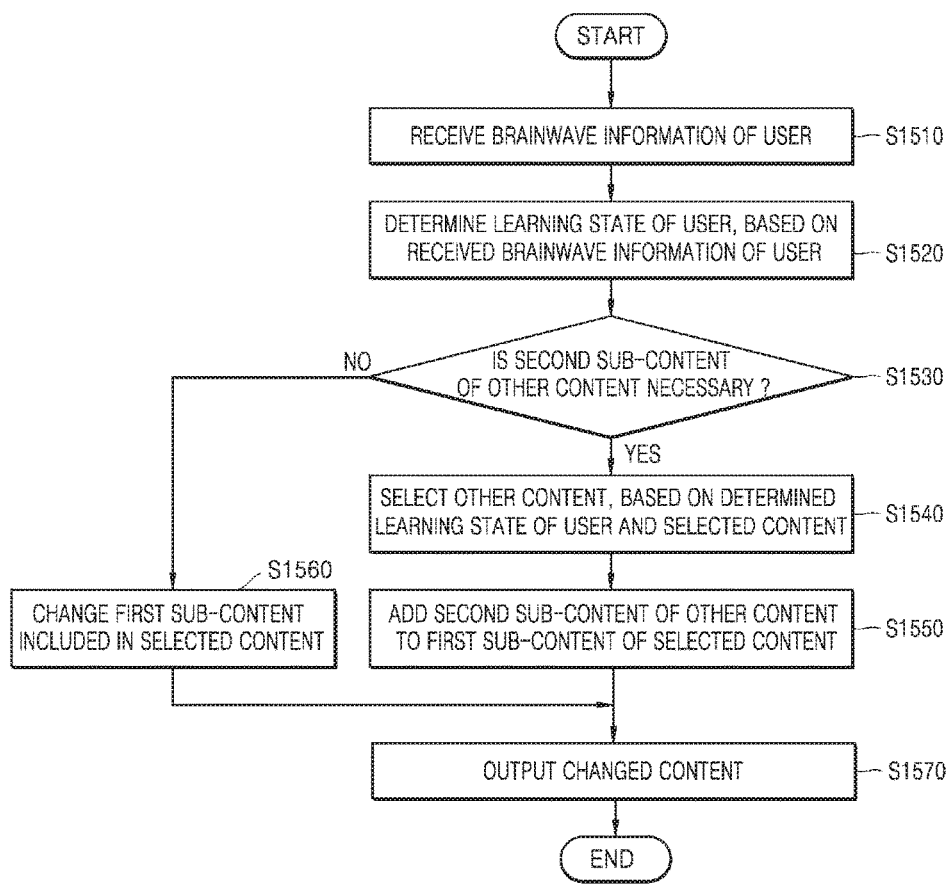
FIG. 15 is a flowchart of a method in which the device according to an embodiment of the present invention changes selected content by combining auxiliary sub-content of other content with main sub-content of the selected content according to received brainwave information of a user.

FIG. 15 is a flowchart of a method in which the device 100 according to an embodiment of the present invention changes selected content by adding second sub-content of other content to first sub-content of the selected content according to the received brainwave information of the user.

In operation S1510, the device 100 may receive the brainwave information of the user. When one of a plurality of pieces of content is selected, the device 100 according to an embodiment of the present invention may receive the brainwave information of the user from the sensing device 10. According to another embodiment, when one of a plurality of pieces of content is selected, the device 100 may receive brainwave information of the user detected while some pieces of sub-content included in the selected content are being output, from the sensing device 10.

In operation S1520, the device 100 may determine a learning state of the user, based on the received brainwave information of the user. The learning state of the user may be represented by using at least one of a concentration amount of the user, an understanding amount of the user, a stress amount of the user, and a memorization amount of the user.

In operation S1530, the device 100 may determine whether sub-content of the other content is necessary, based on the determined learning state of the user.

The device 100 according to an embodiment of the present invention may previously store, in the memory, information about a learning state when other content needs to be selected. The device 100 may determine whether to select other content, by comparing the determined learning state of the user with the information about the learning state previously stored in the memory. For example, in the case of a user having a concentration amount of 40 points or less and a stress amount of 60 points or greater, the device 100 may be set to select other content.

In operation S1540, the device 100 may select the other content, based on the determined learning state of the user and the selected content.

The device 100 according to an embodiment of the present invention may previously store information about other content selectable according to the learning state of the user and the selected content. For example, when the selected content is a digital mathematical textbook and a concentration amount of the user is 30 points and a stress amount of the user is 70 points, the device 100 may select a game application according to the pre-stored information. As another example, when a concentration amount of the user is 40 points and a stress amount of the user is 50 points, the device 100 may select a music playback application.

In operation S1550, the device 100 may change the selected content by adding sub-content of the other content to sub-content of the selected content.

The device 100 according to an embodiment of the present invention may change the selected content by adding at least one of a plurality of pieces of second sub-content included in the other content to at least one of a plurality of pieces of first sub-content included in the selected content. For example, the device 100 may select 10 pages from 30 pages included in the digital mathematical textbook. The device 100 may select a recently-frequently-output music file from a music application. The device 100 may change the content by adding the selected music file to the selected 10 pages.

The device 100 may change the selected content by adding changed at least one piece of second sub-content to changed at least one piece of first sub-content. The device 100 may change at least one of a frame, an image, and a text included in the selected at least one piece of first sub-content or the selected at least one piece of second sub-content. The device 100 may change the selected content by arranging changed sub-content.

In operation S1560, the device 100 may change the at least one of the plurality of pieces of first sub-content included in the selected content.

The device 100 according to an embodiment of the present invention may change at least one of a frame, an image, and a text included in the first sub-content. For example, the device 100 may change a location of a frame included in the lecture of the second unit included in the English video lecture. As another example, the device 100 may change at least one of a shape, a color, and a location of a text included in a page of a digital textbook. As another example, the device 100 may change an output location of audio data included in an English recording file.

In operation S1570, the device 100 may output changed content.

Operation S1570 may correspond to operation S250 described above with reference to FIG. 2.

Figure 16:
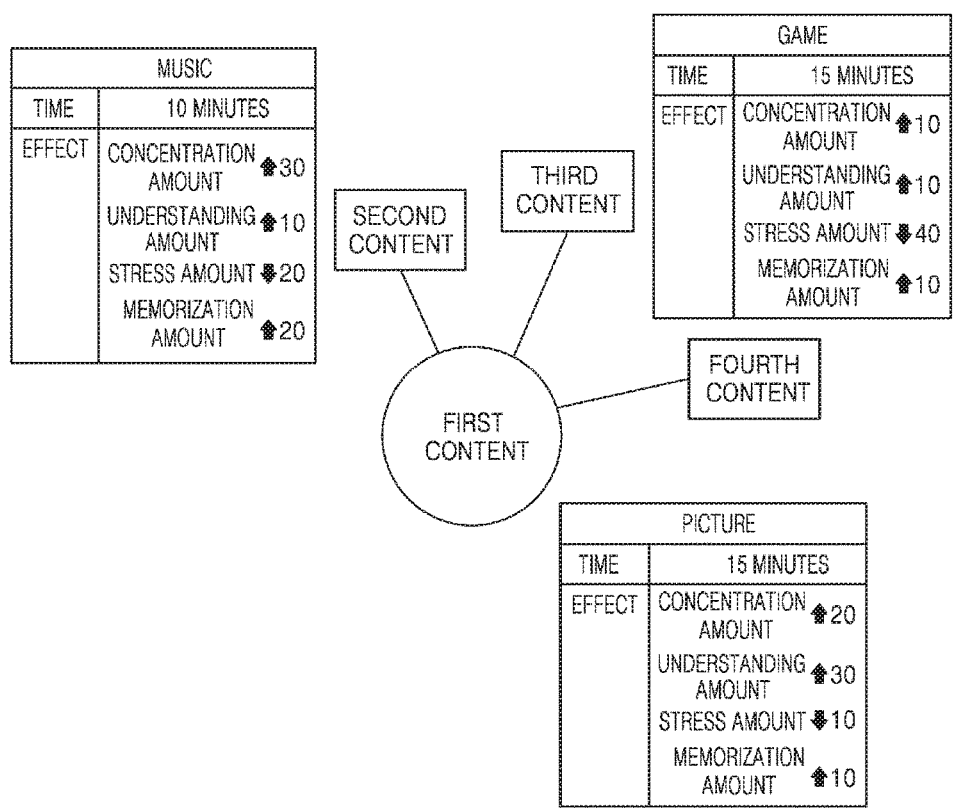
FIG. 16 is a schematic diagram for describing a method in which the device according to an embodiment of the present invention selects other content related to selected content by using received brainwave information of a user.

FIG. 16 is a schematic diagram for describing a method in which the device 100 according to an embodiment of the present invention selects other content related to selected content by using received brainwave information of a user.

The device 100 may select the other content, based on the selected content and a determined learning state of the user. The device 100 may previously store information about a relationship between the selected content and other content related to the selected content.

Referring to FIG. 16, the device 100 may previously store information about second content, third content, and fourth content related to selected first content. For example, when the device 100 combines the selected first content with music content, which is the second content, the device 100 may obtain, from the pre-stored information, information indicating that a concentration amount and an understanding amount respectively increase by 30 points and 10 points, a stress amount decreases by 20 points, and a memorization amount increases by 20 points. The device 100 may also previously store information about a time period of the second content that is added to the first content.

As another example, when the device 100 adds a game application, which is the third content, to the selected first content, the device 100 may obtain, from the pre-stored information, information indicating that each of a concentration amount and an understanding amount increases by 10 points, a stress amount decreases by 40 points, and a memorization amount increases by 20 points. The device 100 may also previously store information about a time period of the third content that is added to the first content.

As another example, when the device 100 adds a picture, which is the fourth content, to the selected first content, the device 100 may obtain, from the pre-stored information, information indicating that a concentration amount and an understanding amount respectively increase by 20 points and 30 points, a stress amount decreases by 10 points, and a memorization amount increases by 10 points. The device 100 may also previously store information about a time period of the fourth content that is added to the first content.

The device 100 may select other content suitable for using the selected content, based on the determined learning state of the user. For example, when the stress amount of the user is higher than the stress amount threshold by a certain level or greater, the device 100 may select a game that is effective to decrease the stress amount. When the concentration amount of the user is lower than the concentration amount threshold by a certain range or greater, the device 100 may select music that is effective to increase the concentration amount.

Figure 17:
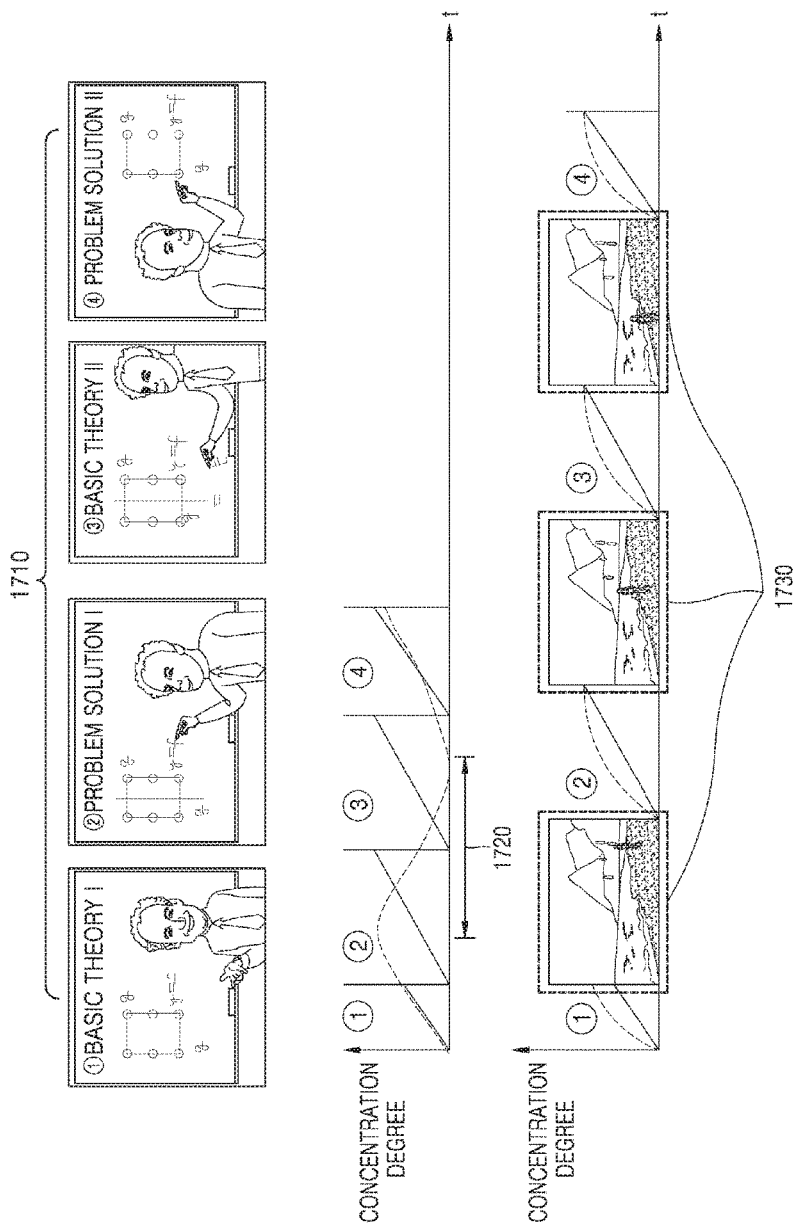
FIG. 17 is a schematic diagram for describing a method in which the device according to an embodiment of the present invention changes selected video content by combining a picture, which is other content, with the selected video content according to received brainwave information of a user.

FIG. 17 is a schematic diagram for describing a method in which the device 100 according to an embodiment of the present invention changes selected video content by adding other video content to the selected video content according to received brainwave information of a user.

Referring to FIG. 17, the device 100 may receive the brainwave information of the user from the sensing device 10. The device 100 may determine a concentration degree of the user, based on the received brainwave information of the user.

The content selected by the device 100 may include four pieces of video sub-content 1710 which are mathematical lecture videos. The device 100 may determine a concentration amount of the user with respect to the four pieces of video sub-content 1710, based on the determined concentration degree of the user. The device 100 may compare the determined concentration amount of the user with a concentration amount threshold for the four pieces of video sub-content 1710.

The device 100 may determine a section 1720 where the determined concentration amount of the user does not correspond to the concentration amount threshold. The device 100 may change the selected content by inserting other content 1730 into the section 1720, where the concentration amount of the user does not correspond to the concentration amount threshold, or before and after the section 1720. Referring to FIG. 13, the device 100 may change the selected content by inserting meditation videos 1730 between pieces of sub-content of the mathematical lecture video.

Figure 18:
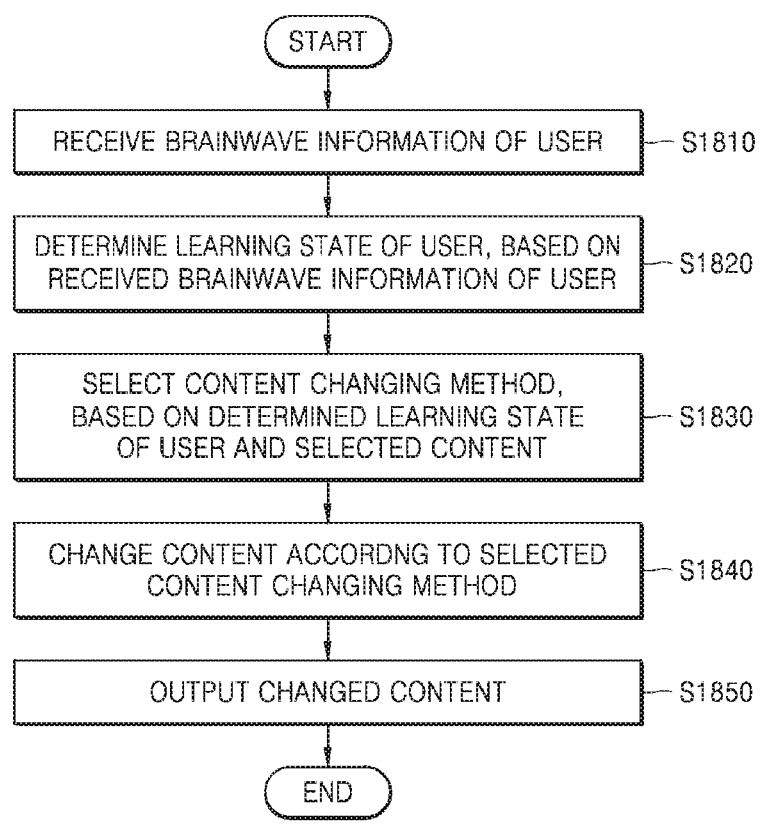
FIG. 18 is a flowchart of a method in which the device according to an embodiment of the present invention selects a method of changing sub-content included in selected content according to received brainwave information of a user.

FIG. 18 is a flowchart of a method in which the device 100 according to an embodiment of the present invention selects a method of changing sub-content included in selected content according to received brainwave information of a user.

In operation S1810, the device 100 may receive the brainwave information of the user. When one of a plurality of pieces of content is selected, the device 100 according to an embodiment of the present invention may receive brainwave information of the user from the sensing device 10. According to another embodiment, when one of a plurality of pieces of content is selected, the device 100 may receive brainwave information of the user detected while some pieces of sub-content included in the selected content are being output, from the sensing device 10.

In operation S1820, the device 100 may determine a learning state of the user, based on the received brainwave information of the user. The learning state of the user may be represented by using at least one of a concentration amount of the user, an understanding amount of the user, a stress amount of the user, and a memorization amount of the user.

In operation S1830, the device 100 may select a content changing method, based on the determined learning state of the user and the selected content.

The device 100 according to an embodiment of the present invention may previously store, in the memory, information about content changing methods according to learning states of the user for each type of content. For example, the device 100 may classify content changing methods for video content according to values of a concentration amount, an understanding amount, a stress amount, and a memorization amount of the user and may store the classified content changing methods in advance.

The device 100 may select a method of changing selected content, by comparing the determined learning state of the user with a pre-stored learning state. For example, when the concentration amount of the user is 30 points, the device 100 may select a method of selecting some of a plurality of pieces of video sub-content included in a selected English video lecture. The device 100 may preferentially select video sub-content having higher ranking as opposed to video sub-content having lower ranking, based on information about the ranking of importance or difficulty of the plurality of pieces of video sub-content included in the metadata of the selected English video lecture. However, this is merely an embodiment, and the device 100 may output identification (ID) values of the plurality of pieces of video sub-content, such as titles thereof, to the screen of the device 100 such that the user may select desired video sub-content.

As another example, when the concentration amount of the user is 50 points and the understanding amount of the user is 40 points, the device 100 may select a method of emphasizing some of a plurality of mathematical problems included in a selected digital mathematical textbook. Herein, the device 100 may preferentially select a problem of higher importance as opposed to a problem of lower importance, based on importance information of a plurality of mathematical problems included in the metadata of the selected digital mathematical textbook. However, this is merely an embodiment, and the device 100 may output ID values of the mathematical problems, such as units corresponding to the mathematical problems, to the screen of the device 100 such that the user may select a desired mathematical problem.

In operation S1840, the device 100 may change the selected content according to the content changing method selected in operation S1830. According to an embodiment of the present invention, the selected content may be one of a plurality of pieces of content stored in the device 100. The device 100 may change stored content according to the content changing method selected in operation S1830.

According to another embodiment, the device 100 may receive the selected content from an external device and stream the selected content. When the device 100 streams the selected content, the device 100 may transmit information about the determined content changing method to the external device. The external device may change the selected content according to the content changing method received from the device 100 and transmit changed content to the device 100. However, this is merely an embodiment, and, when the device 100 streams the selected content, the device 100 may change the content received from the external device according to the selected content changing method.

In operation S1850, the device 100 may output changed content.

Operation S1850 may correspond to operation S250 described above with reference to FIG. 2.

FIG. 19 illustrates tables for explaining information about content changing methods previously stored in the device 100, according to an embodiment of the present invention.

Referring to FIG. 19, the device 100 may classify content changing methods corresponding to learning states of the user according to the types of content and previously store the classified content changing methods.

According to an embodiment of the present invention, the device 100 may change selected content by selecting some of a plurality of pieces of sub-content included in the selected content. As another example, the device 100 may emphasize, replace, or publicize some of the objects that constitute each of the plurality of pieces of sub-content included in the selected content, or change locations of the some objects. However, this is only an embodiment, and the content changing methods of the device 100 are not limited thereto.

(a) of FIG. 19 shows a table in which content changing methods for text content are classified according to learning states of the user. Referring to the table shown in (a) of FIG. 19, the device 100 may select some of a plurality of pieces of text sub-content included in the text content. The device 100 may emphasize, replace, or publicize some of the texts that constitute each of the plurality of pieces of sub-content included in the text content, or change locations of the some texts.

The device 100 may classify a plurality of text content changing methods according to learning states of the user and may store the classified text content changing methods. For example, when the determined learning state of the user corresponds to a concentration amount of 30 points, an understanding amount of 50 points, a stress amount of 20 points, and a memorization amount of 10 points, the device 100 may select a method of splitting the plurality of pieces of sub-content included in the text content.

The device 100 according to an embodiment of the present invention may select a content changing method by prioritizing one of the concentration amount, the understanding amount, the stress amount, and the memorization amount. For example, when the concentration amount is given priority, the determined learning state of the user corresponds to a concentration amount of 26 points, an understanding amount of 47 points, a stress amount of 20 points, a memorization amount of 10 points, and a threshold range is 4, the device 100 may select the method of splitting the plurality of pieces of sub-content included in the text content.

(b) of FIG. 19 shows a table in which content changing methods for video content are classified according to learning states of the user. Referring to the table shown in (b) of FIG. 19, the device 100 may select some of a plurality of pieces of video sub-content included in the video content. The device 100 may insert an object into the plurality of pieces of video sub-content included in the video content. For example, the device 100 may insert subtitles into each of the plurality of pieces of video sub-content included in the video content. The device 100 may change an output speed or an output frequency of the video content.

The device 100 according to an embodiment of the present invention may classify a plurality of video content changing methods according to learning states of the user and may store the classified video content changing methods. The device 100 according to an embodiment of the present invention may select a content changing method by prioritizing one of the concentration amount, the understanding amount, the stress amount, and the memorization amount. For example, when the understanding amount is given priority and the determined learning state of the user corresponds to a concentration amount of 45 points, an understanding amount of 10 points, a stress amount of 20 points, and a memorization amount of 30 points, the device 100 may select a method of changing the output speed of the video content.

Figure 20:
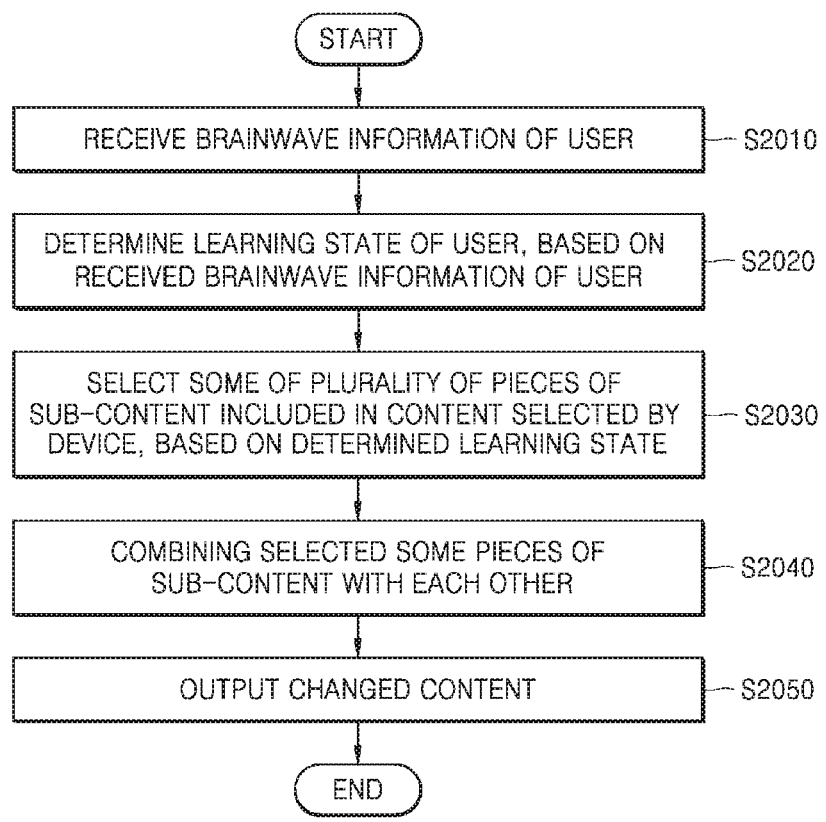
FIG. 20 is a flowchart of a method in which the device according to an embodiment of the present invention changes selected content by selecting some of a plurality of pieces of sub-content included in the selected content according to a determined learning state of the user.

FIG. 20 is a flowchart of a method in which the device 100 according to an embodiment of the present invention changes selected content by selecting some of a plurality of pieces of sub-content included in the selected content according to a determined learning state of a user.

In operation S2010, the device 100 may receive brainwave information of the user. When one of a plurality of pieces of content is selected, the device 100 according to an embodiment of the present invention may receive the brainwave information of the user from the sensing device 10. According to another embodiment, when one of a plurality of pieces of content is selected, the device 100 may receive brainwave information of the user detected while some pieces of sub-content included in the selected content are being output, from the sensing device 10.

In operation S2020, the device 100 may determine the learning state of the user, based on the received brainwave information of the user. The learning state of the user may be represented by using at least one of a concentration amount of the user, an understanding amount of the user, a stress amount of the user, and a memorization amount of the user.

The device 100 according to an embodiment of the present invention may determine a concentration amount representing the range of content on which the user may concentrate in the future, based on the received brainwave information of the user. The device 100 may also determine a concentration amount representing the range of content which the user may understand in the future, based on the received brainwave information of the user. The device 100 may also determine a stress amount which the user may receive in the future, based on the received brainwave information of the user. The device 100 may also determine a memorization amount representing the range of content which the user may memorize in the future, based on the received brainwave information of the user.

In operation S2030, the device 100 may select some of the plurality of pieces of sub-content included in the content selected by the device 100, based on the determined learning state and the selected content.

The device 100 according to an embodiment of the present invention may compare the determined learning state of the user with a threshold for the selected content. When the determined learning state of the user does not correspond to the threshold for the selected content, the device 100 may select some of the plurality of pieces of sub-content included in the selected content.

For example, a concentration amount threshold for 10 pieces of sub-content included in selected video content may be 100 points. The concentration amount of the user determined based on the brainwave information received from the device 100 may be 40 points. The device 100 may select some pieces of sub-content corresponding to the determined concentration amount of 40 points from among the 10 pieces of video sub-content included in the selected video content.

Herein, the device 100 may select some pieces of sub-content, based on importance information included in the metadata of the selected video content. For example, the device 100 may select pieces of sub-content with rankings 1 through 4 ranked in terms of importance from among the 10 pieces of video sub-content, based on the determined concentration amount of the user.

In operation S2040, the device 100 may change the selected content by combining the selected some pieces of sub-content with each other.

The device 100 according to an embodiment of the present invention may arrange the selected some pieces of sub-content according to a predetermined order to combine them. For example, the device 100 may arrange four pieces of sub-content selected from the video content according to a predetermined order and combine them.

As another example, the device 100 may arrange the selected some pieces of sub-content, based on the determined learning state of the user. For example, when the determined understanding amount of the user is lower than the understanding amount threshold, the device 100 may preferentially arrange sub-content of low difficulty as opposed to the other sub-content.

As another example, the device 100 may arrange the selected some pieces of sub-content, according to an input of the user. For example, the device 100 may output ID information of the selected some pieces of sub-content. The user may input arrangement information to the device 100 such that, based on the ID information of the output pieces of sub-content, some pieces of sub-content are arranged in an order desired by the user. The device 100 may arrange the selected some pieces of sub-content, according to the input arrangement information.

In operation S2050, the device 100 may output changed content.

Operation S2050 may correspond to operation S250 described above with reference to FIG. 2.

Figure 21:
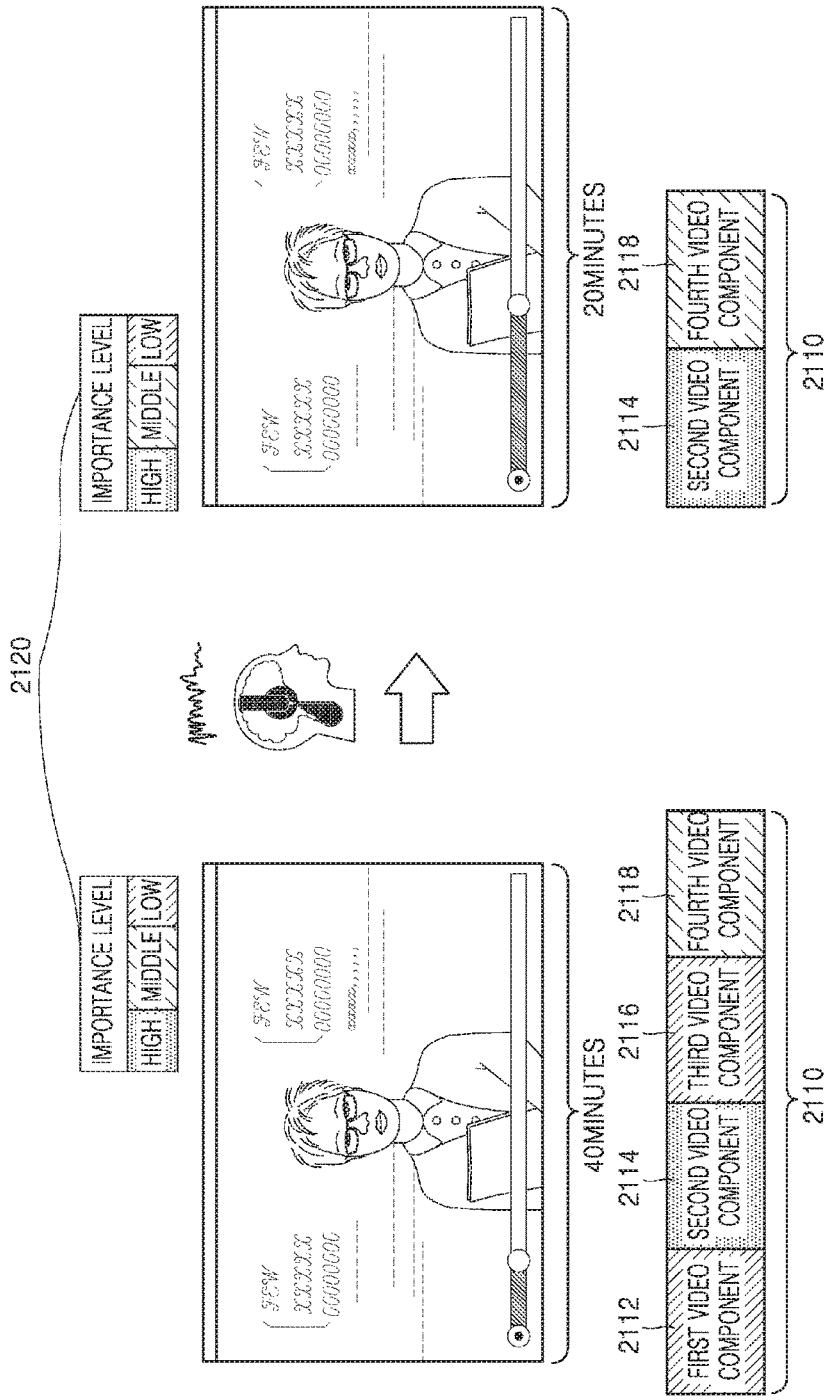
FIG. 21 is a schematic diagram for explaining a method in which the device according to an embodiment of the present invention changes selected video content by selecting some of a plurality of pieces of video sub-content included in the selected video content according to a determined learning state of a user.

FIG. 21 is a schematic diagram for explaining a method in which the device 100 according to an embodiment of the present invention changes selected video content by selecting some of a plurality of pieces of sub-content included in the selected video content according to a determined learning state of a user.

Referring to FIG. 21, the device 100 may output a selected English lecture video 2110. The English lecture video 2110 may include sub-content a 2112, sub-content b 2114, sub-content c 2116, and sub-content d 2118. The pieces of sub-content 2112, 2114, 2116, and 2118 included in the English lecture video 2110 may be obtained by splitting the English lecture video 2110 according to, for example, lecture themes, lecture time, and the capacity of video data. Each of the pieces of sub-content 2112, 2114, 2116, and 2118 may be identified according to an ID value of sub-content included in metadata of the English lecture video 2110.

The device 100 may receive brainwave information of the user detected while the sub-content a 2112 is being output, from the sensing device 10. The device 100 may determine at least one of a concentration amount, an understanding amount, a stress amount, and a memorization amount of the user by using the received brainwave information of the user. Herein, the determined at least one of the concentration amount, the understanding amount, the stress amount, and the memorization amount of the user may be at least one of a concentration amount, an understanding amount, a stress amount, and a memorization amount of the user with respect to the sub-content b 2114, the sub-content c 2116, and the sub-content d 2118 which are to be output in the future.

As another example, the at least one of the concentration amount, the understanding amount, the stress amount and the memorization amount of the user determined by the device 100 may be at least one of the concentration amount, the understanding amount, the stress amount and the memorization amount of the user with respect to the sub-content a 2112. However, it is described in FIG. 21 that the device 100 determines at least one of the concentration amount, the understanding amount, the stress amount, and the memorization amount of the user with respect to the sub-content b 2114, the sub-content c 2116, and the sub-content d 2118 which are to be output in the future.

The device 100 according to an embodiment of the present invention may determine the concentration amount of the user to be 20 points, based on the received brainwave information of the user. The device 100 may also determine the understanding amount of the user to be 70 points, based on the received brainwave information of the user. The device 100 may compare the determined concentration amount and the determined understanding amount of the user with a concentration amount threshold and an understanding amount threshold for the plurality of pieces of sub-content 2114, 2116, and 2118. Herein, it is assumed that the concentration amount threshold is 30 points and the understanding amount threshold is 50 points.

Because the determined concentration amount of the user does not correspond to the concentration amount threshold, the device 100 may change the English lecture video 2110. The device 100 may search for content changing methods classified for the English lecture video 2110, from information about pre-stored content changing methods. The device 100 may determine a method of selecting some pieces of sub-content, which is a content changing method corresponding to the determined concentration amount and the determined understanding amount of the user, from among the searched content changing methods.

The device 100 may select the sub-content b 2114 and the sub-content d 2118 from among the plurality of pieces of sub-content 2114, 2116, and 2118 included in the English lecture video 2110 and not yet output. Herein, the device 100 may select the sub-content b 2114 and the sub-content d 2118 having high importance, by referring to importance information about the plurality of pieces of sub-content 2112, 2114, 2116, and 2118 from metadata 2120 with respect to the English lecture video 2110.

The device 100 may change the content 2110 by combining the selected sub-content b 2114 with the selected sub-content d 2118. The device 100 may combine the selected sub-content b 2114 with the selected sub-content d 2118 by sequentially arranging the sub-content b 2114 and the sub-content d 2118 according to order information previously determined for the plurality of pieces of sub-content 2112, 2114, 2116, and 2118. However, this is merely an embodiment, and the device 100 may arrange the sub-content b 2114 and the sub-content d 2118 according to difficulty, by taking into account difficulty information set in metadata of the sub-content b 2114 and the sub-content d 2118.

The device 100 according to an embodiment of the present invention may select the some pieces of sub-content 2114 and 2118 from the English lecture video 2110 requiring 40 minutes to be output, and thus change the content 2110 such that it takes 20 minutes to output the content 2110.

The device 100 may output changed content 2130. The device 100 according to an embodiment of the present invention may continuously receive the brainwave information of the user while the changed content 2130 is being output. The device 100 may re-change the changed content 2130, based on brainwave information of the user detected while some pieces of sub-content included in the changed content 2130 are being output.

Figure 22:
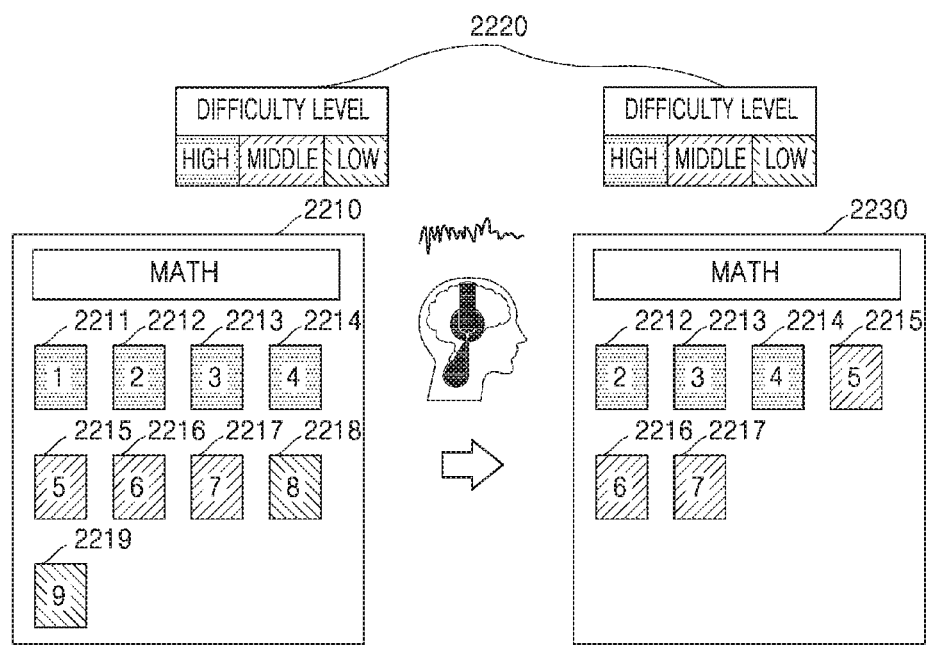
FIG. 22 is a schematic diagram for explaining a method in which the device according to an embodiment of the present invention changes selected image content by selecting some of a plurality of pieces of image sub-content included in the selected image content according to a determined learning state of a user.

FIG. 22 is a schematic diagram for explaining a method in which the device 100 according to an embodiment of the present invention changes selected text content 2210 by selecting some of a plurality of pieces of sub-content 2211 through 2219 included in the selected video content 2210 according to a determined learning state of a user.

Referring to FIG. 22, the device 100 may output a selected digital mathematical problem collection 2210. The digital mathematical problem collection 2210 may include a plurality of pieces of sub-content 2211 through 2219 for mathematical problems. Each of the plurality of pieces of sub-content 2211 through 2219 may be identified according to an ID value of sub-content included in metadata of the digital mathematical problem collection 2210.

While math question number 1 of the sub-content a 2211 is being output, the device 100 may receive the brainwave information of the user from the sensing device 10. The device 100 may determine at least one of a concentration amount, an understanding amount, a stress amount, and a memorization amount of the user by using the received brainwave information of the user.

The device 100 according to an embodiment of the present invention may determine the understanding amount of the user to be 30 points, based on the received brainwave information of the user. The device 100 may compare the determined understanding amount of the user with an understanding amount threshold for the plurality of pieces of sub-content 2211 through 2219. Herein, it is assumed that the understanding amount threshold is 50 points.

Because the determined understanding amount of the user does not correspond to the understanding amount threshold, the device 100 may change the digital mathematical problem collection 2210. The device 100 may search for content changing methods classified for the digital mathematical problem collection 2210, from information about pre-stored content changing methods. The device 100 may determine a method of selecting some pieces of sub-content, which is a content changing method corresponding to the determined understanding amount of the user, from among the searched content changing methods.

The device 100 may select the sub-content b 2212 through d 2217 from among the plurality of pieces of sub-content 2212 through 2219 included in the digital mathematical problem collection 2210 and not yet output. Herein, the device 100 may select the sub-content b 2212 through g 2217 corresponding to middle difficulty and low difficulty by referring to difficulty information about the plurality of pieces of sub-content 2211 through 2219 from metadata 2220 with respect to the digital mathematical problem collection 2210.

The device 100 may change the content 2210 by combining the selected sub-content b 2212 through g 2217 with each other. The device 100 may combine the selected sub-content b 2211 through g 2217 by sequentially arranging the selected sub-content b 2211 through g 2217 according to order information previously determined for the plurality of pieces of sub-content 2211 through 2219. However, this is merely an embodiment, and the device 100 may preferentially arrange the pieces of sub-content e 2215 through g 2217 having middle difficulty as opposed to the pieces of sub-content a 2211 through d 2214 having low difficulty, by taking into account difficulty information set in metadata of the pieces of sub-content b 2212 through g 2217.

The device 100 may output changed content 2230. The device 100 according to an embodiment of the present invention may continuously receive the brainwave information of the user while the changed content 2230 is being output. The device 100 may re-change the changed content 2230, based on brainwave information of the user detected while some pieces of sub-content included in the changed content 2230 are being output.

Figure 23:
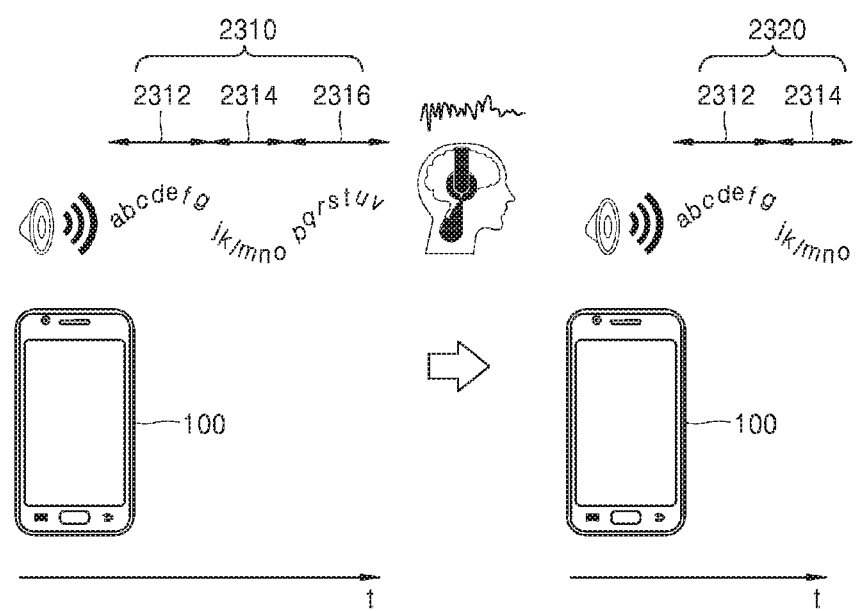
FIG. 23 is a schematic diagram for explaining a method in which the device according to an embodiment of the present invention changes selected audio content by selecting some of a plurality of pieces of audio sub-content included in the selected audio content according to a determined learning state of a user.

FIG. 23 is a schematic diagram for explaining a method in which the device 100 according to an embodiment of the present invention changes audio content 2310 by selecting some of a plurality of pieces of sub-content 2312, 2314, and 2316 included in the audio content 2310 according to a learning state of a user.

Referring to FIG. 23, the device 100 may output audio broadcasting 2310. The audio broadcasting 2310 may include the plurality of pieces of sub-content 2312, 2314, and 2316. The plurality of pieces of sub-content 2312, 2314, and 2316 included in the audio broadcasting 2310 may be obtained by splitting the audio broadcasting 2310 according to, for example, lecture themes, lecture time, and the capacity of audio data. Each of the plurality of pieces of sub-content 2312, 2314, and 2316 may be identified according to an ID value of sub-content included in metadata of the audio broadcasting 2310. The ID value may be, for example, a time stamp of the sub-content. However, this is merely an embodiment of the present invention, and the present invention is not limited thereto.

When the audio broadcasting 2310 is selected, the device 100 may receive the brainwave information of the user from the sensing device 10. The device 100 may determine at least one of a concentration amount, an understanding amount, a stress amount, and a memorization amount of the user, by using the received brainwave information of the user.

The device 100 according to an embodiment of the present invention may determine the understanding amount of the user to be 20 points, based on the received brainwave information of the user. The device 100 may compare the determined understanding amount of the user with an understanding amount threshold for the plurality of pieces of sub-content 2312, 2314, and 2316. Herein, it is assumed that the understanding amount threshold is 30 points.

Because the determined understanding amount of the user does not correspond to the understanding amount threshold, the device 100 may change the audio broadcasting 2310. The device 100 may search for content changing methods classified for the audio broadcasting 2310, from information about pre-stored content changing methods. The device 100 may determine a method of selecting some pieces of sub-content, which is a content changing method corresponding to the concentration amount of the user, from among the searched content changing methods.

The device 100 may select the sub-content a 2312 and the sub-content b 2314 from among the plurality of pieces of sub-content 2312, 2314, and 2316 included in the audio broadcasting 2310, according to the determined method. Herein, the device 100 may select the pieces of sub-content 2312 and 2314 having higher importance than the other sub-content 2136 by referring to importance information of the plurality of pieces of sub-content 2312, 2314, and 2316 from the metadata of the audio broadcasting 2310.

The device 100 may change the content 2310 by combining the selected sub-content a 2312 with the selected sub-content b 2314. The device 100 may combine the selected sub-content a 2312 with the selected sub-content b 2314 by sequentially arranging them according to predetermined order information. However, this is merely an embodiment, and the device 100 may combine the sub-content a 2312 and the sub-content b 2314 by preferentially arranging the sub-content b 2314 as opposed to the sub-content a 2312 according to a selection by the user.

The device 100 may output changed content 2320. The device 100 according to an embodiment of the present invention may continuously receive the brainwave information of the user while the changed content 2320 is being output. The device 100 may re-change the changed content 2320, based on brainwave information of the user detected while some pieces of sub-content included in the changed content 2320 are being output.

Figure 24:
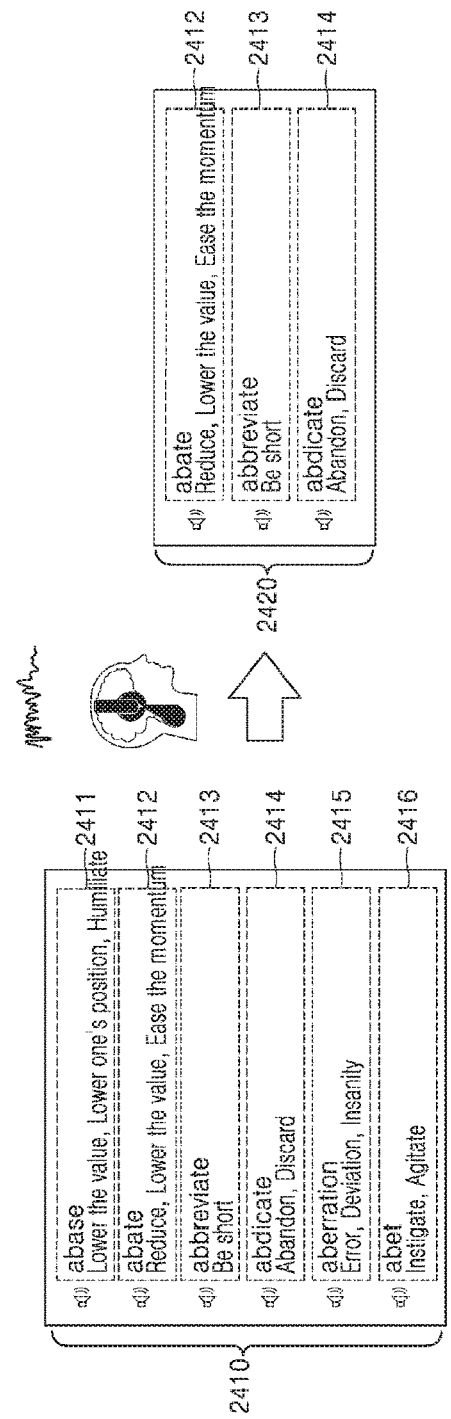
FIG. 24 is a schematic diagram for explaining a method in which the device according to an embodiment of the present invention changes selected text content by selecting some of a plurality of pieces of text sub-content included in the selected text content according to a determined learning state of a user.

FIG. 24 is a schematic diagram for explaining a method in which the device 100 according to an embodiment of the present invention changes text content 2410 by selecting some of a plurality of pieces of sub-content 2412, 2414, and 2416 included in the text content 2410 according to a learning state of a user.

Referring to FIG. 24, the device 100 may output a digital English vocabulary list 2410. The digital English vocabulary list 2410 may include a plurality of pieces of sub-content 2411 through 2416. Each of the plurality of pieces of sub-content 2411 through 2416 included in the digital English vocabulary list 2410 may be identified according to an ID value of sub-content included in metadata of the digital English vocabulary list 2410.

The device 100 may receive, from the sensing device 10, brainwave information of the user detected while the sub-content a 2411 included in the digital English vocabulary list 2410 is being output. The device 100 may determine at least one of a concentration amount, an understanding amount, a stress amount, and a memorization amount of the user, by using the received brainwave information of the user.

The device 100 according to an embodiment of the present invention may determine the memorization amount of the user to be 30 points, based on the received brainwave information of the user. The device 100 may compare the determined memorization amount of the user with a memorization amount threshold for the plurality of pieces of sub-content 2412 through 2416 that are not yet output. Herein, it is assumed that the memorization amount threshold is 50 points.

Because the determined memorization amount of the user does not correspond to the memorization amount threshold, the device 100 may change the digital English vocabulary list 2410. The device 100 may search for content changing methods classified for the digital English vocabulary list 2410, from information about pre-stored content changing methods. The device 100 may determine a method of selecting some pieces of sub-content, which is a content changing method corresponding to the memorization amount of the user, from among the searched content changing methods.

The device 100 may select the sub-content b 2412, the sub-content c 2413, and the sub-content d 2414 from among the plurality of pieces of sub-content 2411 through 2416 included in the digital English vocabulary list 2410, according to the determined method. Herein, the device 100 may select the pieces of sub-content 2412, 2413, and 2414 having higher importance than the other pieces of sub-content 2415 and 2416 by referring to importance information of the plurality of pieces of sub-content 2411 through 2416 from metadata with respect to the digital English vocabulary list 2410.

The device 100 may change the content 2410 by combining the selected plurality of pieces of sub-content 2412, 2413, and 2414 with each other. The device 100 may combine the selected sub-content b 2412, the selected sub-content c 2413, and the selected sub-content d 2414 by sequentially arranging them according to order information previously determined for the plurality of pieces of sub-content 2412, 2413, and 2414. However, this is merely an embodiment, and the device 100 may combine the plurality of pieces of sub-content 2412, 2413, and 2414 with each other by first arranging sub-content having high importance.

The device 100 may output changed content 2420. The device 100 according to an embodiment of the present invention may continuously receive the brainwave information of the user while the changed content 2420 is being output. The device 100 may re-change the changed content 2420, based on brainwave information of the user detected while some pieces of sub-content included in the changed content 2420 are being output.

Figure 25:
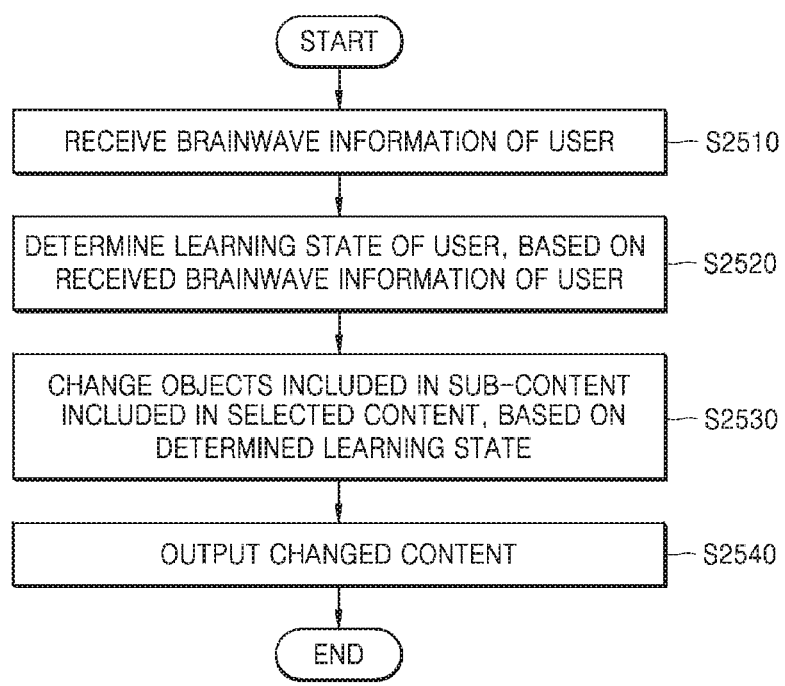
FIG. 25 is a flowchart of a method in which the device according to an embodiment of the present invention changes an object included in sub-content of selected content, based on received brainwave information of a user.

FIG. 25 is a flowchart of a method in which the device 100 according to an embodiment of the present invention changes selected content by changing an object included in sub-content of the selected content, according to received brainwave information of a user.

In operation S2510, the device 100 may receive the brainwave information of the user. When one of a plurality of pieces of content is selected, the device 100 according to an embodiment of the present invention may receive brainwave information of the user from the sensing device 10. According to another embodiment, when one of a plurality of pieces of content is selected, the device 100 may receive brainwave information of the user detected while some pieces of sub-content included in the selected content are being output, from the sensing device 10.

In operation S2520, the device 100 may determine a learning state of the user, based on the received brainwave information of the user. The learning state of the user may be represented by using at least one of a concentration amount of the user, an understanding amount of the user, a stress amount of the user, and a memorization amount of the user.

Operation S2520 may correspond to operation S2020 described above with reference to FIG. 20.

In operation S2530, the device 100 may change objects included in sub-content included in the content selected by the device 100, based on the determined learning state and the selected content.

The device 100 according to an embodiment of the present invention may compare the determined learning state of the user with a threshold necessary for learning the selected content. When the determined learning state of the user does not correspond to the threshold for the selected content, the device 100 may change the objects of the sub-content included in the selected content. For example, the device 100 may change the shapes, colors, sizes, and locations of at least some of the objects included in the sub-content of the selected content. The device 100 may add objects included in other sub-content to the sub-content of the selected content. The device 100 may delete an object included in the sub-content of the selected content or replace the object with an object included in the other sub-content. The method in which the device 100 changes the objects of the sub-content included in the selected content will be described in more detail with reference to FIGS. 26-29.

In operation S2540, the device 100 may output changed content.

Operation S2540 may correspond to operation S250 described above with reference to FIG. 2.

Figure 26:
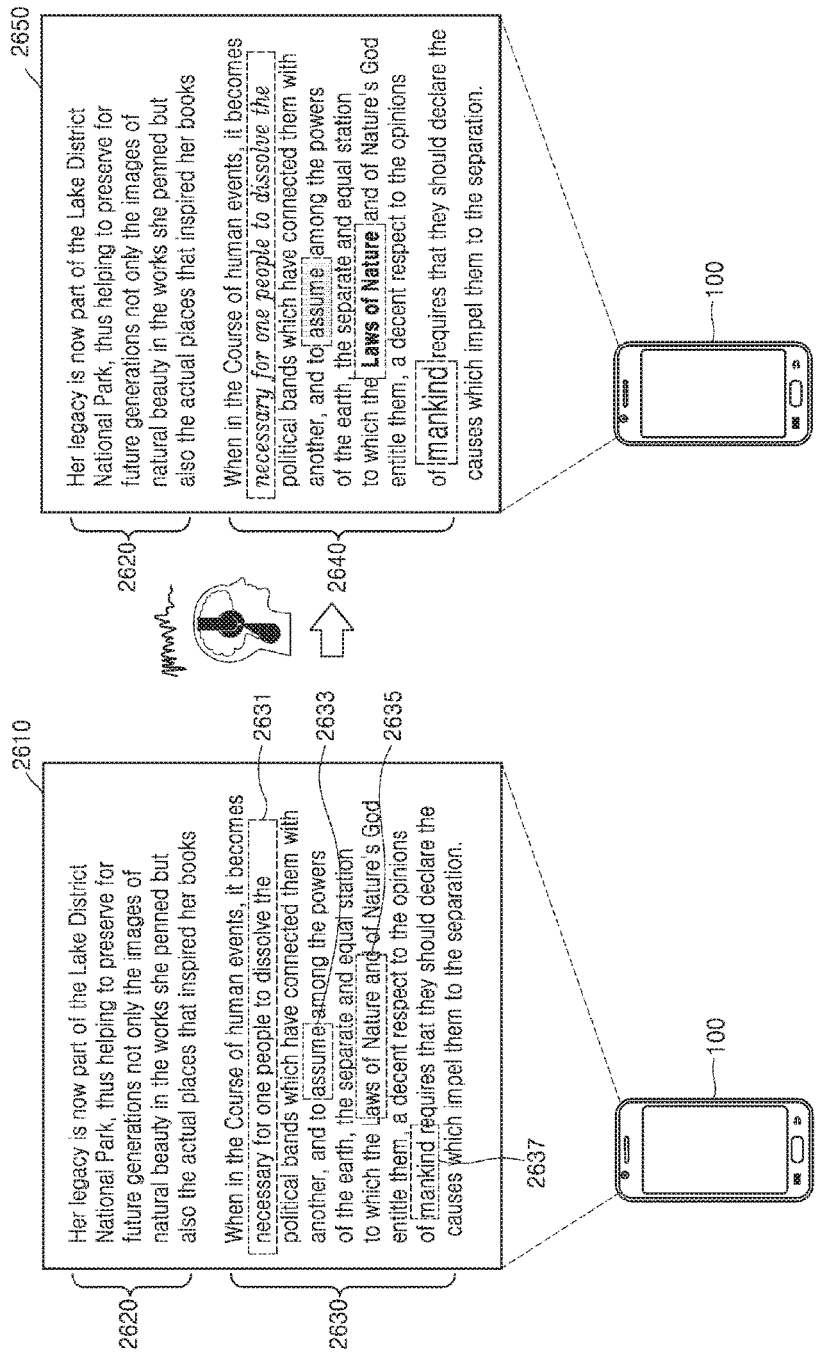
FIG. 26 is a schematic diagram for explaining a method in which the device according to an embodiment of the present invention changes some pieces of objects included in sub-content of selected text content, based on received brainwave information of a user.

FIG. 26 is a schematic diagram for explaining a method in which the device 100 according to an embodiment of the present invention changes some objects 2631, 2633, 2635, and 2637 included in sub-content 2630 of selected text content 2610, based on received brainwave information of a user.

Referring to FIG. 26, the device 100 may output the text content 2610. The text content 2610 may include a plurality of pieces of sub-content 2620 and 2630. Each of the plurality of pieces of sub-content 2620 and 2630 included in the text content 2610 may be identified according to an ID value of sub-content included in metadata of the text content 2610. For example, when the pieces of sub-content 2620 and 2630 of the text content 2610 are identified according to paragraphs, the metadata of the text content 2610 may include an ID value of each of the paragraphs.

The device 100 may receive, from the sensing device 10, brainwave information of the user detected while the sub-content a 2620 of the selected text content 2610 is being output. The device 100 may determine a concentration amount of the user, based on the received brainwave information of the user. For example, the device 100 may determine the concentration amount of the user to be 30 points.

The device 100 may compare the concentration amount of the user with a concentration amount threshold for the sub-content b 2630 that is not yet output. Herein, it is assumed that the concentration amount threshold is 40 points.

Because the concentration amount of the user does not correspond to the concentration amount threshold, the device 100 may change the some objects 2631, 2633, 2635, and 2637 included in the sub-content b 2620 of the text content 2610. The device 100 may change the selected text content 2610 to correspond to the concentration amount of the user.

The device 100 may search for content changing methods classified for the text content 2610, from information about pre-stored content changing methods. The device 100 may determine a method of selecting the objects included in sub-content, which is a content changing method corresponding to the concentration amount of the user, from among the searched content changing methods.

The device 100 may change the sub-content b 2630 by changing the some objects 2631, 2633, 2635, and 2637 included in the text content 2610 according to the determined method. Herein, the device 100 may select the some objects 2631, 2633, 2635, and 2637 having higher importance than the other objects, by referring to importance information of the sub-content b 2630 from the metadata of the text content 2610. The method in which the device 100 changes the selected some objects 2631, 2633, 2635, and 2637 will now be described in detail.

Referring to FIG. 26, the device 100 may change the thickness of the selected second object 2633. For example, the device 100 may change the thickness of the second object 2633 to be greater than thicknesses of the other objects included in the second sub-content 2630. The device 100 may also change the color of the selected first object 2631. For example, the device 100 may change the color of the first object 2631 from black to blue.

The device 100 may change the shape of the third object 2635. For example, the device 100 may change the shape of the third object 2635 such that the third object 2635 is inclined. The device 100 may change the size of the selected fourth object 2637. For example, the device 100 may increase the size of the fourth object 2637.

The device 100 may change the selected objects 2631, 2635, 2637, and 2639. However, this is only an embodiment, and the method in which the device 100 changes objects included in the selected content 2610 is not limited thereto.

The device 100 may output changed content 2650.

Figure 27:
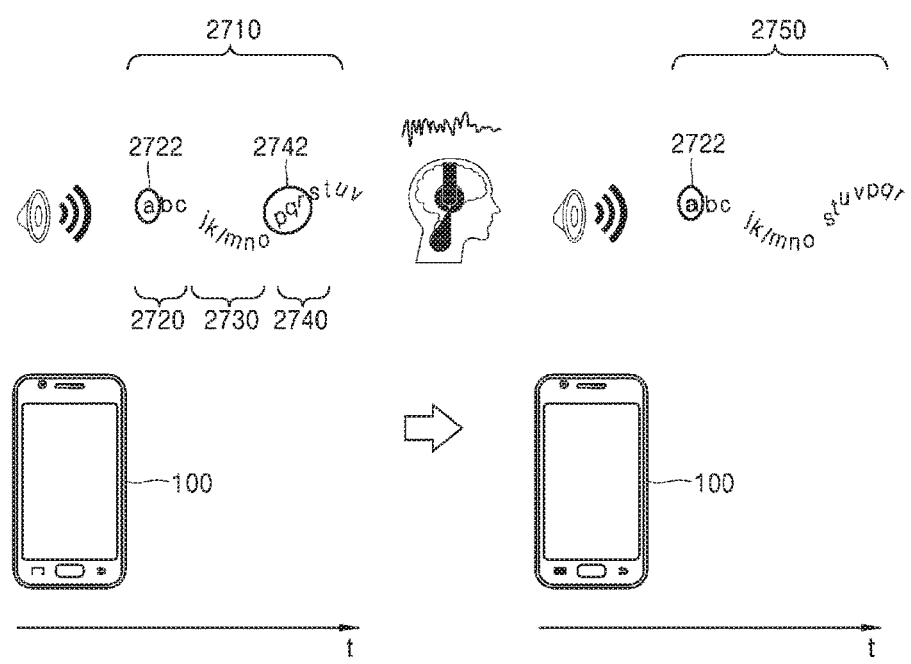
FIG. 27 is a schematic diagram for explaining a method in which the device according to an embodiment of the present invention changes some pieces of objects included in sub-content of selected audio content, based on received brainwave information of a user.

FIG. 27 is a schematic diagram for explaining a method in which the device 100 according to an embodiment of the present invention changes some objects 2722 and 2742 included in pieces of sub-content 2720, 2730, and 2740 of selected audio content 2710, based on received brainwave information of a user.

Referring to FIG. 27, the device 100 may output the selected audio content 2710. The audio content 2710 may include the plurality of pieces of sub-content 2720, 2730, and 2740. Each of the plurality of pieces of sub-content 2720, 2730, and 2740 included in the audio content 2710 may be identified according to an ID value of sub-content included in metadata of the audio content 2710.

When the audio content 2710 is selected, the device 100 may receive brainwave information of the user from the sensing device 10. The device 100 may determine an understanding amount of the user, based on the received brainwave information of the user. For example, the device 100 may determine the understanding amount of the user to be 40 points.

The device 100 may compare the determined understanding amount of the user with an understanding amount threshold for the plurality of pieces of sub-content 2720, 2730, and 2740 of the selected audio content 2710. Herein, it is assumed that the understanding amount threshold is 50 points.

Because the understanding amount of the user does not correspond to the understanding amount threshold, the device 100 may change the some objects 2722 and 2742 included in the pieces of sub-content 2720, 2730, and 2740 of the audio content 2710. The device 100 may change the selected audio content 2710 to correspond to the understanding amount of the user.

The device 100 may search for content changing methods classified for the audio content 2710, from information about pre-stored content changing methods. The device 100 may determine a method of selecting the objects included in sub-content, which is a content changing method corresponding to the determined understanding amount of the user, from among the searched content changing methods. Herein, the objects may be audio data that constitute the sub-content.

The device 100 may change the some objects 2722 and 2742 included in the audio content 2710 according to the determined method. Herein, the device 100 may select the some objects 2722 and 2742 having higher difficulty than the other objects, by referring to difficulty information of the pieces of audio sub-content 2720, 2730, and 2740 from the metadata of the audio content 2710. The method in which the device 100 changes the selected some objects 2722 and 2742 will now be described in detail.

Referring to FIG. 27, the device 100 may change the size of a volume with which the selected first object 2722 is output. For example, the device 100 may increase the size of the volume with which the first object 2722 is output, compared with the sizes of volumes with which the other objects are output. The device 100 may also change a location to which the selected second object 2742 is output.

The device 100 may change the selected objects 2722 and 2742. However, this is only an embodiment, and the method in which the device 100 changes objects included in the selected content 2710 is not limited thereto.

The device 100 may output changed content 2750.

Figure 28:
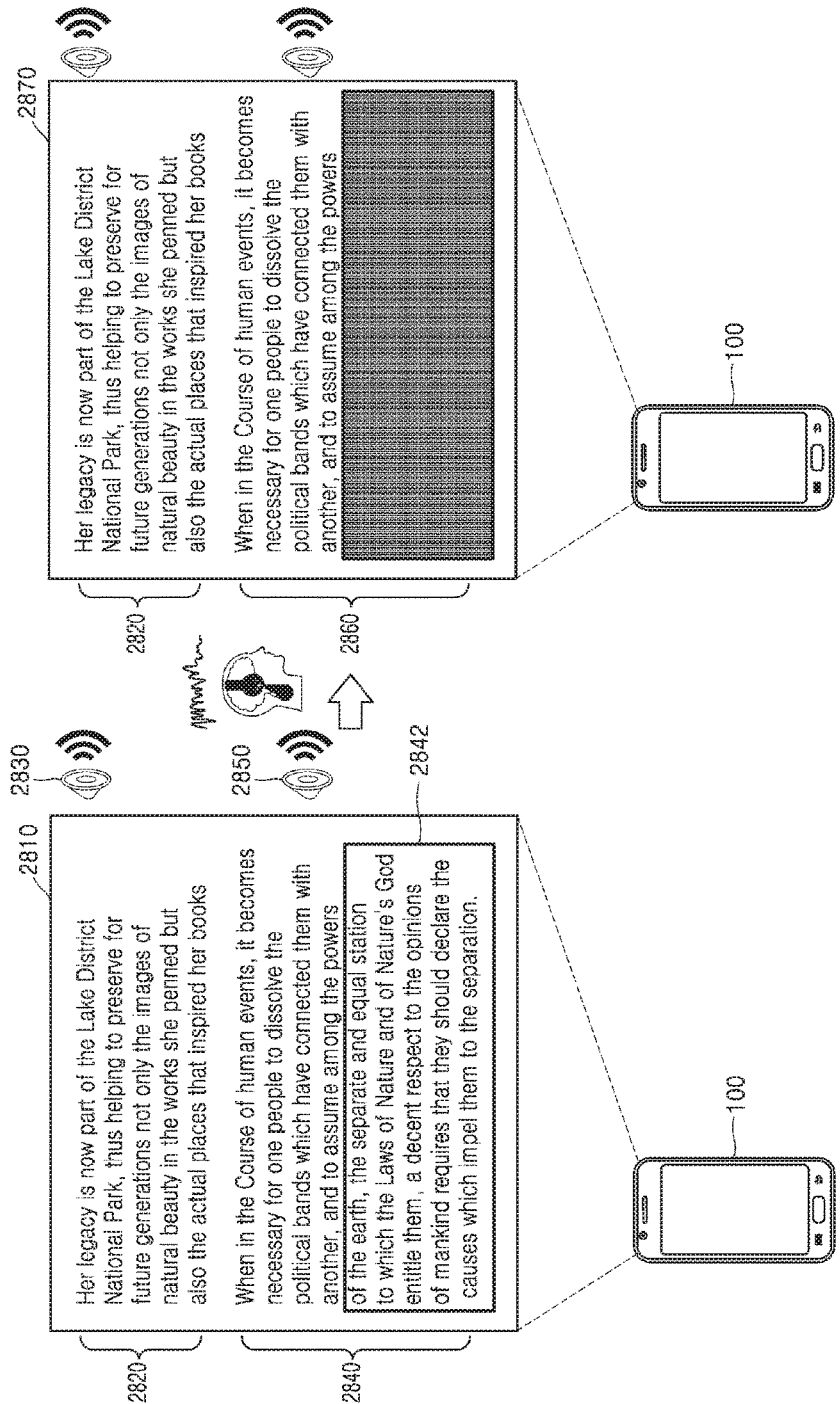
FIG. 28 is a schematic diagram for explaining a method in which the device according to an embodiment of the present invention changes an object included in sub-content of selected multimedia content, based on received brainwave information of a user.

FIG. 28 is a schematic diagram for explaining a method in which the device 100 according to an embodiment of the present invention changes an object 2842 included in sub-content (e.g., sub-content 2840) of selected multimedia content 2810, based on received brainwave information of a user. Herein, the object 2842 may be text data.

Referring to FIG. 28, the device 100 may output the selected multimedia content 2810. The multimedia content 2810 may include a plurality of pieces of sub-content 2820, 2830, 2840, and 2850.

The device 100 may identify each of the plurality of pieces of sub-content according to an ID value of sub-content included in metadata of the multimedia content 2810.

The device 100 may receive brainwave information of the user detected while the sub-content a 2820 and the sub-content b 2830 are being output, from the sensing device 10. The device 100 may determine an understanding amount of the user, based on the received brainwave information of the user. For example, the device 100 may determine the understanding amount of the user to be 70 points.

The device 100 may compare the understanding amount of the user with an understanding amount threshold for the sub-content c 2840 and the sub-content d 2850 of the multimedia content 2810 that are not yet output. Herein, it is assumed that the understanding amount threshold is 50 points.

Because the understanding amount of the user does not correspond to the understanding amount threshold, the device 100 may change some objects (e.g., the object 2842) included in at least one of the sub-content c 2840 and the sub-content d 2850 of the multimedia content 2810. Because the determined understanding amount of the user is higher than the understanding amount threshold, the device 100 may delete some objects of the sub-content c 2840 in order to increase an achievement level with respect to the multimedia content 2810 of the user. For example, the device 100 may delete some text data from the sub-content c 2840 to thereby change the content such that only audio data of the sub-content d 2850 is output for the deleted some text data.

Herein, the device 100 may select the some objects (e.g., the object 2842) having higher difficulty than the other objects, by referring to difficulty information of the pieces of audio sub-content 2820 and 2840 from the metadata of the multimedia content 2810.

The device 100 may change the content 2810 by deleting the selected object 2842. However, this is only an embodi-
ment, and the method in which the device 100 changes objects included in the selected content 2810 is not limited thereto.

The device 100 may output changed content 2860.

FIG. 29 is a schematic diagram for explaining a method in which the device 100 according to an embodiment of the present invention changes an object 2922 included in pieces of sub-content 2920 and 2930 of selected video content 2910, based on received brainwave information of a user. Herein, the object 2922 may be a frame.

Referring to FIG. 29, the device 100 may output the selected video content 2910. The video content 2910 may include a plurality of pieces of video sub-content 2920 and 2930. The video content 2910 may further include text sub-content in addition to the plurality of pieces of video sub-content 2920 and 2930. However, it is assumed that the text sub-content is not output in contrast with the pieces of video sub-content 2920 and 2930.

The device 100 may identify each of the plurality of pieces of video sub-content 2920 and 2930 according to ID values of the plurality of pieces of video sub-content 2920 and 2930 included in metadata of the video content 2910.

The device 100 may receive the brainwave information of the user from the sensing device 10. The device 100 may determine an understanding amount of the user, based on the received brainwave information of the user. For example, the device 100 may determine the understanding amount of the user to be 30 points.

The device 100 may compare the understanding amount of the user with an understanding amount threshold for the video content 2910. Herein, it is assumed that the understanding amount threshold is 40 points. Because the understanding amount of the user does not correspond to the understanding amount threshold, the device 100 may change some objects (e.g., the object 2922) included in the sub-content b 2920 of the video content 2910.

The device 100 according to an embodiment of the present invention may change the content by adding an object 2940 of other sub-content to the object 2922 selected from the sub-content a 2920. For example, the device 100 may change the content 2910 by adding text data 2940 corresponding to a script of the sub-content a 2920 to the selected frame 2944 of the sub-content a 2920.

The device 100 may select some objects (e.g., the object 2922) having higher importance than the other objects, by referring to importance information of the pieces of sub-content 2820 and 2930 from the metadata of the video content 2910.

The device 100 may output changed content 2950.

Figure 30:
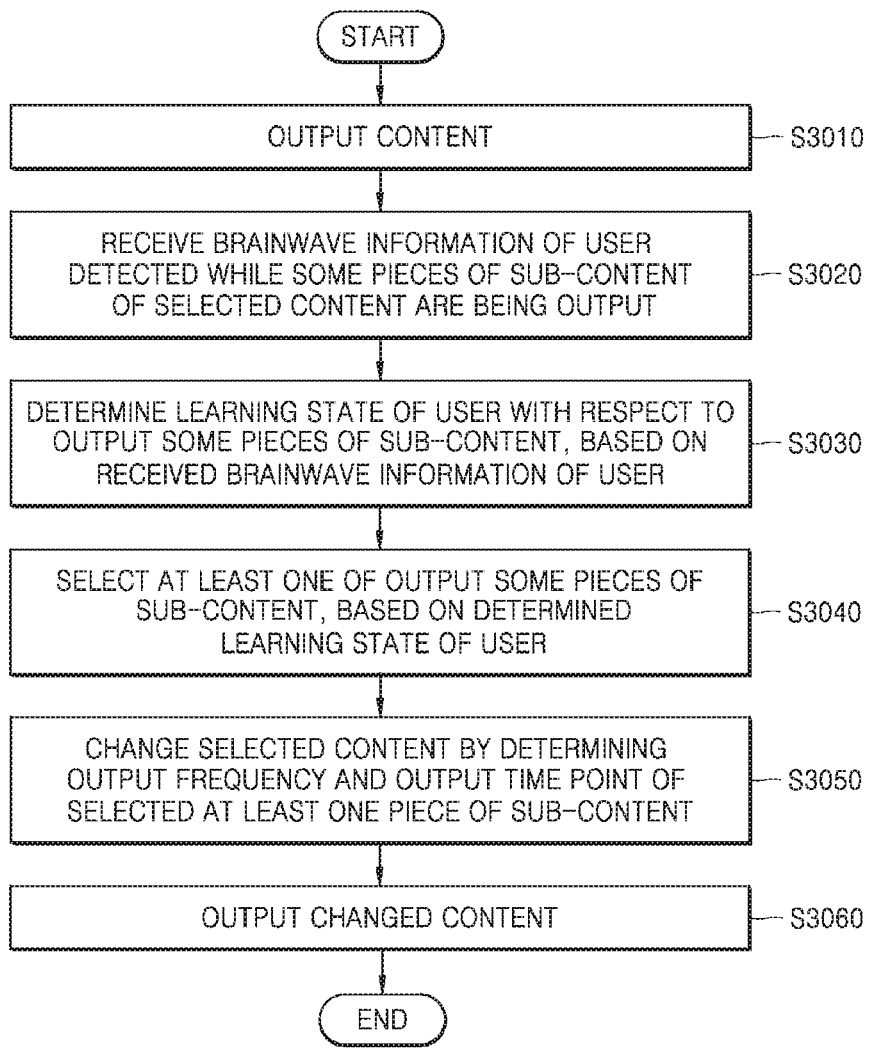
FIG. 30 is a flowchart of a method in which, by using brainwave information of a user detected while some pieces of sub-content included in content are being output, the device according to an embodiment of the present invention determines an output frequency and an output time point of the output some pieces of sub-content.

FIG. 30 is a flowchart of a method in which, by using brainwave information of a user detected while some pieces of sub-content included in content are being output, the device 100 according to an embodiment of the present invention determines an output frequency and an output time point of the output some pieces of sub-content.

In operation S3010, the device 100 may output some of a plurality of pieces of sub-content included in selected content.

The device 100 according to an embodiment of the present invention may select content corresponding to an input of the user from among a plurality of pieces of content. The content may include at least one piece of sub-content. The device 100 may sequentially output the pieces of sub-content included in the selected content according to a preset order.

In operation S3020, the device 100 may receive brainwave information of the user detected while the device 100 is outputting the some pieces of sub-content.

According to an embodiment of the present, when sub-content of the selected content is output, the device 100 may request the sensing device 10 to detect brainwave information of the user. When output of the some pieces of sub-content is completed, the device 100 may request the sensing device 10 for brainwave information of the user with respect to the output-completed some pieces of sub-content.

However, this is merely an embodiment of the present invention, and the device 100 may receive the brainwave information of the user from the sensing device 10 at preset regular intervals.

In operation S3030, the device 100 may determine a learning state of the user with respect to the output some pieces of sub-content, based on the received brainwave information of the user. The learning state of the user may be represented by using at least one of a concentration amount of the user, an understanding amount of the user, a stress amount of the user, and a memorization amount of the user. The device 100 may determine at least one of a concentration amount, an understanding amount, a stress amount, and a memorization amount of the user with respect to the output some pieces of sub-content.

For example, when sub-content a and sub-content b of the selected content are output, the device 100 may determine at least one of a concentration amount, an understanding amount, a stress amount, and a memorization amount of the user with respect to the sub-content a and the sub-content b, based on brainwave information detected while the sub-content a and the sub-content b are being output.

In operation S3040, the device 100 may select at least one of the output some pieces of sub-content, based on the determined learning state of the user.

The device 100 according to an embodiment of the present invention may compare the determined learning state of the user with a threshold for the output some pieces of sub-content. The device 100 may select sub-content for which the learning state of the user does not correspond to the threshold for the output some pieces of sub-content, from among the output some pieces of sub-content. For example, when a memorization amount threshold for the output sub-content a is 30 points and the determined memorization amount with respect to the sub-content a of the user is 15 points, the device 100 may select the sub-content a.

In operation S3050, the device 100 may change the selected content by determining an output frequency and an output time point of the selected at least one piece of sub-content.

The device 100 according to an embodiment of the present invention may repeatedly output the sub-content for which the determined learning state of the user does not correspond to the threshold, from among the output some pieces of sub-content. The device 100 may determine an output frequency and an output time point of the selected sub-content, based on a learning state of the user with respect to the selected sub-content.

For example, when the memorization amount with respect to the sub-content a is 15 points and the memorization amount threshold for the output sub-content a is 30 points, the device 100 may output the sub-content a once after the some pieces of sub-content output by the device 100.

In operation S3060, the device 100 may output changed content.

Operation S3060 may correspond to operation S230 described above with reference to FIG. 2.

The example described above with reference to FIG. 30 is merely an embodiment of the present invention, and the device 100 may output learned content again after the content learning is concluded. Based on the memorization amount of the user, the device 100 may predict a time point when the memorization amount of the user decreases to be less than the memorization amount threshold after the user concludes the content learning. The device 100 may output the content at the moment when the memorization amount of the user is less than the memorization amount threshold.

Figure 31:
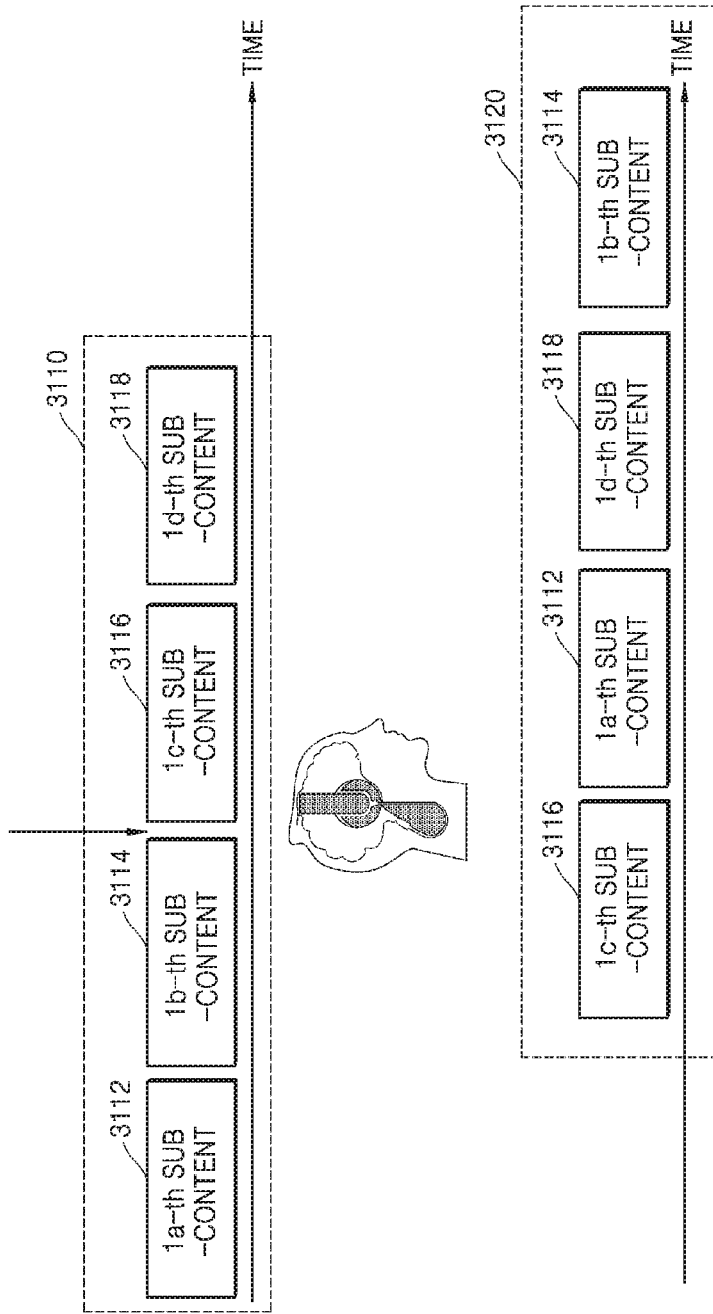
FIG. 31 is a schematic diagram for explaining a method in which, by using brainwave information of a user detected while some pieces of sub-content included in content are being output, the device according to an embodiment of the present invention determines an output frequency and an output time point of the output some pieces of sub-content.

FIG. 31 is a schematic diagram for explaining a method in which, by using brainwave information of a user detected while some pieces of sub-content included in content are being output, the device 100 according to an embodiment of the present invention determines an output frequency and an output time point of the output some pieces of sub-content.

The device 100 according to an embodiment of the present invention may output some pieces of sub-content from among a plurality of pieces of sub-content included in selected content.

The device 100 may select content 3110 corresponding to an input of the user from among a plurality of pieces of content. The content may include at least one piece of sub-content 3112, 3114, 3116, and 3118. The device 100 may sequentially output the pieces of sub-content 3112, 3114, 3116, and 3118 included in the selected content 3110 according to a preset order.

The device 100 may receive brainwave information detected while the 1a-th sub-content 3112 and the 1b-th sub-content 3114 of the selected content 3110 are being output. Every time output of sub-content is completed, the device 100 may request the sensing device 10 to detect brainwave information of the user.

The device 100 may determine a learning state of the user with respect to the output sub-content, based on the received brainwave information of the user. For example, a memorization amount with respect to the 1a-th sub-content 3112 determined based on brainwave information detected while the 1a-th sub-content 3112 is being output may be 30 points. In addition, a memorization amount with respect to the 1b-th sub-content 3114 determined based on brainwave information detected while the 1b-th sub-content 3114 is being output may be 50 points.

The device 100 may predict time points when the user is to forget the 1a-th sub-content 3112 and the 1b-th sub-content 3114, based on difficulty levels and importance levels of the 1a-th sub-content 3112 and the 1b-th sub-content 3114 and the determined memorization amounts. The device 100 may combine and arrange the other pieces of sub-content 3116 and 3118 included in the selected content so that the 1a-th sub-content 3112 and the 1b-th sub-content 3114 are repeatedly output at the predicted time points.

Referring to FIG. 31, the device 100 may insert the 1a-th sub-content 3112 between the 1c-th sub-content 3116 and the 1d-th sub-content 3118 so that the 1a-th sub-content 3112 is output after the 1c-th sub-content 3116, based on the predicted forgetting time point for the 1a-th sub-content 3112. The device 100 may also arrange the pieces of sub-content 3112, 3114, 3116, and 3118 so that the 1b-th sub-content 3114 is output after the 1d-th sub-content 3118, based on the predicted forgetting time point for the 1b-th sub-content 3114.

The device 100 according to an embodiment of the present invention may determine a future learning state of the user, based on brainwave information of the user detected while the 1a-th sub-content 3112 and the 1b-th sub-content 3114 are being output. For example, the device 100 may determine that a future concentration amount of the user is to be 60 points, based on received brainwave information.

The device 100 may compare the determined concentration amount of the user with a concentration amount threshold for the 1c-th sub-content 3116, the 1a-th sub-content 3112, the 1d-th sub-content 3118, and the 1b-th sub-content 3114 which are to be output in the future. When the determined concentration amount of the user is less than the concentration amount threshold, the device 100 may change the pieces of sub-content 3112, 3114, 3116, and 3118 which are to be output in the future. For example, referring to FIG. 31, the device 100 may change the pieces of sub-content 3112, 3114, 3116, and 3118 to correspond to the concentration amount of the user, by deleting some objects of the 1b-th sub-content 3114 having relatively low importance.

The device 100 may output changed content 3120.

Figure 32:
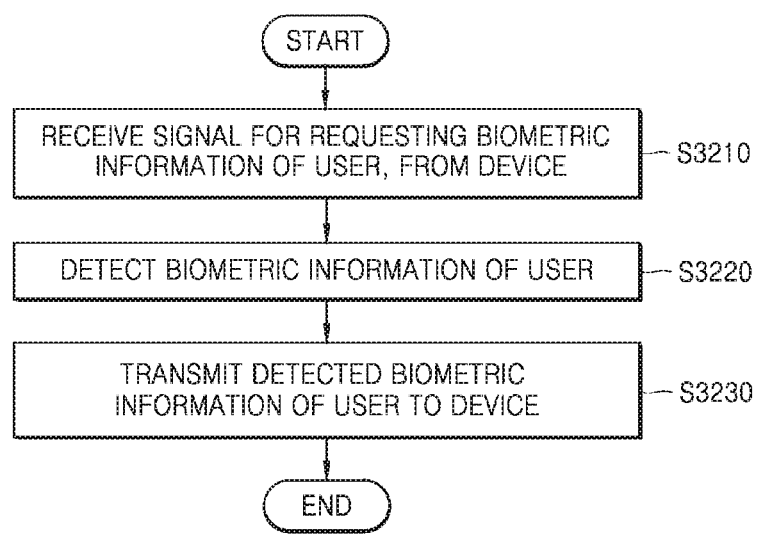
FIG. 32 is a flowchart of a method in which a sensing device according to an embodiment of the present invention detects biometric information of a user.

FIG. 32 is a flowchart of a method in which the sensing device 10 according to an embodiment of the present invention detects biometric information of a user.

In operation S3210, the sensing device 10 may receive a signal for requesting the biometric information of the user, from the device 100.

In operation S3220, the sensing device 10 may detect the biometric information of the user according to a request of the device 100. The sensing device 10 according to an embodiment of the present invention may detect the brainwave information of the user in response to a request from the device 100. When content is selected, the device 100 may request the sensing device 10 for biometric information of the user. When some of a plurality of pieces of sub-content included in selected content are output, the device 100 may request the sensing device 10 for biometric information of the user.

According to another embodiment, the sensing device 10 may detect brainwave information detected at a time point close to a time point when the sensing device 10 has received a request from the device 100, from among brainwave information of the user previously detected at preset intervals.

In operation S3230, the sensing device 10 may transmit the detected biometric information of the user to the device 100. The sensing device 10 may be connected to the device 100 via wired and/or wireless communication. In particular, according to an embodiment of the present invention, the sensing device 10 may be connected to the device 100 via short-range wireless communication. Examples of the short-range wireless communication may include Wi-Fi, NFC, Bluetooth, BLE, ZigBee, WFD, and UWB. For example, the sensing device 10 may transmit the detected brainwave information of the user to the device 100 via Bluetooth.

Figure 33:
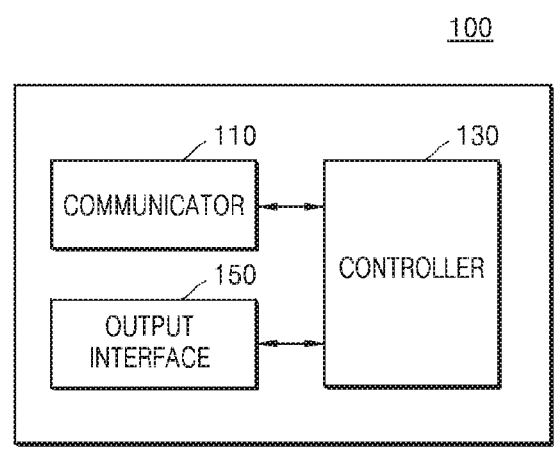
FIG. 33 is a block diagram of a structure of the device according to an embodiment of the present invention.

FIG. 33 is a block diagram of a structure of the device 100 according to an embodiment of the present invention.

Referring to FIG. 33, the device 100 according to an embodiment of the present invention may include a communicator 110, a controller 130, and an output interface 150. However, all of the illustrated components are not essential. The device 100 may be implemented by more or less components than those illustrated in FIG. 33.

The communicator 110 receives biometric information of a user.

The communicator 110 according to an embodiment of the present invention may transmit a signal for requesting the biometric information of the user to the sensing device 10. For example, when content is selected by the device 100, the communicator 110 may transmit a signal for requesting the brainwave information of the user to the sensing device 10. The communicator 110 may transmit a signal for requesting biometric information of the user detected by the sensing device 10 while some pieces of sub-content included in selected content are being output. The communicator 110 may receive the biometric information of the user from the sensing device 10 in response to the request.

As another example, the communicator 110 may receive the biometric information of the user from the sensing device 10 at preset regular intervals.

The controller 130 may determine at least one of a concentration amount, an understanding amount, a stress amount, and a memorization amount of the user, by using the obtained biometric information of the user. For example, based on brainwave information of the user obtained while the some pieces of sub-content of the selected content are being output, the controller 130 may determine a concentration degree, an understanding degree, and a stress degree of the user with respect to the output some pieces of sub-content. The controller 130 may determine the concentration amount, the understanding amount, the stress amount, and the memorization amount by using at least one of the determined concentration degree, the determined understanding degree, and the determined stress degree.

The controller 130 may change at least one piece of sub-content included in content selected by the device, according to a determined learning state of the user.

The controller 130 according to an embodiment of the present invention may select at least one of sub-content included in the selected content and sub-content included in other content, based on the determined learning state of the user.

For example, when the determined learning state of the user does not correspond to a threshold required to learn the selected content, the controller 130 may select some of the pieces of sub-content included in the selected content.

According to another embodiment, when the determined learning state of the user does not correspond to the threshold necessary for learning the selected content, the controller 130 may select the sub-content included in the selected content and the sub-content included in the other content.

The controller 130 may change the selected at least one piece of sub-content, based on the determined learning state of the user. For example, the controller 130 may change at least one of the shapes, colors, sizes, and locations of objects included in the selected at least one piece of sub-content. The objects may include at least one of a frame, image data, text data, and audio data.

According to an embodiment of the present invention, the controller 130 may change at least one of a frame, image data, text data, and audio data included in the sub-content of the selected content.

According to another embodiment of the present invention, the controller 130 may change at least one of a frame, an image, and a text included in both the sub-content of the selected content and the sub-content of the other content.

The controller 130 may change the selected content by arranging changed at least one piece of sub-content, based on the determined learning state of the user. When a plurality of pieces of sub-content are selected and changed, the controller 130 may change the selected content by arranging a changed plurality of pieces of sub-content.

Figure 34:
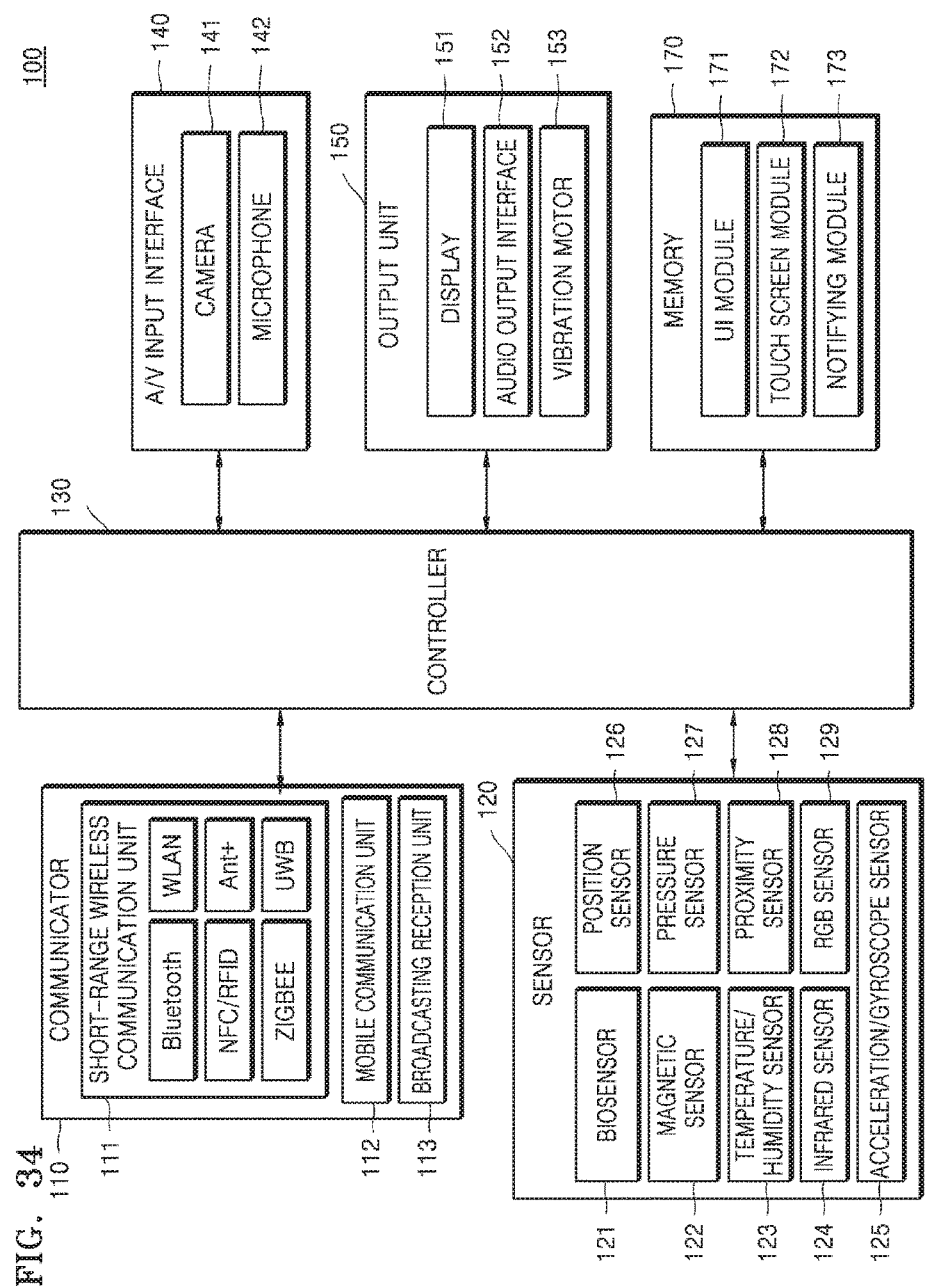
FIG. 34 is a block diagram of a structure of a device according to another embodiment of the present invention.

FIG. 34 is a block diagram of a structure of the device 100 according to another embodiment of the present invention.

For example, as illustrated in FIG. 34, the device 100 according to an embodiment of the present invention may include a communicator 110, a sensor 120, a controller 130, an audio/video (A/V) input interface 140, an output interface 150, a user input interface 160, and a memory 170.

The aforementioned components will now be described in detail.

The communicator 110 may include at least one component that enables the device 100 to perform data communication with the sensing device 10 or an external device (not shown). For example, the communicator 110 may include a short-range wireless communication unit 111, a mobile communication unit 112, and a broadcasting reception unit 113.

The short-range wireless communication unit 111 may include, but is not limited to, a Bluetooth communicator, a BLE communicator, an NFC unit, a wireless local area network (WLAN) (e.g., Wi-Fi) communicator, a ZigBee communicator, an infrared Data Association (IrDA) communicator, a WFD communicator, an UWB communicator, an Ant+ communicator, and the like.

The mobile communication unit 112 may exchange a wireless signal with at least one selected from a base station, an external terminal, and a server on a mobile communication network. Here, examples of the wireless signal may include a voice call signal, a video call signal, and various types of data according to text/multimedia messages transmission.

The broadcasting reception unit 113 receives a broadcasting signal and/or broadcasting-related information from an external source via a broadcasting channel. The broadcasting channel may be a satellite channel, a ground wave channel, or the like. According to embodiments, the device 100 may not include the broadcasting reception unit.

The sensor 120 may sense the status of the device 100 or the status of the surrounding of the device 100 and may transmit information corresponding to the sensed status to the controller 130.

When the device 100 executes content, the sensor 120 obtains the biometric information of a user who uses the executed content, and context information representing a situation of a user at the moment when the biometric information of the user has been obtained.

The sensor 120 may include, but is not limited thereto, at least one selected from a biosensor 121, a magnetic sensor 122, an acceleration/gyroscope sensor 123, a temperature/humidity sensor 124, an infrared sensor 125, a position sensor (e.g., a global positioning system (GPS)) 126, a pressure sensor 127, a proximity sensor 128, and an RGB sensor 129 (i.e., an illuminance sensor).

The biosensor 121 may detect the biometric information of the user. For example, the biosensor 121 may detect the brainwave information of the user by using an EEG sensor included therein.

In response to an input of the user of selecting one from a plurality of pieces of content, the biosensor 121 may detect brainwave information of the user. As another example, the biosensor 121 may detect brainwave information of the user while some pieces of sub-content of the content selected based on the\a user input are being output.

The biosensor 121 according to an embodiment of the present invention may include an EEG sensor, a pulse wave sensor, an ECG sensor, and an iris sensor. However, this is merely an embodiment of the present invention, and the present invention is not limited thereto.

Functions of most of the sensors included in the sensor 120 would be instinctively understood by one of ordinary skill in the art in view of their names and thus detailed descriptions thereof will be omitted herein.

The controller 130 typically controls all operations of the device 100. For example, the controller 130 may control the communicator 110, the sensor 120, the A/V input interface 140, the output interface 150, the user input unit 160, and the memory 170 by executing programs stored in the memory 170.

The controller 130 of FIG. 34 may correspond to the controller 130 of FIG. 33.

The A/V input unit 140 inputs an audio signal or a video signal, and may include a camera 141 and a microphone 142. The camera 141 may acquire an image frame, such as a still image or a moving picture, via an image sensor in a video call mode or a photography mode. An image captured via the image sensor may be processed by the controller 130 or a separate image processor (not shown).

The image frame obtained by the camera 141 may be stored in the memory 170 or transmitted to the outside via the communicator 110. At least two cameras 141 may be included according to embodiments of the structure of a terminal.

The microphone 142 receives an external audio signal and converts the external audio signal into electrical audio data. For example, the microphone 142 may receive an audio signal from an external device or a speaking person. The microphone 142 may use various noise removal algorithms in order to remove noise that is generated while receiving the external audio signal.

The output interface 150 is used to perform an operation determined by the controller 130, and may include a display 151, an audio output interface 152, and a vibration motor 153.

The display 151 outputs information that is processed by the device 100. For example, the display 151 may display selected content. The display 151 may output changed content. When the display 151 forms a layer structure together with a touch pad to construct a touch screen, the display 151 may be used as an input device as well as an output device. The display 151 may include at least one of a liquid crystal display (LCD), a thin film transistor-liquid crystal display (TFT-LCD), an organic light-emitting diode (OLED), a flexible display, a 3D display, and an electrophoretic display. According to embodiments of the device 100, the device 100 may include at least two displays 151. The at least two displays 151 may be disposed to face each other by using a hinge.

The audio output interface 152 outputs audio data that is received from the communicator 110 or stored in the memory 170. The audio output interface 152 may also output an audio signal (for example, a call signal receiving sound, a message receiving sound, a notification sound) related with a function of the device 100. The audio output interface 152 may include, for example, a speaker and a buzzer.

The vibration motor 153 may output a vibration signal. For example, the vibration motor 153 may output a vibration signal corresponding to an output of audio content or video content (for example, a call signal receiving sound or a message receiving sound). The vibration motor 153 may also output a vibration signal when a touch screen is touched.

The user input interface 160 denotes means via which a user inputs data for controlling the device 100. For example, the user input interface 160 may be, but is not limited to, a key pad, a dome switch, a touch pad (e.g., a capacitive overlay type, a resistive overlay type, an infrared beam type, an integral strain gauge type, a surface acoustic wave type, a piezo electric type, or the like), a jog wheel, or a jog switch.

The user input interface 160 may obtain a user input. For example, the user input interface 160 may obtain a user input that selects at least one of a plurality of pieces of content that may be output by the device 100.

The memory 170 may store a program for processing and control of the controller 130, and may store input/output data (for example, a plurality of pieces of content, content changed based on selected content, and brainwave information of the user).

The memory 170 may store biometric information of the user. The memory 170 may store information about content changing methods according to learning states of the user. The memory 170 may store information about other content that is combined with the selected content to efficiently improving the learning state of the user.

The memory 170 may include at least one type of storage medium selected from among a flash memory type, a hard disk type, a multimedia card micro type, a card type memory (for example, a secure digital (SD) or extreme digital (XD) memory), a random access memory (RAM), a static random access memory (SRAM), a read-only memory (ROM), an electrically erasable programmable ROM (EEPROM), a programmable ROM (PROM), magnetic memory, a magnetic disk, and an optical disk. The device 100 may operate a web storage or a cloud server on the internet which performs a storage function of the memory 170.

The programs stored in the memory 170 may be classified into a plurality of modules according to their functions, for example, a user interface (UI) module 171, a touch screen module 172, and a notification module 173.

The UI module 71 may provide a UI, graphical user interface (GUI), or the like that is specialized for each application and interoperates with the device 100. The touch screen module 172 may detect a touch gesture on a touch screen of a user and transmit information regarding the touch gesture to the controller 130. The touch screen module 172 according to an embodiment of the present invention may recognize and analyze a touch code. The touch screen module 172 may be configured by separate hardware including a controller.

In order to detect the actual touch or the proximate touch on the touch pad, the touch screen may internally or externally have various sensors. An example of a sensor used to detect a real touch or a proximity touch on the touch panel 400 is a tactile sensor. The tactile sensor denotes a sensor that detects a touch by a specific object to a degree to which a human feels or more. The tactile sensor may detect various types of information, such as the roughness of a touched surface, the hardness of the touching object, and the temperature of a touched point.

Another example of a sensor used to detect the real touch or the proximity touch on the touch screen is a proximity sensor.

The proximity sensor senses the existence of an object that approaches the predetermined sensing surface or an object that exists nearby, without mechanical contact, by using an electromagnetic force or infrared rays. Examples of the proximity sensor include a transmission-type photoelectric sensor, a direct reflection-type photoelectric sensor, a mirror reflection-type photoelectric sensor, a high frequency oscillation-type proximity sensor, a capacity-type proximity sensor, a magnetic proximity sensor, and an infrared-type proximity sensor. Examples of the touch gesture of the user may include tap, touch and hold, double tap, drag, panning, flick, drag and drop, swipe, and the like.

The notification module 173 may generate a signal for notifying that an event has been generated in the device 100. Examples of the event generated in the device 100 may include call signal receiving, message receiving, a key signal input, schedule notification, and obtainment of a user input. The notification module 173 may output a notification signal in the form of a video signal via the display 151, in the form of an audio signal via the audio output interface 152, or in the form of a vibration signal via the vibration motor 153.

Figure 35:
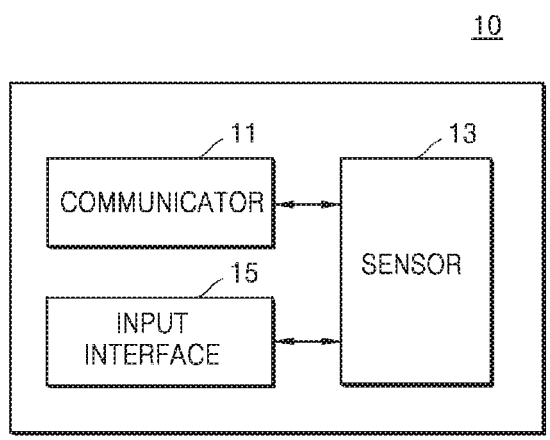
FIG. 35 is a block diagram of the sensing device according to an embodiment of the present invention.

FIG. 35 is a block diagram of the sensing device 10 according to an embodiment of the present invention.

Referring to FIG. 35, the sensing device 10 according to an embodiment of the present invention may include a communicator 11, a sensor 13, and an input interface 15. However, all of the illustrated components are not essential. The sensing device 10 may be implemented by more or less components than those illustrated in FIG. 35.

The aforementioned components will now be described in detail.

The communicator 11 may receive a signal for requesting the biometric information of the user, from the device 100. The communicator 11 may be connected to the device 100 via wires or wirelessly. In particular, according to an embodiment of the present invention, the communicator 11 may be connected to the device 100 via short-range wireless communication. Examples of the short-range wireless communication may include Wi-Fi, NFC, Bluetooth, BLE, Zig-Bee, WFD, and UWB.

The sensor 13 may detect the biometric information of the user according to a request of the device 100. The sensor 13 according to an embodiment of the present invention may detect the brainwave information of the user in response to a request from the device 100. For example, when content is selected by the device 100, the sensor 13 may detect brainwave information of the user. When some of a plurality of pieces of sub-content included in selected content are output, the sensor 13 may detect brainwave information of the user.

According to another embodiment, the sensor 13 may detect brainwave information detected at a time point close to a time point when the sensing device 10 has received a request from the device 100, from among brainwave information of the user previously detected at preset intervals. The detected biometric information of the user may be transmitted to the device 100 via the communicator 11.

The sensor 13 may include, but is not limited to, biosensors, such as an EEG sensor, a pulse wave sensor, and an ECG sensor.

The input interface 15 may receive a user unit for controlling the sensing device 10 to be turned on or off. The input interface 15 according to an embodiment of the present invention may receive, from the user, an input signal for requesting the brainwave information of the user to be detected, and transmit the received input signal to the sensor 13.

The sensing device 10 according to an embodiment may be realized in various types. For example, the sensing device 10 may be, but is not limited to, a smart watch, smart glasses, or a Bluetooth headphone. As another example, the sensing device 10 may be of a chip type attachable to glasses, headphones, and the like that do not support an IoT function. However, this is merely an embodiment, and the sensing device 10 may be realized in any type that is attachable to other things. The sensing device 10 may be attached to a thing close to a portion of the body of the user from which brainwaves are detected, and may detect the brainwave information of the user.

Figure 36:
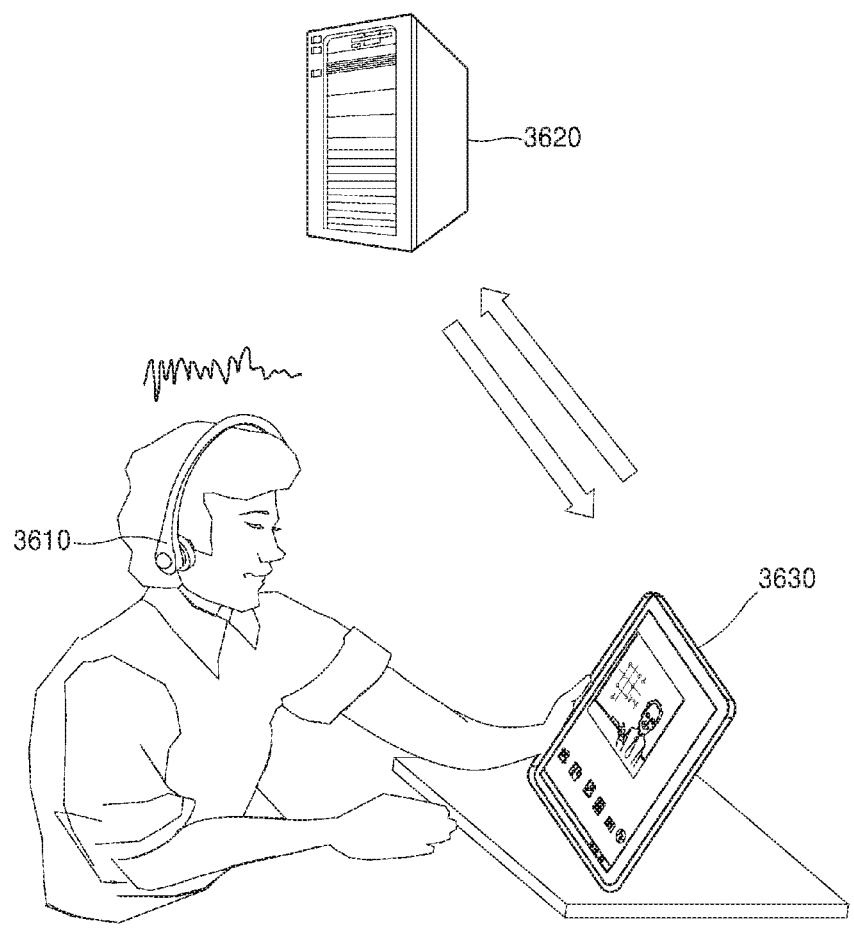
FIG. 36 is a conceptual diagram for describing a system for providing content, according to another embodiment of the present invention.

FIG. 36 is a conceptual diagram for describing a system 3600 for providing content, according to another embodiment of the present invention.

As shown in FIG. 36, the content providing system 3600 according to an embodiment of the present invention may include a sensing device 3610, a server 3620, and a device 3630. However, all of the illustrated components are not essential. The content providing system 3600 may be implemented by more or less components than those illustrated in FIG. 36.

The aforementioned components will now be described in detail.

The sensing device 3610 according to an embodiment of the present invention may detect biometric information of a user. The sensing device 3610 may be realized in various types. The sensing device 3610 according to an embodiment of the present invention may include an input device, a sensing device, an output device, and a control device. Examples of the sensing device 3610 may include, but are not limited to, a smart watch, smart glasses, a Bluetooth headphone, and an HMD. The sensing device may include, but is not limited to, biosensors, such as an EEG sensor, a pulse wave sensor, and an ECG sensor.

As another example, the sensing device 3610 may be of a chip type attachable to glasses, headphones, and the like that do not support an IoT function. However, this is merely an embodiment, and the sensing device 3610 may be realized in any type that is attachable to other things. The sensing device 3610 may be attached to a thing close to a portion of the body of the user from which brainwaves are detected, and may detect brainwave information of the user.

In response to a signal for requesting biometric information of the user to be detected, the sensing device 3610 according to an embodiment of the present invention may detect the biometric information of the user. The signal for requesting biometric information of the user to be detected may be generated by a user input. However, this is merely an embodiment, and the sensing device 3610 may receive the signal for requesting biometric information of the user to be detected, from the device 3630 capable of receiving a user input. According to another embodiment, the sensing device 3610 may detect the biometric information of the user at preset regular intervals.

The sensing device 3610 according to an embodiment of the present invention may transmit the detected biometric information of the user to the server 3620. The sensing device 3610 may transmit user ID information capable of identifying the user together with the biometric information of the user to the server 3620.

The server 3620 according to an embodiment of the present invention may determine a learning state of the user, based on the received biometric information of the user. For example, the server 3620 may determine at least one of a concentration amount, an understanding amount, a stress amount, and a memorization amount of the user, by statistically analyzing the received brainwave information of the user.

As another example, the server 3620 may compare the received brainwave information of the user with a plurality of brainwave patterns previously-stored for the user and thus may determine at least one of a concentration amount, an understanding amount, a stress amount, and a memorization amount of the user represented by a corresponding brainwave pattern as the learning state of the user.

The server 3620 may change content selected by the device 3630, according to the determined learning state of the user. The server 3620 may previously receive information about the content selected by the device 3630, via communication with the device 3630. The server 3620 may select one from a plurality of stored pieces of content, based on the received information. The server 3620 may change the selected content according to the learning state of the user.

Figure 39:
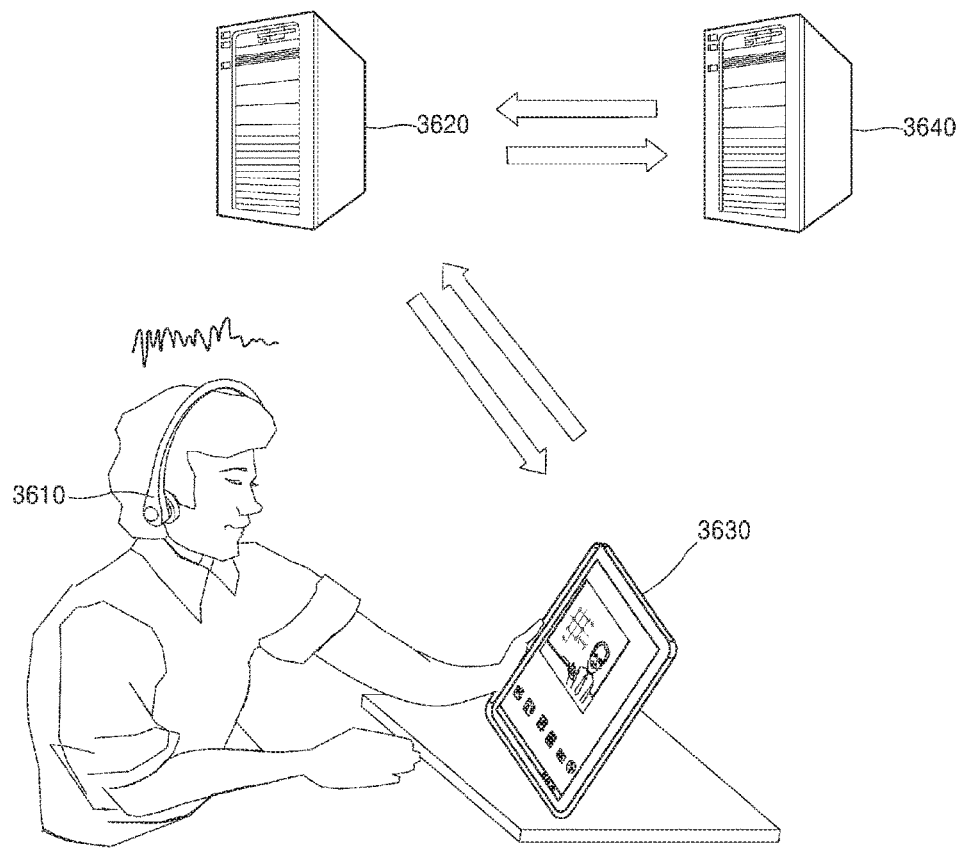
FIG. 39 is a conceptual diagram for describing a system for providing content, according to another embodiment of the present invention.

As another example, the server 3620 may stream content provided by a content providing server 3640 of FIG. 39 and output streamed content to the device 3630. The server 3620 may change the streamed content according to the determined learning state of the user. This will now be described in greater detail with reference to FIG. 39. The server 3620 according to an embodiment of the present invention may transmit changed content to the device 3630.

The device 3630 according to an embodiment of the present invention may output the changed content received from the server 3620. While the device 3630 is outputting the changed content, the sensing device 3610 may detect brainwave information of the user who learns the changed content. The sensing device 3610 may transmit the detected brainwave information to the server 3620. The server 3620 may re-change the changed content by re-determining a learning state of the user based on the received brainwave information.

Figure 37:
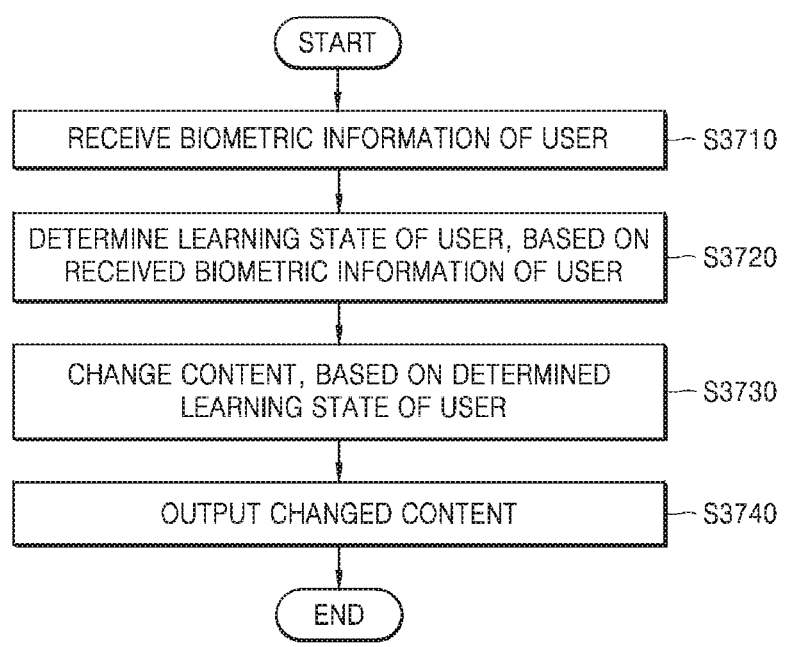
FIG. 37 is a flowchart of a method in which a server according to another embodiment of the present invention provides content to a user, based on received biometric information of the user.

FIG. 37 is a flowchart of a method in which the server 3620 according to another embodiment of the present invention provides content to a user, based on received biometric information of the user.

In operation S3710, the server 3620 may receive the biometric information of the user.

In operation S3720, the server 3620 may determine a learning state of the user, based on the received biometric information of the user. The server 3620 according to an embodiment of the present invention may receive, from the sensing device 3610, biometric information of the user detected by the sensing device 3610.

The server 3620 may determine at least one of a concentration amount, an understanding amount, a stress amount, and a memorization amount of the user, by using received brainwave information of the user. For example, based on brainwave information of the user obtained while some pieces of sub-content of selected content are being output, the server 3620 may determine a concentration degree, an understanding degree, and a stress degree of the user with respect to the output some pieces of sub-content. The server 3620 may determine the concentration amount, the understanding amount, the stress amount, and the memorization amount by using at least one of the determined concentration degree, the determined understanding degree, and the determined stress degree.

In operation S3730, the server 3620 may change at least one piece of sub-content included in content selected by the device 3630, according to the determined learning state of the user.

The server 3620 may previously store information about a threshold representing a learning state of the user required to learn the selected content. The threshold may be at least one of a preset concentration amount, a preset understanding amount, a preset stress amount, and a preset memorization amount.

The server 3620 may compare the learning state of the user with the threshold for the selected content. When the learning state of the user does not correspond to the threshold, the server 3620 may change at least one piece of sub-content included in the selected content. For example, when the learning state of the user does not satisfy the threshold, the server 3620 may change the selected content by selecting some of a plurality of pieces of sub-content included in the selected content. As another example, the server 3620 may change the selected content by adding sub-content included in other content to sub-content included in the selected content. However, this is only an embodiment, and the method of changing the content is not limited thereto.

In operation S3740, the server 3620 may transmit changed content to the device 3630. The server 3620 according to an embodiment of the present invention may transmit metadata about at least one piece of sub-content included in the changed content, together with the changed content. For example, the server 3620 may transmit information about a time period taken until output of the changed content is completed, together with the changed content, to the device 3630.

The aforementioned example is merely an embodiment of the present invention, and the server 3620 may transmit only the changed content to the device 3630.

Figure 38:
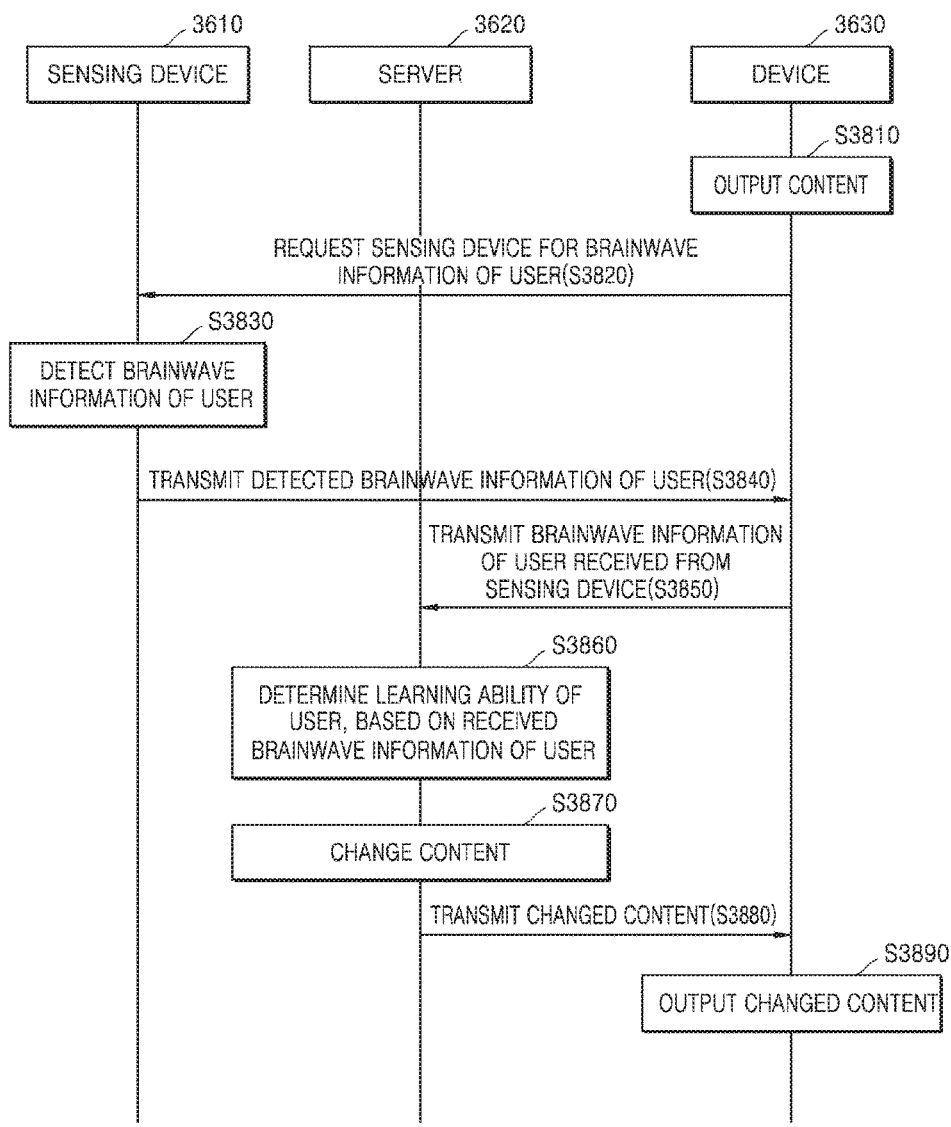
FIG. 38 is a flowchart for explaining a system for providing changed content, according to another embodiment of the present invention.

FIG. 38 is a flowchart for describing the system 3600 for providing content, according to another embodiment of the present invention.

In operation S3810, the device 3630 may select one of a plurality of pieces of content that may be output by the device 3630, based on an input of a user.

The device 3630 according to an embodiment of the present invention may display ID information representing each of the plurality of pieces of content on a screen of the device 3630. For example, the device 3630 may display an icon, an image, and a text representing each of the plurality of pieces of content on the screen of the device 3630. The device 3630 may select content indicated by ID information corresponding to the input of the user from among the displayed ID information representing each of the plurality of pieces of content.

As another example, the device 3630 may select content by receiving a voice input of the user.

In operation S3820, as content is selected, the device 3630 may request the sensing device 3610 for brainwave information of the user.

The device 3630 according to an embodiment of the present invention may transmit a signal requesting the sensing device 3610 connected to the device 3630 for the brainwave information of the user. The signal that requests the brainwave information may include, for example, authentication information representing that the device 3630 of the user has transmitted the signal that requests the brainwave information.

In operation S3830, the sensing device 3610 may detect the brainwave information of the user.

The sensing device 3610 according to an embodiment of the present invention may detect the brainwave information of the user as the sensing device 3610 receives the signal for requesting the brainwave information from the device 3630. For example, the sensing device 3610 may detect the brainwave information of the user from an EEG sensor included therein. As another example, when previously-detected brainwave information of the user exists, the sensing device 3610 may detect biometric information detected within a specific time period range from the moment when the sensing device 10 receives the signal for requesting the brainwave information.

In operation S3840, the sensing device 3610 may transmit the detected brainwave information of the user to the device 3630. The sensing device 3610 according to an embodiment of the present invention may transmit ID information representing the user, together with the brainwave information of the user, to the device 3630. However, this is merely an embodiment of the present invention, and the sensing device 3610 may transmit the detected brainwave information of the user to the server 3620. This will be described in greater detail later with reference to FIG. 39.

In operation S3850, the device 3630 may transmit the brainwave information of the user received from the sensing device 3610 to the server 3620.

In operation S3860, the server 3620 may determine a learning state of the user, based on the received brainwave information of the user. The server 3620 according to an embodiment of the present invention may determine at least one of a concentration amount, an understanding amount, a stress amount, and a memorization amount of the user, based on the received brainwave information of the user.

The method in which the server 3620 determines the learning state of the user may correspond to the method described above with reference to FIGS. 2-31 in which the device 100 determines the learning state of the user.

In operation S3870, the server 3620 may change the selected content by changing at least one piece of sub-content included in the selected content according to the determined learning state of the user. The server 3620 according to an embodiment of the present invention may change the selected content by changing at least one piece of sub-content included in the selected content or adding at least one piece of sub-content included in other content to the at least one piece of sub-content included in the selected content.

The method in which the server 3620 changes content may correspond to the method described above with reference to FIGS. 2-31 in which the device 100 changes content.

In operation S3880, the server 3620 may transmit changed content to the device 3630. Operation S3880 may correspond to operation S3740 described above with reference to FIG. 37.

In operation S3890, the device 3630 may output changed content.

FIG. 39 is a conceptual diagram for describing a system 3900 for providing content, according to another embodiment of the present invention.

As shown in FIG. 39, the content providing system 3900 according to an embodiment of the present invention may include a sensing device 3910, a server 3920, a device 3930, and the content providing server 3940. However, all of the illustrated components are not essential. The content providing system 3900 may be implemented by more or less components than those illustrated in FIG. 39.

The aforementioned components will now be described in detail.

The sensing device 3910 according to an embodiment of the present invention may detect biometric information of a user. The sensing device 3910 may be realized in various types. For example, the sensing device 3910 may be, but is not limited to, a smart watch, smart glasses, a Bluetooth headphone, or an HMD. As another example, the sensing device 3910 may be of a chip type attachable to glasses, headphones, and the like that do not support an IoT function.

The sensing device 3910 according to an embodiment of the present invention may transmit the detected biometric information of the user to the server 3920.

The sensing device 3910 may correspond to the sensing device 3610 described above with reference to FIG. 36.

The server 3920 according to an embodiment of the present invention may receive content from the content providing server 3940 and stream the received content to the device 3930. The content providing server 3940 is a server operated in a content provider, and may store manufactured content. The content providing server 3940 may transmit content requested by the server 3920 to the server 3920.

In addition, when a user of the device 3930 is authenticated as a pre-registered user, the server 3920 may receive content from the content providing server 3940 and stream the received content to the device 3930.

The device 3930 according to an embodiment of the present invention may output changed content received from the server 3920. The device 3930 may correspond to the device 3630 described above with reference to FIG. 36.

Figure 40:
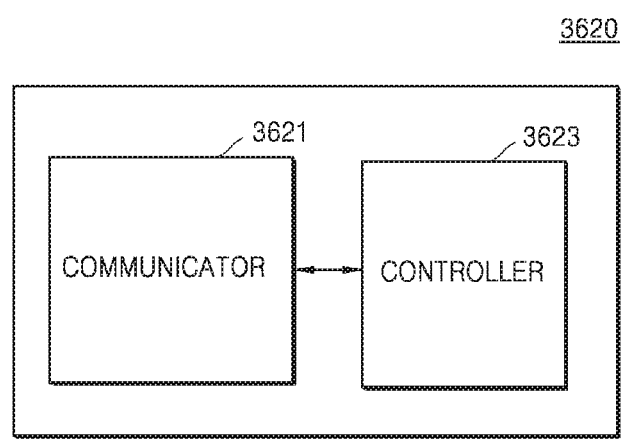
FIG. 40 is a block diagram of a content providing server according to another embodiment of the present invention.

FIG. 40 is a block diagram of a content providing server 3620 according to another embodiment of the present invention.

Referring to FIG. 40, the content providing server 3620 may include a communicator 3621 and a controller 3623. However, all of the illustrated components are not essential. The content providing server 3620 may be implemented by more or less components than those illustrated in FIG. 40.

The aforementioned components will now be described in detail.

The communicator 3621 may determine a learning state of a user, based on obtained biometric information of the user. The communicator 3621 according to an embodiment of the present invention may receive, from the device 3630, biometric information of the user detected by the sensing device 3610. However, this is merely an embodiment, and the communicator 3621 may receive a biometric signal from the sensing device 3620.

The controller 3623 may determine at least one of a concentration amount, an understanding amount, a stress amount, and a memorization amount of the user, by using received brainwave information of the user. For example, based on brainwave information of the user obtained while some pieces of sub-content of selected content are being output, the controller 3623 may determine a concentration degree, an understanding degree, and a stress degree of the user with respect to the output some pieces of sub-content. The controller 3623 may determine the concentration amount, the understanding amount, the stress amount, and the memorization amount by using at least one of the determined concentration degree, the determined understanding degree, and the determined stress degree.

The controller 3623 may determine at least one of the concentration amount, the understanding amount, the stress amount, and the memorization amount of the user, based on the received brainwave information of the user, according to the method described above with reference to FIGS. 2-31.

The controller 3623 may change at least one piece of sub-content included in content selected by the device 3630, according to the determined learning state of the user. The controller 3623 may previously store information about a threshold representing a learning state of the user required to learn the selected content.

The controller 3623 may compare the learning state of the user with the threshold for the selected content. When the learning state of the user does not correspond to the threshold, the controller 3623 may change at least one piece of sub-content included in the selected content. For example, when the learning state of the user does not satisfy the threshold, the server 3623 may select some of a plurality of pieces of sub-content included in the selected content. As another example, the controller 3623 may change the selected content by adding sub-content included in other content to sub-content included in the selected content. However, this is only an embodiment, and the method of changing content is not limited thereto.

The communicator 3621 may transmit changed content to the device 3630. The communicator 3621 according to an embodiment of the present invention may transmit metadata about at least one piece of sub-content included in the changed content, together with the changed data, to the device 3630.

Figure 41:
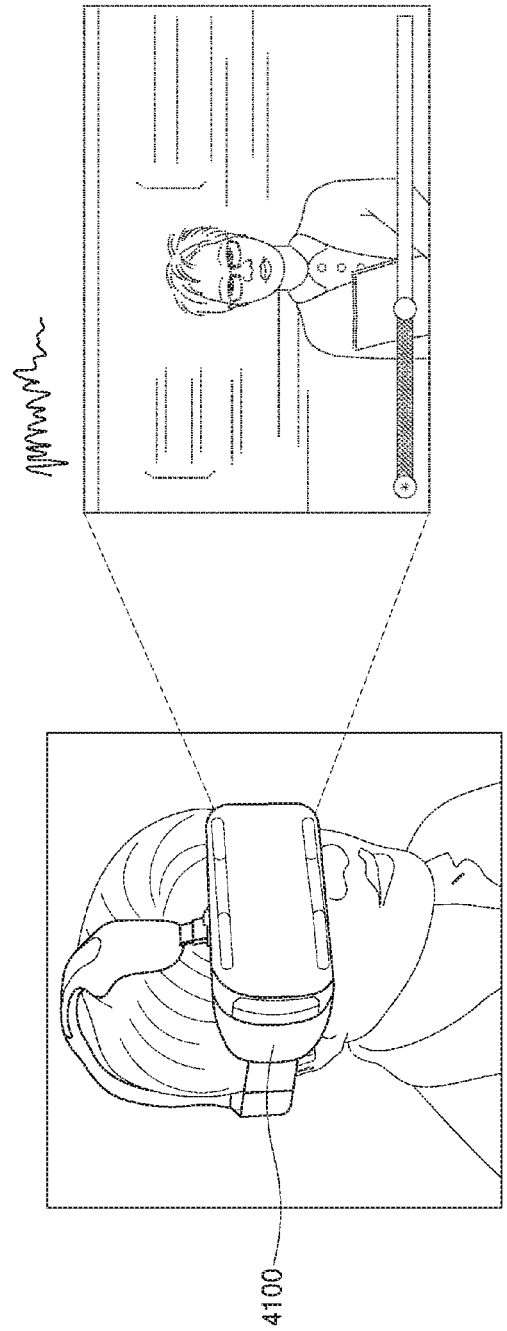
FIG. 41 is a conceptual diagram for describing a method in which a sensing device according to another embodiment of the present invention provides content.

FIG. 41 is a conceptual diagram for describing a method in which a sensing device 4100 according to another embodiment of the present invention provides content.

The sensing device 4100 may be realized in various types. The sensing device 4100 according to an embodiment of the present invention may include an input device, an output device, a control device, and the like. Examples of the sensing device 4100 may include, are not limited to, a smart watch, smart glasses, a Bluetooth headphone, and a HMD. Examples of the sensing device 4100 may further include, but are not limited to, biosensors, such as an EEG sensor, a pulse wave sensor, and an ECG sensor.

The sensing device 4100 according to an embodiment of the present invention may output content. At this time, the sensing device 4100 may select content that is to be output, based on a user input.

The sensing device 4100 may detect biometric information of a user via a sensor included therein. The sensing device 4100 may determine a learning state of the user, based on the detected biometric information of the user. The learning state of the user may be represented based on at least one of a concentration amount of the user, an understanding amount of the user, a stress amount of the user, and a memorization amount of the user.

The sensing device 4100 may change the selected content according to the determined learning state of the user in order to efficiently provide information included in the selected content to the user. The learning state of the user may include at least one of a learning state with respect to sub-content of the output content and a learning state with respect to sub-content of content that is to be output in the future.

When the learning state of the user does not correspond to a threshold for the selected content, the sensing device 4100 may change the selected content.

The sensing device 4100 according to an embodiment of the present invention may output changed content.

Figure 42:
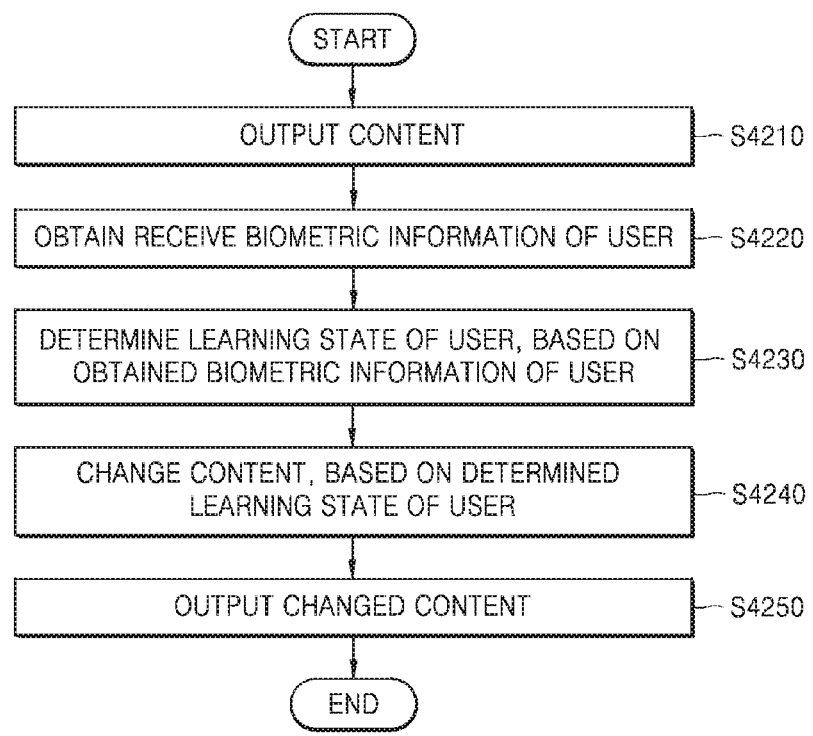
FIG. 42 is a flowchart of a method in which the sensing device according to another embodiment of the present invention provides content.

FIG. 42 is a flowchart of a method in which the sensing device 4100 according to another embodiment of the present invention provides content.

In operation S4210, the sensing device 4100 may detect biometric information of a user. For example, the sensing device 4100 may detect brainwave information of the user from an EEG sensor included therein.

In response to an input of the user of selecting one from a plurality of pieces of content, the sensing device 4100 may detect brainwave information of the user. As another example, the sensing device 4100 may detect brainwave information of the user while some pieces of sub-content of the content selected based on the user input are being output.

In operation S4220, the sensing device 4100 may determine a learning state of the user, based on the detected biometric information of the user.

The sensing device 4100 according to an embodiment of the present invention may determine at least one of a concentration amount, an understanding amount, a stress amount, and a memorization amount of the user, based on the obtained biometric information of the user. For example, based on brainwave information of the user obtained while the some pieces of sub-content of the selected content are being output, the sensing device 4100 may determine a concentration degree, an understanding degree, and a stress degree of the user with respect to the output some pieces of sub-content. The sensing device 4100 may determine the concentration amount, the understanding amount, the stress amount, and the memorization amount by using at least one of the determined concentration degree, the determined understanding degree, and the determined stress degree.

The sensing device 4100 according to an embodiment of the present invention may determine a learning state of the user with respect to other sub-content of content that is to be used in the future, based on the brainwave information of the user obtained while the some pieces of sub-content of the selected content are being output. As another example, the sensing device 4100 may determine a learning state of the user with respect to some pieces of sub-content of already-used content.

In operation S4230, the sensing device 4100 may change the selected content according to the determined learning state of the user.

The selected content may be one of a plurality of pieces of content previously stored in the sensing device 4100. As another example, the selected content may be one of pieces of content that the sensing device 4100 receives from the external content providing server 3940 of FIG. 39 via streaming.

The sensing device 4100 may previously store information about a threshold representing a learning state of the user required to learn the selected content. The threshold is a condition necessary for the user to learn the information included in the selected content, and may be at least one of a preset concentration amount, a preset understanding amount, a preset stress amount, and a preset memorization amount.

The sensing device 4100 may compare the learning state of the user with the threshold for the selected content. When the learning state of the user does not correspond to the threshold, the sensing device 4100 may change the selected content.

For example, when the learning state of the user does not satisfy the threshold, the sensing device 4100 may change the selected content by selecting some of a plurality of pieces of sub-content included in the selected content. As another example, the sensing device 4100 may change the selected content by adding sub-content included in other content to sub-content included in the selected content. However, this is only an embodiment, and the method of changing content is not limited thereto.

In operation S4240, the sensing device 4100 may output changed content. The sensing device 4100 according to an embodiment of the present invention may output metadata about at least one piece of sub-content included in the changed content, together with the changed content. The aforementioned example is merely an embodiment of the present invention, and the sensing device 4100 may output only the changed content.

Figure 43:
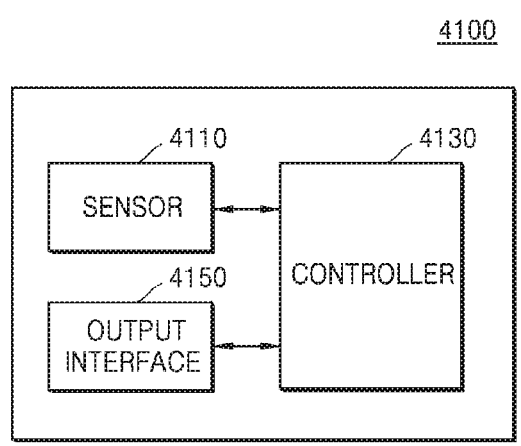
FIG. 43 is a block diagram of the sensing device according to another embodiment of the present invention.

FIG. 43 is a block diagram of the sensing device 4100 according to another embodiment of the present invention.

Referring to FIG. 43, the sensing device 4100 according to another embodiment of the present invention may include a sensor 4110, a controller 4130, and an output interface 4150. However, all of the illustrated components are not essential. The sensing device 4100 may be implemented by more or less components than those illustrated in FIG. 43.

The aforementioned components will now be described in detail.

The sensor 4110 may detect biometric information of a user. For example, the sensor 4110 may detect the brainwave information of the user by using an EEG sensor included therein.

In response to an input of the user of selecting one from a plurality of pieces of content, the sensor 4110 according to an embodiment of the present invention may detect brainwave information of the user. As another example, the sensor 4110 may detect brainwave information of the user while some pieces of sub-content of the content selected based on the user input are being output.

The controller 4130 may determine a learning state of the user, based on the detected biometric information of the user. The controller 4130 according to an embodiment of the present invention may determine at least one of a concentration amount, an understanding amount, a stress amount, and a memorization amount of the user, based on the obtained biometric information of the user. For example, based on brainwave information of the user obtained while the some pieces of sub-content of the selected content are being output, the controller 4130 may determine a concentration degree, an understanding degree, and a stress degree of the user with respect to the output some pieces of sub-content. The controller 4130 may determine the concentration amount, the understanding amount, the stress amount, and the memorization amount by using at least one of the determined concentration degree, the determined understanding degree, and the determined stress degree.

The controller 4130 according to an embodiment of the present invention may determine a learning state of the user with respect to other sub-content of content that is to be used in the future, based on the brainwave information of the user obtained while the some pieces of sub-content of the selected content are being output. As another example, the controller 4130 may determine a learning state of the user with respect to some pieces of sub-content of already-output content.

The server 4130 may change the selected content according to the determined learning state of the user.

The controller 4130 may previously store information about a threshold representing a learning state of the user required to learn the selected content.

The controller 4130 may compare the learning state of the user with the threshold for the selected content. When the learning state of the user does not correspond to the threshold, the controller 4130 may change at least one piece of sub-content included in the selected content. For example, when the learning state of the user does not correspond to the threshold, the controller 4130 may change the selected content by selecting some of the pieces of sub-content included in the selected content.

As another example, the controller 4130 may change the selected content by adding sub-content included in other content to sub-content included in the selected content. However, this is only an embodiment, and the method of changing content is not limited thereto.

The output interface 4150 may output changed content. The output interface 4150 according to an embodiment of the present invention may output metadata about at least one piece of sub-content included in the changed content, together with the changed content. The aforementioned example is merely an embodiment of the present invention, and the output interface 4150 may output only the changed content.

A method according to an embodiment of the present invention may be embodied as program commands executable by various computer means and may be recorded on a computer-readable recording medium. The computer-readable recording medium may include program commands, data files, data structures, and the like separately or in combinations. The program commands to be recorded on the computer-readable recording medium may be specially designed and configured for embodiments of the present invention or may be well-known to and be usable by one of ordinary skill in the art of computer software. Examples of the computer-readable recording medium include a magnetic medium such as a hard disk, a floppy disk, or a magnetic tape, an optical medium such as a compact disk-read-only memory (CD-ROM) or a digital versatile disk (DVD), a magneto-optical medium such as a floptical disk, and a hardware device specially configured to store and execute program commands such as a ROM, a random-access memory (RAM), or a flash memory. Examples of the program commands are advanced language codes that can be executed by a computer by using an interpreter or the like as well as machine language codes made by a compiler.

While one or more embodiments have been described with reference to the figures, it will be understood by those of ordinary skill in the art that various changes in form and details may be made therein without departing from the spirit and scope as defined by the following claims.

The invention claimed is:

1. A method of providing content, performed by a device, the method comprising:
    outputting content from the device;
    receiving biometric information of a user from a sensing device;
    determining a learning state of the user with respect to the content based on the received biometric information;
    changing the content based on the determined learning state of the user; and
    outputting the changed content,
    wherein the determining of the learning state of the user comprises determining at least one of a concentration amount, an understanding amount and a memorization amount of the user with respect to the content, by using brainwave information included in the received biometric information,
    wherein a plurality of content changing methods classified according to values of the concentration amount, the understanding amount and the memorization amount are pre-stored in a memory of the device, and
    wherein the changing of the content includes selecting a content changing method among the plurality of content changing methods pre-stored in the memory based on the determined learning state of the user and the content and changing the content according to the selected content changing method.

2. The method of claim 1, further comprising:
    comparing at least one of the concentration amount, the understanding amount, a stress amount, and the memorization amount of the user with a preset threshold; and
    determining whether to change the content, based on a result of the comparing.

3. The method of claim 1, wherein the changing of the content comprises adding second sub-content, which is at least one piece of sub-content included in other content, to first sub-content, which is at least one piece of sub-content included in the content.

4. The method of claim 1, wherein the changing of the content comprises changing at least one of shapes, colors, sizes, and locations of objects included in at least one piece of sub-content of the content.

5. The method of claim 1, wherein the changing of the content comprises determining at least one of an output time point, an output frequency, and an output speed of at least one piece of sub-content included in the content.

6. The method of claim 1, wherein the changing of the content comprises changing some of objects included in at least one piece of sub-content of the content to an object of other sub-content.

7. A non-transitory computer-readable recording medium having recorded thereon a computer program, which, when executed by a computer, performs the method of claim 1.

8. A device comprising:
    an output interface configured to output content;
    a communicator configured to receive biometric information of a user from a sensing device; and
    a controller configured to determine a learning state of the user with respect to the content based on the received biometric information, and change the content based on the determined learning state,
    wherein the output interface outputs the changed content,
    wherein the determining of the learning state of the user comprises determining at least one of a concentration amount, an understanding amount and a memorization amount of the user with respect to the content, by using brainwave information included in the received biometric information,
    wherein a plurality of content changing methods classified according to values of the concentration amount, the understanding amount and the memorization amount are pre-stored in a memory of the device, and
    wherein the controller is configured to select a content changing method among the plurality of content changing methods pre-stored in the memory based on the determined learning state of the user and the content and change the content according to the selected content changing method.

9. The device of claim 8, wherein the controller compares at least one of the concentration amount, the understanding amount, a stress amount, and the memorization amount of the user with a preset threshold and determines whether to change the content, based on a result of the comparing.

10. The device of claim 8, wherein the controller adds second sub-content, which is at least one piece of sub-content included in other content, to first sub-content, which is at least one piece of sub-content included in the content.

11. The device of claim 8, wherein the controller changes at least one of shapes, colors, sizes, and locations of objects included in at least one piece of sub-content of the content.

12. The device of claim 8, wherein the controller determines at least one of an output time point, an output frequency, and an output speed of at least one piece of sub-content included in the content.

13. The device of claim 8, wherein the controller changes some of objects included in at least one piece of sub-content of the content to an object of other sub content.

* * * * *